United States Patent
Fairhead et al.

(10) Patent No.: US 10,953,052 B2
(45) Date of Patent: Mar. 23, 2021

(54) MODIFYING BACTERIOPHAGE

(71) Applicant: PHICO THERAPEUTICS LTD, Cambridge (GB)

(72) Inventors: Heather Fairhead, Cambridge (GB); Adam Wilkinson, Hertfordshire (GB); Anne Barnard, Cambridge (GB); Emmanuele Severi, Cambridge (GB); Neil Anderson, Hertfordshire (GB); Katy Pitts, Hertfordshire (GB)

(73) Assignee: PHICO THERAPEUTICS LTD, Cambridge (GB)

( * ) Notice: Subject to any disclaimer, the term of this patent is extended or adjusted under 35 U.S.C. 154(b) by 0 days.

(21) Appl. No.: 15/517,732

(22) PCT Filed: Oct. 8, 2015

(86) PCT No.: PCT/EP2015/073296
§ 371 (c)(1),
(2) Date: Apr. 7, 2017

(87) PCT Pub. No.: WO2016/055586
PCT Pub. Date: Apr. 14, 2016

(65) Prior Publication Data
US 2017/0304379 A1   Oct. 26, 2017

(30) Foreign Application Priority Data
Oct. 8, 2014 (GB) .................... 1417810

(51) Int. Cl.
| | | |
|---|---|---|
| *C12N 7/01* | (2006.01) | |
| *A61K 35/76* | (2015.01) | |
| *C12N 7/00* | (2006.01) | |
| *A61K 35/00* | (2006.01) | |

(52) U.S. Cl.
CPC .............. *A61K 35/76* (2013.01); *C12N 7/00* (2013.01); *A61K 35/00* (2013.01); *C12N 2795/00011* (2013.01); *C12N 2795/10121* (2013.01); *C12N 2795/10144* (2013.01)

(58) Field of Classification Search
None
See application file for complete search history.

(56) References Cited

FOREIGN PATENT DOCUMENTS

| | | |
|---|---|---|
| WO | 2002/007742 | 1/2002 |
| WO | 2002/040678 | 5/2002 |
| WO | 2003/076583 | 9/2003 |
| WO | 2004/113375 | 12/2004 |
| WO | 2009/019293 | 2/2009 |
| WO | 2016/055586 | 4/2016 |

OTHER PUBLICATIONS

W. Kot et al. "Identification of the Receptor-Binding Protein in Lytic Leuconostoc pseudomesenteroides Bacteriophages", Applied and Environmental Microbiology 79(10): 3311-3314 (Year: 2013).*

M. Duplessis et al. "Identification of a genetic determinant responsible for host specificity in *Streptococcus thermophilus* bacteriophages", Molecular Microbiology 41(2), 325-336 (Year: 2001).*

Y. Tanji et al. "Quick Selection of a Chimeric T2 Phage That Displays Active Enzyme on the Viral Capsid", Biotechnol. Prog 21:1768-1771 (Year: 2005).*

E. A. Pleteneva et al. "Study of the Diversity in a Group of Phages of Pseudomonas aeruginosa Species PB1 (*Myoviridae*) and Their Behavior in Adsorbtion-Resistant Bacterial Mutants", Russian Journal of Genetics, 44(2): 150-158 (Year: 2008).*

M. Oda et al. "Rapid Detection of *Escherichia coli* O157:H7 by Using Green Fluorescent Protein-Labeled PP01 Bacteriophage", Applied and Environmental Microbiology 70(1):527-534. (Year: 2004).*

Barndard, et al. "SASP: rapid bactericidal activity against USA strains of meticillin-resistant *Staphylococcus aureus*," Clinical Microbiology and Infection, Jan. 1, 2008 Wiley-Blackwell Publishing Ltd, United Kingdom, Switzerland, vol. 14,Nr:s7,pp. S131-S132.

Cass, et al. "F-1548—SASPject: Microbiological Characterisation of a Novel Therapeutic Targeting MDR Pseudomonas aeruginosa," 54th Interscience Conference on Antimicrobial Agents and Chemotherapy (ICAAC), Sep. 5-9, 2014, Washington, DC, Sep. 5, 2014; Sep. 5, 2014-Sep. 9, 2014; pp. F-1548, 1 page.

Cass, et al. "F-1550—SASPject: A novel Antibacterial Technology Targeting MDR Pseudomonas aeruginosa Demonstrating a Low Propensity for Resistance Development," 54th Interscience Conference on Antimicrobial Agents and Chemotherapy (ICAAC), Sep. 5-9, 2014, Washington, DC. Abstract, 1 page.

Cass, et al. "F-1550 SASPject: A novel Antibacterial Technology Targeting MDR Pseudomonas aeruginosa Demonstrating a Low Propensity for Resistance Development," 54th Interscience Conference on Antimicrobial Agents and Chemotherapy (ICAAC); Sep. 5-9, 2014; Washington, DC. Figures, 1 page.

Ceyssens PJ, et al. "Comparative analysis of the widespread and conserved PB1-like viruses infecting Pseudomonas aeruginosa," Environ Microbiol. Nov. 2009;11(11):2874-83.

Le S, et al. "Mapping the tail fiber as the receptor binding protein responsible for differential host specificity of Pseudomonas aeruginosa bacteriophages PaP1 and JG004," PLoS One. Jul. 9, 2013;8(7):e68562.

Mikawa YG, et al. "Surface display of proteins on bacteriophage lambda heads," J Mol Biol. Jan. 1, 1996;262(1):21-30. http://ac.els-cdn.com/S0022283696904957/1-s2.0-S0022283696904957-main.pdf?_tid=8e72afe6-b3be-11e5-8358-00000aacb360&acdnat=1452006852_f1ad476461d30e2718c5d95225d194c2.

Mikawa YG, et al. "Surface display of proteins on bacteriophage lambda heads," J Mol Biol. Sep. 13, 1996;262(1):21-30.

Mushtaq, et al. "A novel antibacterial protein which shows rapid bactericidal activity against MRSA in the presence of other antibiotics," 19th European Congress of Clinical Microbiology and Infectious Diseases Helsinki, Finland, May 16-19, 2009, May 16, 2009; May 16, 2009-May 19, 2009, pp. P-1081.

(Continued)

*Primary Examiner* — Rebecca E Prouty
(74) *Attorney, Agent, or Firm* — Robin L. Teskin; Baker, Donelson, Bearman, Caldwell & Berkowitz PC

(57) ABSTRACT

A method for modifying the genome of a lytic target phage, uses of the method and products thereof are described. Compositions comprising such phage are also described. The compositions may be formulated as a medicament, which are useful for human treatment and may treat various conditions, including bacterial infections.

21 Claims, 19 Drawing Sheets

Specification includes a Sequence Listing.

(56) References Cited

OTHER PUBLICATIONS

Pitts, et al. ". F-1551—SASPject: Efficacy of SASPject against Pseudomonas aeruginosa ATCC 27853 in a Mouse Lung Model," 54th Interscience Conference on Antimicrobial Agents and Chemotherapy (ICAAC), Sep. 5-9, 2014, Washington, DC, Abstract, 1 page.

Pitts, et al. ". F-1551—SASPject: Efficacy of SASPject against Pseudomonas aeruginosa ATCC 27853 in a Mouse Lung Model," 54th Interscience Conference on Antimicrobial Agents and Chemotherapy (ICAAC); Sep. 5-9, 2014; Washington, DC, Figures, 1 page.

Thomason L, et al. "Recombineering: genetic engineering in bacteria using homologous recombination," Curr Protoc Mol Biol. Apr. 2007;Chapter 1:Unit 1.16.

Veesler D, et al. "A common evolutionary origin for tailed-bacteriophage functional modules and bacterial machineries," Microbiol Mol Biol Rev. Sep. 2011;75(3):423-33, first page of table of contents.

Yoichi M, et al. "Alteration of tail fiber protein gp38 enables T2 phage to infect *Escherichia coli* O157:H7," J Biotechnol. Jan. 12, 2005;115(1):101-7.

Dower WJ, Miller JF, Ragsdale CW. "High efficiency transformation of *E. coli* by high voltage electroporation." Nucleic acids research. Jul. 11, 1988;16(13):6127-6145.

Court DL, Sawitzke JA, Thomason LC. "Genetic engineering using homologous recombination." Annual review of genetics. Dec. 2002;36(1):361-88.

Kiro R, Shitrit D, Qimron U. "Efficient engineering of a bacteriophage genome using the type IE CRISPR-Cas system." RNA biology. Jan. 1, 2014;11(1):42-4.

Yu D, Ellis HM, Lee EC, Jenkins NA, Copeland NG. "An efficient recombination system for chromosome engineering in *Escherichia coli*." Proceedings of the National Academy of Sciences. May 23, 2000;97(11):5978-83.

Marinelli LJ, et al. "BRED: a simple and powerful tool for constructing mutant and recombinant bacteriophage genomes," PLoS One. 2008;3(12):e3957.

Marinelli LJ, et al. "Recombineering: A powerful tool for modification of bacteriophage genomes," Bacteriophage. Jan. 1, 2012;2(1):5-14.

Pires DP, et al. "Genetically Engineered Phages: a Review of Advances over the Last Decade," Microbiol Mol Biol Rev. Jun. 1, 2016;80(3):523-43.

Martel B, et al. "CRISPR-CAS: an efficient tool for genome engineering of virulent bacteriophages," Nucleic Acids Res. Aug. 2014;42(14):9504-13.

Tao P, et al. "In vitro and in vivo delivery of genes and proteins using the bacteriophage T4 DNA packaging machine," Proc Natl Acad Sci U S A. Apr. 9, 2013;110(15):5846-51.

DePorter SM, et al. "Engineered M13 bacteriophage nanocarriers for intracellular delivery of exogenous proteins to human prostate cancer cells," Bioconjug Chem. Sep. 17, 2014;25(9)1620-5.

\* cited by examiner

Figure 6A

```
SPM-1    MTTPELIPSPFAAQGDKDPIPQTSSTGFANLRDGYTPDYEISLASNNPQAKAVERKIQNQ  60
F8       VITPELIPSPFAAQGDKDPIPQTSSTGFANLRDGYTPDYEISLASNNPQAKAVERKIQNQ  60
PB1      MTTPELIPSPFAAQGDKDPIPQTSSTGFANLRDGYTPDYEISLASNNPQAKAVERKIQNQ  60
C36      VITPELIPSPFAAQGDKDPIPQTSSTGFANLRDGYTPDYEISLASNNPQAKAVERKIQNQ  60
LBL3     MTTPELIPSPFAAQGDKDPIPQTSSTGFANLRDGYTPDYEISLASNNPQAKAVERKIQNQ  60
Phi33    VITPELIPSPFAAQGDKDPIPQTSSTGFANLRDGYTPDYEISLASNNPQAKAVERKIQNQ  60
LMA2     MTTPELIPSPFAAQGDKDPIPQTSSTGFANLRDGYTPDYEISLASNNPQAKVVERKIQNQ  60
KPP12    MTTPELIPSPFAAQGDKDPIPQTSSTGFANLRDGYTPDYEISLASNNPQAKAVERKIQNQ  60
JG024    VITPELIPSPFAAQGDKDPIPQTSSTGFANLRDGYTPDYEISLASNNPQAKAVERKIQNQ  60
PTP92    VITPELIPSPFAAQGDKDPIPQTSSTGFANLRDGYTPDYEISLASNNPQAKAVERKIQNQ  60
NH-4     MTTPELIPSPFAAQGDKDPIPQTSSTGFANLRDGYTPDYEISLASNNPQAKAVERKIQNQ  60
14-1     MTTPELIPSPFAAQGDKDPIPQTSSTGFANLRDGYTPDYEISLASNNPQAKAVERKIQNQ  60
PTP47    VITPELIPSPFAAQGDKDPIPQTSSTGFANLRDGYTPDYEISLASNNPQAKAVERKIQNQ  60
SN       MTTPELIPSPFAAQGDKDPIPQTSSTGFANLRDGYTPDYEISLASNNPQAKAVERKIQNQ  60
           :************************************************ *******

SPM-1    LFFIATQNAQAWQRQMAPPWFQGMPGGYEQNAEVVRVGNDGIMRRYRSMVNANASDPLSS 120
F8       LFFIATQNAQAWQRQMAPPWFQGMPGGYEQNAEVVRVGNDGIMRRYRSMVNANASDPLSS 120
PB1      LFFIATQNAQAWQRQMAPPWFQGMPGGYEQNAEVVRVGNDGIMRRYRSMVNANASDPLSS 120
C36      LFFIATQNAQAWQRQMAPPWFQGMPGGYEQNAEVVRVGNDGIMRRYRSMVNANASDPLSS 120
LBL3     LFFIATQNAQAWQRQMAPPWFQGMPGGYEQNAEVVRVGNDGIMRRYRSMVNANASDPLSS 120
Phi33    LFFIATQNAQAWQRQMAPPWFQGMPGGYEQNAEVVRVGNDGIMRRYRSMVNANAIDPLSS 120
LMA2     LFFIATQNAQAWQRQMAPPWFQGMPGGYEQNAEVVRVGNDGIMRRYRSMVNANASDPLSS 120
KPP12    LFFIATQNAQAWQRQMAPPWFQGMPGGYEQNAEVVRVGNDGIMRRYRSMVNANASDPLSS 120
JG024    LFFIATQNAQAWQRQMAPPWFQGMPGGYEQNAEVVRVGNDGIMRRYRSMVNANASDPLSS 120
PTP92    LFFIATQNAQAWQRQMAPPWFQGMPGGYEQNAEVVRVGNDGIMRRYRSMVNANASDPLSS 120
NH-4     LFFIATQNAQAWQRQMAPPWFQGMPGGYEPNAEVVRVGNDGIMRRYRSMVNANASDPLSS 120
14-1     LFFIATQNAQAWQRQMAPPWFQGMPGGYEQNAEVVRVGNDGIMRRYRSMVNANASDPLSS 120
PTP47    LFFIATQNAQAWQRQMAPPWFQDMPGGYEQNAEVVRVGNDGIMRRYRSMVNANASDPLSS 120
SN       LFFIATQNAQAWQRQMAPPWFQGMPGGYEQNAEVVRVGNDGIMRRYRSMVNANASDPLSS 120
         *********************.******:********************* *****

SPM-1    TTWEEQPAWSVMRSNIPMPAGGSGLSSGGEVITTGRNFNDLLNGTWEFFSDSVVVASQNA 180
F8       TTWEEQPAWSVMRSNIPMPAGGSGLSSGGEVITTGRNFNDLLNGTWEFFSDSVVAASQNA 180
PB1      TTWEEQPAWSVMRSNIPMPAGGPGLSSGGEVITTGRNFNDLLNGTWEFFSDSVVVASQNA 180
C36      TTWEEQPAWSVMRSSIPMPAGGPGLSSGGEVITTGRNFNDLLNGTWEFFSDSVVVASQNA 180
LBL3     TTWEEQPAWSVMRSNIPMPAGGPGLSSGGEVITTGRNFNDLLNGTWEFFSDSVVIASQNA 180
Phi33    TTWEEQPAWSVMRSNIPMPAGGPGLSSGGEVITTGRNFNDLLNGTWEFFSDSVVVASQNA 180
LMA2     TTWEEQPAWSAMRSNIPMPAGGPGLSSGGEVITTGRNFNDLLNGTWEFFSDSVVIASQNA 180
KPP12    TTWEEQPAWSAMRSNIPMPAGGPGLSSGGEVITTGRNFNDLLNGTWEFFSDSVVIASQNA 180
JG024    TTWEEQPAWSVMRTNIPMPAGGPGLSSGGEVITTGRNFNELLNGTWEFFSDAIVVASQNA 180
PTP92    TTWEEQPAWSVMRTNIPMPAGGPGLSSGGEVITTGRNFNELLNGTWEFFSDAIVVASQNA 180
NH-4     TTWEEQPAWSVMRTNIPMPAGGPGLSSGGEVITTGRNFNELLNGTWEFFSDAIVVASQNA 180
14-1     TTWEEQPAWSVMRSSIPMPAGGPGLSSGGEVITTGRNFNDLLNGTWEFFSDSVVIASQNA 180
PTP47    TTWEEQPAWSAMRSNIPMPAGGPGLSSGGEVITTGRNFNDLLNGTWEFFSDSVVIASQNA 180
SN       TTWEEQPAWSVMRSNIPMPAGGPGLSSGGEVITTGRNFNDLLNGTWEFFSDSVVVASQNA 180
         **********.**;.******.***********:*********;;* *****
```

Figure 6B

```
SPM-1   PVYPASAGAAAGMLEAKSWVSGANTFCVQRYTDRVGNVAVRGLNAGAWTNWMYAVNVMAL 240
F8      PVYPASAGAAAGMLEAKSWVSGANTFCVQRYTDRVGNVAVRGLNAGAWTNWMYAVNVMAL 240
PB1     PVYPASAGAAAGMLEAKSWISGSNTFCVQRYTDRVGNVAVRGLNAGAWTNWMYAVNVMAL 240
C36     PVYPASAGAAAGMLEAKSWISGSNTFCVQRYTDRVGNVAVRGLNAGAWTNWMYAVNVMAL 240
LBL3    PVYPASAGAAAGMLEAKSWVSGANTFCVQRYTDRVGNVAVRGLNAGAWTNWMYAVNVMAL 240
Phi33   PVYPASAGAAAGMLEAKSWVSGANTFCVQRYTDRVGNVAVRGLNAGAWTNWMYAVNVMAL 240
LMA2    PVYPASAGAAAGMLEAKSWVSGANTFCVQRYTDRVGNVAVRGLNAGAWTNWMYAVNVMAL 240
KPP12   PVYPASAGAAAGMLEAKSWVSGANTFCVQRYTDRVGNVALRGLNAGAWTNWMYAVNVMAL 240
JG024   PVYPASAGAAAGMLEAKSWVSGSNTFCVQRYTDRVGNVAVRGLNAGAWTNWMYAVNVMAL 240
PTP92   PVYPASAGAAAGMLEAKSWVSGSNTFCVQRYTDRVGNVAVRGLNAGAWTNWMYAVNVMAL 240
NH-4    PVYPASAGAAAGMLEAKSWVSGSNTFCVQRYTDRVGNVAVRGLNAGAWTNWMYAVNVMAL 240
14-1    PVYPASAGAAAGMLEAKSWISRSNTFCVQRYTDRVGNVAVRGLNAGEWTNWMYAVNVMAL 240
PTP47   PVYPASAGAAAGMLEAKSWVSGANTFCVQRYTDRVGNVAVRGLNAGAWTNWMYAVNVMAL 240
SN      PVYPASAGAAAGMLEAKSWVSGANTFCVQRYTDRVGNVAVRGLNAGAWTNWMYAVNVMAL 240
        ****************:* ,****************:***** *************

SPM-1   QQGRVTYGVAAGSANAYTLTLVPQLQGGLVDGMVLRVKFNAMNTGASTINVSGFGSKAIV 300
F8      QQGRVTYGVAAGSANAYTLTLVPQLQGGLVDGMVLRVKFNAMNTGASTINVSGFGSKAIV 300
PB1     QQGRVTYGVAAGSANAYTLTLVPQLQGGLVDGMILRVKFNTVNTGASTINVSGFGAKAIV 300
C36     QQGRVTYGVAAGPANAYTLTLVPQLQGGLVDGMILRVKFNTVNTGASTINVSGFGAKAIV 300
LBL3    QQGRVTYGVAAGSANAYTLTLVPQLQGGLVDGMILRVKFNTMNTGASTINVSGFGAKAIV 300
Phi33   QQGRVTYGVAAGSANAYTLTLVPQLQGGLVDGMILRVKFNTMNTGASTINVSGLGAKAIV 300
LMA2    QQGRVTYGVAAGSANAYTLTLVPQLQGGLVDGMILRVKFNTMNTGATTINVSGLGAKAIV 300
KPP12   QQGRVTYGVAAGSANAYTLTLVPQLQGGLVDGMILRVKFNTMNTGASTINVSGLGAKAIV 300
JG024   QHGRVTYGTAAGPANAYTLTLVPQIQGGLVDGMILRVKFNTMNTGATTINVSGLGAKAIV 300
PTP92   QHGRVTYGTAAGPANAYTLTLVPQIQGGLVDGMILRVKFNTMNTGATTINVSGLGAKAIV 300
NH-4    QHGRVTYGTAAGPANAYTLTLVPQIQGGLVDGMILRVKFNTMNTGATTINVSGLGAKAIV 300
14-1    QQGRVTYGVAAGPANAYTLTLVPQLQGGLVDGMILRVKFNTVNTGASTINVSGLGAKAIV 300
PTP47   QQGRVTYGVAAGSANAYTLTLVPQLQGGLVDGMILRVKFNTMNTGATTINVSGLGAKAIV 300
SN      QQGRVTYGVAAGSANAYTLTLVPQLQGGLVDGMILRVKFNTMNTGASTINVSGLGAKAIV 300
        *:****,***,**********:********:*****::****:******:*:****

SPM-1   GAANFPLTGGELGQGLIAELVFDATGDRWRILAGAPRIQVGNADQDYQAPSWKQVKDYVA 360
F8      GAANFPLTGGELGQGLIAELVFDATGDRWRILAGAPRIQVGNADQDYQAPSWKQVKDYVA 360
PB1     GAANFPLTGGELGQGLIAELVFDATGDRWRILAGAPRIQVGNADQDYQAPSWKQVKDYVA 360
C36     GAANFPLTGGELGQGLIAELVFDATGDRWRILAGAPRIQVGNADQDYQAPSWKQVKDYVA 360
LBL3    GAANFPLTGGELGQGLIAELVFDATGDRWRILAGAPRIQVGNADQDYQAPSWKQVKDYVA 360
Phi33   GAANFPLTGGELGQGLIAELVFDAAGDRWRILAGAPRIQVGNADQDYQAPSWKQVKDYVA 360
LMA2    GAANFPLTGGELGQGLIAELVFDAAGDRWRILAGAPRIQVGNADQDYQAPSWKQVKDYVA 360
KPP12   GAANFPLTGGELGQGLIAELVFDAAGDRWRILAGAPRIQVGNADQDYQAPSWKQVKDYVA 360
JG024   GAANFPLTGGELGQGLIAELVFDAAGDRWRILAGAPRIQVGNADQDYQAPSWKQVKDYVE 360
PTP92   GAANFPLTGGELGQGLIAELVFDAAGDRWRILAGAPRIQVGNADQDYQAPSWKQVKDYVE 360
NH-4    GAANFPLTGGELGQGLIAELVFDAAGDRWRILAGAPRIQVGNADQDYQAPSWKQVKDYVA 360
14-1    GAANFPLTGGELGQGLIAELVFDAAGDRWRILAGAPRIQVGNADQDYQAPSWKQVKDYVA 360
PTP47   GAANFPLTGGELGQGLIAELVFDAAGDRWRILAGAPRIQVGNADQDYQAPSWKQVKDYVA 360
SN      GAANFPLTGGELGQGLIAELVFDAAGDRWRILAGAPRIQVGNADQDYQAPSWKQVKDYVA 360
        ***********************:***********************************

SPM-1   SQKLTEVDWADVVNKPNVAIQDTTPWFANLELSDARPFIDFHFNNNRAKDFDYRFISEAD 420
F8      SQKLTEVDWADVVNKPNVAIQDTTPWFANLELSDARPFIDFHFNNNPAKDFDYRFISEAD 420
PB1     SQKLTEVDWADVVNKPNVAIQDTTPWFANLELSDARPFIDFHFNNNPAKDFDYRFISEAD 420
C36     SQKLTEVDWADVVNKPNVAIQDTTPWFANLELSDARPFIDFHFNNNPAKDFDYRFISEAD 420
LBL3    SQKLTEVDWADVVNKPNVAIQDTTPWFANLELSDARPFIDFHFNNNPAKDFDYRFISEAD 420
Phi33   SQKLTEVDWADVVNKPNVAIQDTTPWFANLELSDARPFIDFHFNSNPAKDFDYRLISEAD 420
LMA2    SQKLTEVDWADVVNKPNVAIQDTTPWFANLELSDARPFIDFHFNSNPAKDFDYRLISEAD 420
KPP12   SQKLTEVDWADVVNKPNVAIQDTTPWFANLELSDARPFIDFHFNNNPAKDFDYRFISEAD 420
JG024   SQKLTEVDWTDVVNKPNVAIQDTTPWFANLELSDARPFIDFHFNSNPAKDFDYRLISEAD 420
PTP92   SQKLTEVDWTDVVNKPNVAIQDTTPWFANLELSDARPFIDFHFNSNPAKDFDYRLISEAD 420
NH-4    SQKLTEVDWTDVVNKPNVAIQDTTPWFANLELSDARPFIDFHFNSNPAKDFDYRLISEAD 420
14-1    SQKLTEVDWADVVNKPNVAIQDTTPWFANLELSDARPFIDFHFNSNPAKDFDYRLISEAD 420
PTP47   SQKLTEVDWADVVNKPNVAIQDTTPWFANLELSDARPFIDFHFNSNPAKDFDYRLISEAD 420
SN      SQKLTEVDWADVVNKPNVAIQDTTPWFANLELSDARPFIDFHFNSNPAKDFDYRLISEAD 420
        *********:***************************:*****,*********:*****
```

Figure 6C

```
SPM-1    GSMAFYSRQGSAGPTQDILFSRSNVTFLQPRLDVAKNLAYIANSGPLWQNTTADQPGWKF 480
F8       GSMAFYSRQGSAGPTQDILFSRSNVTFLQPRLDVAKNLAYIANSGPLWQNTTADQPGWKF 480
PB1      GSMAFYSRQGSAGPTQDILFSRSNVTFLQPRLDVAKNLAYIANSGPLWQNTTADQPGWKF 480
C36      GSMAFYSRQGSAGPTQDILFSRSNVTFLQPRLDVAKNLAYIANSGPLWQNTTADQPGWKF 480
LBL3     GSMAFYSRQGSAGPTQDILFSRSNVTFLQPRLDVAKNLAYIANSGPLWQNTTADQPGWKF 480
Phi33    GSLAFYSRQGSAGPTQDILFNRNSVTFFQPRLDVAKNLAYIANSGPLWQNTTADQPGWKF 480
LMA2     GSLAFYSRQGSAGPTQDILFNRNSVTFFQPRLDVAKNLAYIANSGPLWQNTTADQPGWKF 480
KPP12    GSMAFYSRQGSAGPTQDILFSRSNVTFLQPRLDVAKNLAYIANSGSLWQNTTADQPGWKF 480
JG024    GSLAFYSRQGSAGPTQDILFNRNSVTFFQPRLDVAKNLAYIANSGPLWQNTTADQPGWKF 480
PTP92    GSLAFYSRQGSAGPTQDILFNRNSVTFFQPRLDVAKNLAYIANSGPLWQNTTADQPGWKF 480
NH-4     GSLAFYSRQGSAGPTQDILFNRNSVTFFQPRLDVAKNLAYIANSGPLWQNTTADQPGWKF 480
14-1     GSLAFYSRQGSAGPTQDILFNRNSVTFFQPRLDVAKNLAYIANSGPIWQNTTADQPGWKF 480
PTP47    GSLAFYSRQGSAGPTQDILFNRNSVTFFQPRLDVAKNLAYIANSGPLWQNTTADQPGWKF 480
SN       GSLAFYSRQGSAGPTQDILFNRNSVTFFQPRLDVAKNLAYIANSGSLWQNTTADQPGWKF 480
         **:****************.*..***:**************.;*************

SPM-1    TFAQGVDANNNAVIAVNTTNPDGSYRSQIMRWDWASTNVIFNNRPLFAGQYVPWDSGNFD 540
F8       TFAQGVDANNNAVIAVNTTNPDGSYRSQIMRWDWASTNVIFNNRPLFAGQYVPWDSGNFD 540
PB1      TFAQGVDANNNAVIAVNTTNPDGSYRSQVMRWDWASTNVIFNNRPLFAGQYVPWDSGNFD 540
C36      TFAQGVDANNNAVIAVNTTNPDGSYRSQIMRWDWASTNVIFNNRPLFAGQYVPWDSGNFD 540
LBL3     TFAQGVDANNNAVIAVNTTNPDGSYRSQIMRWDWASTNVIFNNRPLFAGQYVPWDSGNFD 540
Phi33    TFAQGVDANNNAVIAVNTTNPDGSYRSQIMRWDWASTNVIFNNRPLFAGQYVPWDSGNFD 540
LMA2     TFAQGVDANNNAVIAVNTTNPDGSYRSQVMRWDWASTNVIFNNRPLFAGQYTPWDSGNFD 540
KPP12    TFAQGVDANNNAVIAVNTTNPDGSYRSQIMRWDWASTNVIFNNRPLFAGQYTPWDSGNFD 540
JG024    TFAQGVDANNNAVIAVNTTNPDGSYRSQVMRWDWASTNVIFNNRPLFAGQYTPWDSGNFD 540
PTP92    TFAQGVDANNNAVIAVNTTNPDGSYRSQVMRWDWASTNVIFNNRPLFAGQYTPWDSGNFD 540
NH-4     TFAQGVDANNNAVIAVNTTNPDGSYRSQVMRWDWASTNVIFNNRPLFAGQYTPWDSGNFD 540
14-1     TFAQGVDANNNAVIAVNTTNPDGSYRSQVMRWDWASTNVIFNDRPLFAGQYTPWDSGNFD 540
PTP47    TFAQGVDANNNAVIAVNTTNPDGSYRSQVMRWDWASTNVIFNNRPLFAGQYTPWDSGNFD 540
SN       TFAQGVDANNNAVIAVNTTNPDGSYRSQVMRWDWASTNVIFNNRPLFAGQYTPWDSGNFD 540
         ********************************:*************.********

SPM-1    PATKLTVGTTNNISGPTGIPNTTSNTGNMNTWGSSSTTASYGNAALQIFGRGGGEPAAIY 600
F8       PATKLTVGTTNNISGPTGIPNTTSNTGNMNTWGSSSTTASYGNAALQIFGRGGGEPAAIY 600
PB1      PATKLTVGTTNNISGPTGIPNTTSNTGNMNTWGSSSTTASYGNAALQIFGRGGGEPAAIY 600
C36      PATKLTVGTTNNISGPTGIPNTTSNTGNMNTWGSSSTTASYGNAAVQIFGRGDGEPAAIY 600
LBL3     PATKLTVGTTNNISRPTGIPNTTSNTGNMNTWGSSSTTASYGNAALQIFGRGGGEPAAIY 600
Phi33    PSTKLTVNATNQIAGPTGIPNTNGNTGNMNTWGSGSTTASYGNAALQIFGKGGGEPAALY 600
LMA2     PSTKLTVNATNQIAGPTGIPNTNGNTGNMNTWGSSSTTASYGNAALQIFGKGGGEPAALY 600
KPP12    PSTKLTVNATNQIAGPTGIPNTNGNTGNMNTWGSSSTTASYGNAALQIFGKGGGEPAALY 600
JG024    PSTKLTVSATNQISGPTGIPNTNGNTGNMNTWGSGSTTASYGNAIQIFGKGGGEPAAIY 600
PTP92    PSTKLTVSATNQIAGPTGIPNTNGNTGNMNTWGSGSTTASYGNAAIQIFGKGGGEPAAIY 600
NH-4     PSTKLTVSATNQIAGPTGIPNTNGNTGNMNTWGSGSTTASYGNAAIQIFGKGGGEPAAIY 600
14-1     PSTKLTVSATNQIAGPTGIPNTNGNTGNMNTWGSGSTTASYGNAAIQIFGKGGGEPAAIY 600
PTP47    PSTKLTVSATNQIAGPTGIPNTNGNTGNMNTWGSGSTTASYGNAAIRIFGKGGGEPAAIY 600
SN       PSTKLTVRATNQIAGPTGIQNTNGNTGNMNTWGSGSTTASYGNAAIQIFGKGGGEPAAIY 600
         *:*****..**:*:  ****:**..*********.**********::***:*.*****:*

SPM-1    FDNSQTGWYLGMDKDGQLKPAGWSLGNMSYVVTDESNIRNHVNGMSGAPVWGGQWFWGEW 660
F8       FDNSQTGWYLGMDKDGQLKPAGWSLGNMSYVVTDESNIRNHVNGMSGAPVWGGQWFWGEW 660
PB1      FDNSQTGWYLGMDKDGQLKPAGWSLGNMSYVVTDESNIRNHVNGMSGAPVWGGQWFWGEW 660
C36      FDNSQTGWYLGMDKDGQLKPAGWSLGNMSYVVTDESNIRFHVNSMAGTPVWGGNEFWGPW 660
LBL3     FDNSQTGWYLGMDKDGQLKPAGWSLGNMSYVVTDESNIRFHVNSMAGTPVWGGNEFWGPW 660
Phi33    FDNSQTGWYLGMDKDGQLKPAGWSLGNMAYVITDESNIRFHVNSMAGTPVWGGNEFWGPW 660
LMA2     FDNSQTGWYLGMDKDGQLKPAGWSLGNMSYVITDELNIRNHINGMAARPVWGGNEFWGPW 660
KPP12    FDNSQTGWYLGMDKDGQLKPAGWSLGNMAYVITDESNIRFHVNSMAGTPVWGGNEFWGSW 660
JG024    FDNSQTGWYLGMDKDGQLKPAGWSLGNMSYVITDESNIRTHINTMAARPIWGNVEFWGPW 660
PTP92    FDNSQTGWYLGMDKDGQLKPAGWSLGNMSYVITDESNIRTHINTMAARPIWGNVEFWGPW 660
NH-4     FDNSQTGWYLGMDKDGQLKPAGWSLGNMSYVITDESNIRTHINTMAARPIWGNVEFWGPW 660
14-1     FDNSQTGWYLGMDKDGRLKPAGWSLGNMSYVITDESNIRTHINTMAARPIWGNVEFWGPW 660
PTP47    FDNSQTGWYLGMDKDGQLKPAGWSLGNMSYVITDESNIRTHINTMAARPIWGNVEFWGPW 660
SN       FDNSQTGWYLGMDKDGQLKPAGWSLGNMSYVITDESNIRTHINTMAARPIWGGVEFWGPW 660
         ****************:***********:**:*** *** *:*  *:.*.**   *** *
```

Figure 6D

```
SPM-1   NFNPNTKLTIKAGTQETSSTAIFSGTLPFAPIASLSDYSQAPLTIYN--SPTGPSAKPAV 718
F8      NFNPNTKLTIKAGTQETSSTAIFSGTLPFAPIASLSDYSQAPLTIYN--SPTGPSAKPAV 718
PB1     NFNPNTKLTIKAGTQETSSTAIFSGTLPFAPIASLSDYSQAPLTIYN--SPTGPSAKPAV 718
C36     NFNPNTKLTIKAGTQETSSTAIFSGTMPFAPIASLSDYSQAPLTIYN--SPTGPSAKPAV 718
LBL3    NFNPNTKLTIKAGTQETSSTAIFSGTMPFAPIASLSDYSQAPLTVYN--SPTGPSAKPAV 718
Phi33   NFNPNTKLTIKAGTQETSSTAIFSGTMPFAPIASLSDYSQAPLTVYN--APTGPSAKPAV 718
LMA2    NFNPNTKLTIKAGTQETSSTAIYSGTMPFAPIASLSDYSQAPLTIYN--APTGPSAKPAV 718
KPP12   NFNPNTKLTIKAGTQETSSTAIFSETMPFAPIASLSDYSQAPLTIYN--APTGPSAKPAV 718
JG024   NFDPNLKLTLNAFNDSSYTRMTNSGAKDVG-IASMTSYADAAMSFFNYEASNPTGPRAAV 719
PTP92   NFDPNLKLTLNAFNDSSYTRMTNSGAKDVG-IASMTSYADAAMSFFNYEASNPTGPRAAV 719
NH-4    NFNPNTKLTLGSFNDSQHTRMVNSAAKDVG-IASMTSYADAAMSFFNYEASTPTGNRAAV 719
14-1    NFDPNLKLTLNAFNDSSYTRMTNSGAKDVG-IASMTSYADAAMSFFNYEASNPTGPRAAV 719
PTP47   NFNPNTKLTLGSFNDGQHTRMVNSAAKDVG-IASMTSYADAAMSFFNYEASTPTGNRAAV 719
SN      NFNPNTKLTLGSFNDSQHTRMVNSAAKDVG-IASMTSYADAAMSFFNYEASTPTGNRAAV 719
        **:** ***: : .:    *  :  .,. ***::.*:*.::,:*  :.. ..  :,**

SPM-1   IAFIRPGNWGAFFGIDTDNKLKWGGGSLGNNSREIADSSNIMNLWASNPTAPSWNGQTVW 778
F8      IAFIRPGNWGAFFGIDTDNKLKWGGGSLGNNSREIADSSNIMNLWASNPTAPSWNGQTVW 778
PB1     IAFIRPGNWGAFFGIDTDNKLKWGGGSLGNNSREIADSSNIMNLWASNPTAPSWNGQTVW 778
C36     IAFIRPGNWGAFFGIDTDNKLKWGGGSLGNSSREIADSSNIMNLWAANPTAPSWNGQTVW 778
LBL3    IAFIRPGNWGAFFGIDTDNKLKWGGGSLGNSSREIADSSNIMNLWAANPTAPTWNGQTIW 778
Phi33   IAFIRPGNWGAFFGIDTDNKLKWGGGSLGNSSREIADSSNIMNLWAANPTAPSWNGQTIW 778
LMA2    IAFIRPGNWGAFFGLDTDNKLKWGGGSLGNSSMEIADSSNIMNLWAANPTAPTWNGQTVW 778
KPP12   IAFIRPGNWGAFFGLDTDNKLKWGGGSLGNSSREIADSRNIMNLWAANPTAPTWNGQTIW 778
JG024   ISFVRNGSRGVLFGLDSDNKLKWGGYSLGAVAFEIADSNNLMSLWSSHAAAPNWNGQTIW 779
PTP92   ISFVRNGSRGVLFGLDSDNKLKWGGYSLGAVAFEIADSNNLMSLWSSHAAAPNWNGQTIW 779
NH-4    ISFVRNGARGVLFGLDTDNKLKWGGYSLGAVAFEIADSNNLMSLWSSHAAAPNWNGQTIW 779
14-1    ISFVRNGSRGVLFGLDSDNKLKWGGYSLGAVAFEIADSNNLMSLWSSHAAAPNWNGQTIW 779
PTP47   ISFVRNGSRGVLFGLDTDNKLKWGGYSLGAVAFEIADSNNLMSLWSSHAAAPNWNGQTIW 779
SN      ISFVRNGARGVLFGLDTDNKLKWGGYSLGAVAFEIADSNNLMSLWSSHAAAPNWNGQTIW 779
        *:*:* *   *,:**:*:******* ***   :  ***** *:*.**::::.:**.******:*

SPM-1   RSGNFDPATKVDLNAANATNGSMIFNRISGTGSGIASSGRVGAINLQNGAHSGQAAAVTF 838
F8      RSGNFDPATKVDLNAANATNGSMIFNRISGTGSGIASSGRVGAINLQNGAHSGQAAAVTF 838
PB1     RSGNFDPATKVDLNAANATNGNMIFNRISGTGSGIASSGRVGAINLQNGAHSGQAAAVTF 838
C36     RSGNFDPATKVDLNAANATNGNMVFNRISGTGSGIASSGRVGAINLQNGAHSGQAAAVTF 838
LBL3    RSGNFDPATKVDLNAANATNGNMIFNRIAGTGSGIASSDRVGAISLQNGATAGAAAAVTF 838
Phi33   RSGNFDPATKVDLNAANATNGNMIFNRIAGTGSGIASSGRVGAINLQNGEHSGQAAAVTF 838
LMA2    RSGNFDPATKVDLNAPNATNGNMIFNRIAGTGSGIASSGRVGAISLQNGATAGAAAAVTF 838
KPP12   RSGNFDPATKVDLNAPNATNGNMIFNRIAGTGSGIASSGRVGAISLQNGATAGAAAAVTF 838
JG024   RSGNFNPDTKATLAARNTTSSPTIFS---YGASGIASTGQVGALVVENNSVTNTAAAITF 836
PTP92   RSGNFNPDTKATLAARNTTSSPTIFS---YGASGIASTGQVGALVVENNSVTNTAAAITF 836
NH-4    RSGNFNPDTKATLAARNTTSSPTIFS---YGASGIASTGQVGALVVENNSVTNTAAAITF 836
14-1    RSGNFNPDTKATLAARNTTSSPTIFS---YGASGIASTGQVGALVVENNSVTNTAAAITF 836
PTP47   RSGNFNPDTKATLAARNTTSSPTIFS---YGASGIASTGQVGALVVENNSVTNTAAAITF 836
SN      RSGNFNPDTKATLAARNTTSSPTIFS---YGASGIASTGQVGALVVENNSVTNTAAAITF 836
        *****:*  **. * * *;*.. :*.       ,*****::.:***: ::*. .. ***:**

SPM-1   ERGGSIFVNFGLDTDNVLKVGGGNLGANAYPVIHAGNYNNYINQALVQVGLGGVGSYGIF 898
F8      ERGGSIFVNFGLDTDNVLKVGGGNLGANAYPVIHAGNYNNYINQALVQVGLGGVGSYGIF 898
PB1     ERGGSIFVNFGLDTDNVLKVGGGNLGANAYPVIHAGNYNNYINQALVQVGLGGVGSYGIF 898
C36     ERGGSIFVNFGLDTDNVLKVGGGNLGANAYPVIHAGNYNNYINQALVQVGLGGVGSYGIF 898
LBL3    ERGGGFFVNFGLDTDNVLKVGGGNLGANAYPVIHAGNYNNYINQALVQVGLGGVGSYGIF 898
Phi33   ERGGSIFVNFGLDTDNVLKVGGGNLGANAYPVIHAGNYNNYINQALVQVGLEGVGSYGIF 898
LMA2    ERGGGFFVNFGLDTDNVLKVGGGNLGANAYPVIHAGNYNSYINQALVQVGLGGVGSYAAL 898
KPP12   ERGG-FFVNFGLDTDNVLKVGGGNLGANAYPVIHAGNYNSYINQALVQVGLGGVGSYAAL 897
JG024   HSPQKYQVNFGLDADNVVKIGGGTMGGVAYPIIHSGNYNNYINQALVQVGLGGVGSYAIL 896
PTP92   HSPQKYQVNFGLDADNVVKIGGGTMGGVAYPIIHSGNYNNYINQALVQVGLGGVGSYAIL 896
NH-4    HSPQKYQVNFGLDADNVVKIGGGTMGGVAYPIIHSGNYNNYINQALVQVGLGGVGSYAIL 896
14-1    HSPQKYQVNFGLDADNVVKIGGGTMGGVAYPIIHSGNYNNYINQALVQVGLGGVGSYGIF 896
PTP47   HSPQKYHVNFGLDADNVVKIGGGTMGGVAYPIIHSGNYNNYINQALVQVGLGEVGSYGIF 896
SN      HSPQKYQVNFGLDADNVVKIGGGTMGGVAYPIIHSGNYNNYINQALVQVGLGGVGSYGIF 896
        ,    ******:***,:***.:*.   ***;**,*****,************   ****, :
```

Figure 6E

```
SPM-1   AVLDNAAPIATVQPGVVVDGSILIYSSCAANYNSGQKPAGTWRCMGYVVNRDANTADSAT 958
F8      AVLDNAAPIATVQPGVVVDGSILIYSSCAANYNSGQKPAGTWRCMGYVVNRDANTADSAT 958
PB1     AVLDNAAPIATVQPGVVVDGSILIYSSCAANYNSGQKPAGTWRCMGYVVNRDANTPDSAT 958
C36     AVLDNAAPIATVQPGVVVDGSILIYSSCSANYNSGQRPAGTWRCMGYVVNRDANTPDSAT 958
LBL3    AVLDYAAPTATVQPGVIVDGSILIYSSCSAHYNSGQRPAGTWRCMGYVLNRDARDPDSAT 958
Phi33   AVLDNAAPTATVQPGVVVDGSILIYSSCAANYNSGKRPAGTWRCMGYVVNRDANTPDSAT 958
LMA2    AVYDTSAPASSVGPGTILDGSVLFYSSFNANFRSGTKPTGTWRCMGYILNRDGTNPDSAT 958
KPP12   AVYDTSAPASSVGPGTILDGSVLFYSSFDANFRSGTKPTGTWRCMGYVLNRDGTNPDSAA 957
JG024   AVLDTSAPAASIAPGTIMDSSKLFYSSCDSTYRSSASPTGTWRCMGYVYNRDSTNGDSAS 956
PTP92   AVLDTSAPAASIAPGTIMDSSKLFYSSCDSTYRSSASPTGTWRCMGYVYNRDSTNGDSAS 956
NH-4    AVLDTSAPAASIAPGTIMDSSKLFYSSCDSTYRSSARPTGTWRCMGYVYNRDSTNGDSAS 956
14-1    AVLDNAAPIATVQPGVVVDGSILIYSSCAANYNSGQRPAGTWRCMGYVVNRDANTPDSAT 956
PTP47   AVLDYAAPTATVRPGVVVDGSILIYSSCAANYNSGQRPAGTWRCMGYVVNRDANTPDSAT 956
SN      AVLDNAAPTATVQPGVVVDGSILIYSSCAANYNSGQRPAGTWRCMGYVVNRDANTPDSAT 956
        ** *  ;**  :::  **.:;*,*  *;***    :  :.*.   *;*********;  ***.     ***;

SPM-1   LFQRVT 964 (SEQ ID NO: 26)
F8      LFQRVT 964 (SEQ ID NO: 27)
PB1     LFQRVT 964 (SEQ ID NO: 28)
C36     LFQRVT 964 (SEQ ID NO: 29)
LBL3    LFQRVT 964 (SEQ ID NO: 30)
Phi33   LFQRVT 964 (SEQ ID NO: 31)
LMA2    LFQRVT 964 (SEQ ID NO: 32)
KPP12   LFQRVT 963 (SEQ ID NO: 33)
JG024   LFQRVT 962 (SEQ ID NO: 34)
PTP92   LFQRVT 962 (SEQ ID NO: 35)
NH-4    LFQRVT 962 (SEQ ID NO: 36)
14-1    LFQRVT 962 (SEQ ID NO: 37)
PTP47   LFQRVT 962 (SEQ ID NO: 38)
SN      LFQRVT 962 (SEQ ID NO: 39)
        ******
```

MODIFYING BACTERIOPHAGE

The present invention relates to a method for modifying the genome of a lytic target phage, uses of the method and products thereof.

RELATED APPLICATIONS

This application is a 371 National Stage filing of International Application No. PCT/EP2015/073296, filed Oct. 8, 2015, which claims the benefit of GB Application No. 1417810.7, filed Oct. 8, 2014, each of which is hereby incorporated by reference in its entirety.

SEQUENCE LISTING

This application includes as part of its disclosure a biological sequence listing text file named "43297o2801.txt" having a size of 120,823 bytes that was created Apr. 6, 2017, which is hereby incorporated by reference in its entirety.

BACKGROUND TO THE INVENTION

Bacteriophage are the most abundant organisms in the world with an estimated $10^{30}$ present at any one time. Bacteriophage reportedly can inhabit every imaginable environment (Brabban et al., 2005), thus providing a huge reservoir of biological diversity for use in biotechnology. Phage have been used in a variety of applications, such as phage display to characterise protein-protein interactions (Smith and Petrenko, 1997), diagnostic tests for the rapid identification of bacterial pathogens (Dobozi-King et al., 2005), and in the treatment of bacterial infections by "phage therapy" (Harper et al., 2011). Another use of phage is as the basis for modification to make tailored gene delivery vehicles, which can be used for the delivery of genes encoding toxic proteins to target pathogenic bacteria. Such an approach is described in the SASPject system (WO2009/019293), in which bacteriophage are engineered to be non-lytic, thus ultimately non-viable, and to carry a SASP gene expression cassette, which is delivered into the targeted bacteria, which leads to rapid SASP expression. SASP are Small Acid-soluble Spore Proteins, which protect the DNA of Gram positive bacterial endospores during dormancy. However, upon expression of SASP in vegetative cells, rapid binding of SASP to the cell's DNA in a non-sequence specific manner (Nicholson et al., 1990) leads to rapid cell death.

Phage can be broadly split into temperate and non-temperate phage (Abedon, 2008). Temperate phage are able to exist in two distinct lifestyles. In one lifestyle, temperate phage replicate "lytically"—they infect the host cell, replicate and make new phage progeny, a process which ends in the lysis of the cell and the release of mature phage particles. In the other lifestyle, temperate phage infect the cell and integrate into the host cell genome, usually at specific attachment sites, to become "prophage". In so doing, they become a transient part of the host cell's genome, and are replicated together with the host cell's DNA. Integrated prophage are generally harmless to their host cell whilst in this integrated state, and can often provide selective advantage to the cell, by providing extra genes to the cell, e.g. CTX toxin genes are provided by CTX prophage to *Vibrio cholera*, increasing the virulence of such strains compared to non-toxin gene carrying strains (Waldor and Mekalanos, 1996). In contrast, non-temperate phage, otherwise known as "lytic" phage, are only able to replicate in the lytic lifestyle described above—they cannot integrate into host cell DNA and therefore never become part of the host cell genome: Henceforth such phages will be described as "obligately lytic" to distinguish them from temperate phage which are capable of both lytic and prophage replication.

When choosing phage for genetic modification, for instance when such phage are to act as delivery vectors for a gene encoding an anti-bacterial protein, such as SASP, the amenability of the phage to genetic modification is an important factor. Broadly speaking, temperate bacteriophage are easily genetically modified, providing that the bacterial host species can be manipulated by standard molecular genetic techniques involving recombination and resistance marker selection, or a recombineering system (Thomason et al., 2014).

Temperate phage, in the form of lysogens which carry integrated phage DNA as a prophage, can be engineered to carry exogenous DNA linked to any of a wide array of selectable markers, such as antibiotic or heavy metal resistance markers. Such markers may be linked to exogenous DNA and flanked by regions of prophage DNA, and cloned into suitable vectors which are not replicative (suicide vectors) in the bacterial host (lysogen). Upon introduction of such plasmids into the bacterial lysogen, by common methods such as conjugation or chemical or electro-transformation, recombinants which have integrated via the homologous sequences present on the plasmid, may be selected via the resistance marker linked to the exogenous DNA. Counter-selectable markers can also be used in engineering temperate phage. Recombinant phage which have retained the resistance marker can be screened by common methods such as PCR. Alternatively a counter-selectable marker, such as sacB, can be engineered into the backbone of the plasmid used for engineering such phage, and by selecting for the resistance marker linked to the exogenous DNA but against the counter-selectable marker, recombinant prophage can be isolated carrying only the exogenous DNA. The genotype can be confirmed by PCR. Such vectors are commonly available. Such engineered phage can be induced from the lysogenised strain, for example by the addition of Mitomycin C (Williamson et al., 2002) at which point the phage excise from the host chromosome and enter their lytic phase such that the retained marker can no longer be selected, but the marker and exogenous DNA remain in the phage genome.

Isolation of genetically manipulated lytic phage, however, cannot be achieved using the same methods described above. For example it is impossible to use conventional positive selection in order to isolate engineered obligately lytic phage, such as antibiotic and heavy metal resistance markers, which confer resistance to bacteria, cannot be selected due to the obligately lytic lifestyle of the phage. The DNA of the phage never becomes part of the host cell genome and therefore selectable resistance markers which convey resistance to the host are not selectable when located on obligately lytic phage.

Some techniques have been developed for the engineering of lytic phage. One such example is the BRED technique (Bacteriophage Recombineering of Electroporated DNA) (Marinelli et al., 2008), which uses a "recombineering" approach, and has been described for the engineering of *Mycobacterium* phage. Recombineering methods for the manipulation of bacterial genomes were first described in the λ Red system (Yu et al., 2000). In this technique the recombination proteins Exo and Beta catalyse the efficient recombination of linear DNA sequence introduced into host cell via transformation. The BRED approach similarly utilises recombination promoting proteins—the RecE/RecT-like proteins gp60 and gp61 from a *Mycobacterium* bacteriophage—to promote high levels of recombination when phage genomes are co-transformed with linear "targeting" DNA fragments into *M. smegmatis* cells. Recombinant phage are then screened and identified with relative ease due to the high efficiency of recombination. However, such an approach relies upon the development of an efficient recombineering system in the chosen bacterial species. Furthermore, phage genomes are large (Hendrix, 2009) and transformation of large DNA molecules is inefficient even in readily transformable bacteria such as *E. coli* (Sheng et al, 1995), and efficient transformation techniques have not been developed for many bacterial species.

Specific techniques have been developed for the engineering of certain bacteriophage. For instance a technique known as RIPh (Rho*-mediated inhibition of phage replication) has been developed for phage T4 (Pouillot et al., 2010). Early genes essential to phage replication are transcribed as concatenated run-through RNAs requiring the host transcription terminator factor Rho for the production of the early proteins. It was found that engineering *E. coli* to contain an inducer-controlled overexpressed mutated copy of Rho, called Rho*, inhibits production of the early T4 proteins and thus reversibly inhibits T4 phage replication, but has a minimal effect on host cell viability. In this state the T4 genome does not replicate and there is not continuation of the phage lifecycle through to mature phage synthesis and lysis, but it is not lost from the cell, and is a substrate for recombination. In the RIPh technique, the λ Red system is used to target recombination into the T4 genome whilst it is in this stable suspended state. Removal of the inducer allows the phage to continue its lifecycle and mature, engineered, phage are formed.

Another example of specific obligately lytic phage engineering systems is found in T7 phage. The *E. coli* genes trxA and cmk are required for the propogation of phage T7, but are not required for the growth of the host cell (Qimron et al, 2006; Mark, 1976). Therefore T7 could be engineered to carry either of these "marker" genes, by selecting recombinant phage on engineered host cells that lack the marker genes. However, in both the T4 and T7 example, quite specific and detailed knowledge of the phage's replication machinery, or the host cell genes specifically required for phage replication, is required.

It would be desirable to have a technique for modifying the genome of lytic phage which does not rely upon specific detailed knowledge of the genes involved in the replication pathway of the phage or the genes of the host cell required for phage propagation in the cell. It would further be desirable for such a technique to be broadly applicable to phage from any bacterial species.

SUMMARY OF THE INVENTION

The present invention provides a method for modifying the genome of a lytic target phage, wherein the target phage genome includes a first target sequence and a second target sequence, which method comprises:

(a) providing a vector which contains a phage-targeting region comprising a host range determinant of a marker phage, different from the host range determinant of the target phage, wherein the phage-targeting region is flanked by first and second flanking sequences homologous to the first and second target sequences of the target phage genome;

(b) introducing the vector into a first host cell, which host cell is a host for the target phage;

(c) infecting the first host cell with the target phage;

(d) allowing replication and recombination of phage to take place whereby the genome of the target phage is modified;

(e) propagating resultant phage on a second host cell, which host cell is a host for the marker phage and not the target phage; and harvesting the resultant phage.

It has surprisingly been found that a host range determinant of a phage can be used as a selectable marker to modify the genome of a related phage. We term this technique HOst Range Determinant Selection (HORDS). This invention is particularly useful for the genetic modification of obligately lytic phage which cannot form lysogens, as it provides a means of genetic selection that is not reliant upon selecting characteristics of the host cell, and instead selects for a characteristic inherited by the phage in its lytic state.

This technique does not rely upon specific detailed knowledge of the genes involved in the phage's replication pathway and/or the host cell gene(s) required for phage propagation in the cell, therefore not requiring undue experimentation on the phage prior to manipulation. Furthermore, this technique is broadly applicable to phage from any bacterial species. This technique requires the identification of factors from the phage which dictate its host range, together with factors from related phage. This can be readily performed by those skilled in the art, as directed by this application.

The genome of the lytic target phage may be modified by incorporation of an exogenous DNA sequence therein, by incorporation of a mutation such as a point mutation, or by creating a deletion. Combinations of these modifications may also be made.

Because the first and second flanking sequences of the phage targeting region are homologous to the first and second target sequences of the target phage genome, once the first host cell contains both the vector and the target phage, the phage can replicate and recombination can take place at the pairs of sequences, homologous with one another. Following recombination, only those resultant phage carrying the host range determinant of the marker phage may propagate in the second host cell. This enables selection of desired resultant phage containing the marker phage host range determinant.

The first and second target sequences of the target phage genome may be contiguous or non-contiguous. In one arrangement, the first and second target sequences of the target phage general are non-contiguous. According to this arrangement, where a recombination event occurs between the first and second flanking sequences and the first and second target sequences the region of DNA between the first and second target sequences is excised from the target phage genome resulting in a deletion. Advantageously, where the first and second target sequences of the target phage genome flank a phage gene or part thereof, such deletion results in inactivation of the gene following recombination. In one arrangement the phage gene is a lysis gene such as an endolysin. In this way the lytic target phage can be rendered non-lytic.

Where modification of the genome of the lytic target phage involves incorporation of an exogenous DNA sequence, the phage-targeting region of the vector further comprises an exogenous DNA sequence for incorporation into the genome of the target phage. Because the exogenous DNA sequence and the host range determinant of the marker phage both fall within the first and second flanking sequences of the phage-targeting region, recombination of the phage to select for the host range determinant will result in incorporation of the exogenous DNA sequence in the resultant phage. According to this arrangement, the first and second target sequences of the target phage genome may be contiguous or non-contiguous. Where they are non-contiguous, incorporation of the exogenous DNA sequence will simultaneously result in deletion of a region of the genome. Where the first and second target sequences are positioned in a phage gene or where they flank a phage gene or part thereof, incorporation of the exogenous DNA sequence will simultaneously result in inactivation of the gene following recombination.

Where a mutation, such as a point mutation is needed to be incorporated into the lytic target phage, at least one of the first and second flanking sequences in the phage-targeting region would contain the mutation as compared with the first and second target sequences of the target phage genome. Upon replication and recombination of the phage the genome of the target phage would be modified so as to incorporate the mutation. In this way, phage would be isolated carrying the host range determinant of the marker phage, and could be screened for the presence of the mutation.

As described above, introduction of such mutations could be combined with the incorporation of exogenous DNA sequence optionally together with a deletion in the target phage.

Typically the vector which contains the phage-targeting region is a plasmid. Such vectors are capable of replication in the first host cell.

According to the present invention the host range determinant of the marker phage typically encodes a baseplate protein, or tail fibre protein, or region thereof. Generally, in the case of tail fibre proteins, each comprises a C-terminal receptor binding region for binding to the target bacteria and an N-terminal region linking the C-terminal receptor binding region to the body of the bacteriophage. In one arrangement, taking Phi33 and related phage as an example, the N-terminal region comprises amino acids 1 to 628 of the tail fibre protein and the C-terminal region comprises the amino acids 629 to 964 of the tail fibre protein.

The C-terminal region may have no more than 96% amino acid sequence identity with the C-terminal region of bacteriophage Phi33 and may be from any one of the bacteriophage Phi33, LBL3, SPM-1, F8, PB1, KPP12, LMA2, SN, 14-1, JG024, NH-4, PTP47, C36, PTP92 and PTP93. Lower amino acid sequence identities in the C-terminal region are preferred. Advantageously the sequence identity is less than 90%, more advantageously less than 80%, preferably less than 70%, more preferably less than 60%, still more preferably less than 50%, particularly preferably less than 40%, more particularly preferably less than 30%. The N-terminal region may have at least 90% and advantageously at least 95% amino acid sequence identity with the N-terminal region of bacteriophage Phi33 and may be from any one of bacteriophage Phi33, LBL3, SPM-1, F8, PB1, KPP12, LMA2, SN, 14-1, JG024, NH-4, PTP47, C36, PTP92 and PTP93. Typically, each tail fibre protein has more than 80% amino acid sequence identity with the tail fibre amino acid sequence of bacteriophage Phi33, advantageously greater than 85%, preferably greater than 90% and more preferably greater than 95% sequence identity therewith. The N-terminal region and the C-terminal region may be from the same bacteriophage to provide a homologous tail fibre protein. Alternatively, the N-terminal region and the C-terminal region may be from different bacteriophage tail fibre proteins to provide a heterologous tail fibre protein. In one arrangement where the phage tail fibre protein is homologous, each tail fibre protein is from a bacteriophage selected from Phi33, LBL3, SPM-1, F8, PB1, KPP12, LMA2, SN, 14-1, JG024, NH-4, PTP47, C36, PTP92 and PTP93.

In one arrangement, this invention may be used to modify obligately lytic bacteriophage. In another arrangement, the invention may be used to modify a temperate phage, during lytic growth.

In a further arrangement, this invention is particularly useful in the engineering of obligately lytic bacteriophage for use as gene delivery vehicles. In a preferred arrangement, this invention could be used to modify lytic phage to carry a gene for an antibacterial protein.

As an alternative to conventional antibiotics, one family of proteins which demonstrate broad spectrum antibacterial activity inside bacteria comprises the α/β-type small acid-soluble spore proteins (known henceforth as SASP). Inside bacteria, SASP bind to the bacterial DNA: visualisation of this process, using cryoelectron microscopy, has shown that SspC, the most studied SASP, coats the DNA and forms protruding domains and modifies the DNA structure (Francesconi et al., 1988; Frenkiel-Krispin et al., 2004) from B-like (pitch 3.4 nm) towards A-like (3.18 nm; A-like DNA has a pitch of 2.8 nm). The protruding SspC motifs interact with adjacent DNA-SspC filaments packing the filaments into a tight assembly of nucleo-protein helices. In 2008, Lee et al. reported the crystal structure at 2.1 Å resolution of an α/β-type SASP bound to a 10-bp DNA duplex. In the complex, the α/β-type SASP adopt a helix-turn-helix motif, interact with DNA through minor groove contacts, bind to approximately 6 bp of DNA as a dimer and the DNA is in an A-B type conformation. In this way DNA replication is halted and, where bound, SASP prevent DNA transcription. SASP bind to DNA in a non-sequence specific manner (Nicholson et al., 1990) so that mutations in the bacterial DNA do not affect the binding of SASP. Sequences of a/B-type SASP may be found in appendix 1 of WO02/40678, including SASP-C from *Bacillus megaterium* which is the preferred α/ß-type SASP. WO02/40678 describes the use as an antimicrobial agent of bacteriophage modified to incorporate a SASP gene.

Bacteriophage vectors modified to contain a SASP gene have generally been named SASPject vectors. Once the SASP gene has been delivered to a target bacterium, SASP is produced inside those bacteria where it binds to bacterial DNA and changes the conformation of the DNA from B-like towards A-like. Production of sufficient SASP inside target bacterial cells causes a drop in viability of affected cells.

In particularly preferred embodiments, the method of the present invention may be used to engineer a SASP expression cassette into a phage to create a SASPject vector; this technique could also be used to engineer a SASP expression cassette into a phage and simultaneously delete a lytic gene to create a SASPject vector.

Accordingly, in one arrangement according to the invention, the exogenous DNA comprises a gene encoding an α/β small acid-soluble spore protein (SASP). In this way, the method of the invention may be used to produce a modified bacteriophage capable of infecting a plurality of different target bacteria. The modified bacteriophage includes a SASP which is toxic to the target bacteria, wherein the bacteriophage is typically non-lytic.

In one aspect, the term 'SASP' as used in the present specification refers to a protein with α/β-type SASP activity, that is, the ability to bind to DNA and modify its structure from its B-like form towards its A-like form, and not only covers the proteins listed in appendix 1 of WO02/40678, but also any homologues thereof, as well as any other protein also having α/β-type SASP activity. In an alternative aspect, the term 'SASP' as used in the specification refers to any protein listed in appendix 1 of WO02/40678, or any homologue having at least 70%, 75%, 80%, 85%, 90%, 92%, 94%, 95%, 96%, 98% or 99% sequence identity with any one of the proteins listed in appendix 1 of WO02/40678. In another alternative aspect, the term 'SASP' as used in the specification refers to any protein listed in appendix 1 of WO02/40678.

The SASP gene may be chosen from any one of the genes encoding the SASP disclosed in Appendix 1 of WO02/40678. In a preferred arrangement the SASP is SASP-C. The SASP-C may be from *Bacillus megaterium*.

It is preferred that the SASP gene is under the control of a constitutive promoter which is advantageously sufficiently strong to drive production of toxic levels of SASP when the modified bacteriophage is present in multiple copies in the target bacterium. Useful constitutive promoters include pdhA for pyruvate dehydrogenase E1 component alpha sub units, rpsB for the 30S ribosomal protein S2, pgi for glucose-6-phosphate isomerase and the fructose bisphosphate aldolase gene promoter fda. Preferred regulated promoters, active during infection, are lasB for elastase. These promoters are typically from *P. aeruginosa*. Promoters having a sequence showing at least 90% sequence identity to these promoter sequences may also be used.

Where the method of the invention is used to provide a modified bacteriophage, this may express a plurality of different host range determinants, wherein each host range determinant has a different bacterial host specificity. Alternatively, the modified bacteriophage, may express a hybrid host range determinant protein which comprises an amino acid sequence from a plurality of different bacteriophages. Each host range determinant may be a tail fibre protein. The bacterial host specificity of the host range determinants is advantageously within the same bacterial species.

In a further aspect, there is provided a composition for inhibiting or preventing bacterial cell growth, which comprises a modified bacteriophage or mixture thereof as defined herein and a carrier therefor. Such a composition may have a wide range of uses and is therefore to be formulated according to the intended use. The composition may be formulated as a medicament, especially for human treatment and may treat various conditions, including bacterial infections. Among those infections treatable according to the present invention are localised tissue and organ infections, or multi-organ infections, including blood-stream infections, topical infections, dental carries, respiratory infections, and eye infections. The carrier may be a pharmaceutically-acceptable recipient or diluent. The exact nature and quantities of the components of such compositions may be determined empirically and will depend in part upon the routes of administration of the composition.

Routes of administration to recipients include intravenous, intra-arterial, oral, buccal, sublingual, intranasal, by inhalation, topical (including ophthalmic), intra-muscular, subcutaneous and intra-articular. For convenience of use, dosages according to the invention will depend on the site and type of infection to be treated or prevented. Respiratory infections may be treated by inhalation administration and eye infections may be treated using eye drops. Oral hygiene products containing the modified bacteriophage are also provided; a mouthwash or toothpaste may be used which contains modified bacteriophage according to the invention formulated to eliminate bacteria associated with dental plaque formation.

A modified bacteriophage produced according to the invention may be used as a bacterial decontaminant, for example in the treatment of surface bacterial contamination as well as land remediation or water treatment. The bacteriophage may be used in the treatment of medical personnel and/or patients as a decontaminating agent, for example in a handwash.

Treatment of work surfaces and equipment is also provided, especially that used in hospital procedures or in food preparation. One particular embodiment comprises a composition formulated for topical use for preventing, eliminating or reducing carriage of bacteria and contamination from one individual to another. This is important to limit the transmission of microbial infections, particularly in a hospital environment where bacteria resistant to conventional antibiotics are prevalent. For such a use the modified bacteriophage may be contained in Tris buffered saline or phosphate buffered saline or may be formulated within a gel or cream. For multiple use a preservative may be added. Alternatively the product may be lyophilised and excipients, for example a sugar such as sucrose may be added.

DETAILED DESCRIPTION OF TECHNIQUE

In the present invention it has been found that multiple phage can be identified which carry homologous host range determinants. Such phage can be isolated. For instance, phage can be isolated which infect *Pseudomonas aeruginosa*, by screening for phage from environmental sources which are able to form plaques on *P. aeruginosa* strains (Gill and Hyman, 2010). Isolated phage may have their whole genomes sequenced and annotated. Alternatively DNA sequence databases could be searched for host range determinants. As of September 2014, there were 1400 phage genome sequences deposited in the National Centre for Biotechnology Information (NCBI) database.

HRD may be tail fibre proteins, which are commonly found to be proteins responsible for the initial recognition/binding to the host bacterium, for instance in phage T4, T5 and T7 (Rakhuba et al., 2010). Alternatively other HRD may be baseplate proteins. Phage genomes may be searched for potential HRD sequences by assessing the homology of all proteins in the phage genome to known sequences, using BLAST searches. It is advantageous to identify phage tail fibre proteins which are homologous. For example several phage Phi33, PTP47, PTP92 and C36—with a broad host range for *P. aeruginosa* strains, have been identified and their genomes sequenced. Analysis of the genome sequences of Phi33, PTP47, PTP92 and C36 reveals that they contain genes encoding putative tail fibre proteins with a high level of sequence identity (amino acid identity in parentheses): C36 (96%), PTP47 (86%), PTP92 (83%). BLAST searches have shown that these 4 phages are related to 10 other deposited phage genome sequences which, together, form the family of PB1-like phage: PB1, SPM1, F8, LBL3, KPP12, LMA2, SN, JG024, NH-4, 14-1 (Ceyssens et al., 2009). The homology of these putative tail fibre proteins was assessed. Following a 2 sequence BLAST alignment, compared to the Phi33 tail fibre protein (amino acid identity in parentheses): LBL3 (96%), SPM-1 (95%), F8 (95%), PB1 (95%), KPP12 (94%), LMA2 (94%), SN (87%), 14-1 (86%), JG024 (83%), NH-4 (83%). An alignment of all 14 of the aforementioned phage is shown in FIG. 6A-6E.

Analysis of the annotated tail fibre protein sequences from these 14 phages reveals that the N-terminal region of the proteins—equivalent to Phi33 tail fibre amino acids 1-628—show an even higher level of sequence identity at the amino acid level than the sequence identity of these proteins over their entire length, in the range of 96-100% for all 14 proteins. Following a 2 sequence BLAST alignment, compared to the N-terminal amino acids 1-628 of the Phi33 tail fibre protein (amino acid identity in parentheses): LBL3 (96%), SPM-1 (96%), F8 (96%), PB1 (96%), KPP12 (98%), LMA2 (99%), SN (99%), 14-1 (97%), JG024 (97%), NH-4 (97%), PTP47 (98%), C36 (96%), PTP92 (97%). However, the C-terminal region of the protein—equivalent to Phi33 tail fibre amino acids 629-964—is not as conserved as the N-terminal region in some of the proteins, the range of sequence identity being typically 57-96%. Following a 2 sequence BLAST alignment, compared to the C-terminal 629-964 amino acids of the Phi33 tail fibre protein (amino acid identity in parentheses): LBL3 (94%), SPM-1 (93%), F8 (93%), PB1 (94%), KPP12 (87%), LMA2 (85%), SN (65%), 14-1 (65%), JG024 (57%), NH-4 (57%), PTP47 (64%), C36 (96%), PTP92 (57%). Analysis of phage tail fibres from other, well characterised, phage has shown that they possess an N-terminal tail base plate binding region and a C-terminal receptor binding region (Veesler and Cambillau, 2011). In experimental analysis of their bacterial strain host range, using plaque assay or growth inhibition tests, the phage Phi33, PTP47, PTP92 and C36 have overlapping but non-identical host range (Table 1). Taken together with the established evidence for the role of the C-terminal region of phage tail fibres being involved in bacterial host receptor binding, and the sequence variation in the C-terminal region of these 4 phage, and their similar but non-identical host range, it is postulated that the C-terminal variation is associated with host range in the phage assessed.

It is further provided, according to this invention, that the genes for homologous tail fibre proteins can be taken from one phage and added to another, based upon their high level of sequence identity in the N-terminal region. The N-terminal region is thought to be involved in the binding of the tail fibre to the phage tail (Veesler and Cambillau, 2011), allowing the formation of viable phage with the host range associated with donor phage's tail fibre. Alternatively hybrid tail fibre genes may be made, carrying the conserved N-terminal tail attachment region of the tail fibre from a recipient phage, together with the variable C-terminal receptor-binding region from a heterologous donor phage tail fibre protein, using tail fibres genes such as those described herein. Such tail fibre hybrid genes could be used to replace some of the tail fibres of the phage. This provides an N-terminal region of the hybrid tail fibre (from the recipient phage) and allows the formation of viable phage with the host range associated with donor phage's tail fibre C-terminal receptor-binding region. Transplantation of engineered tail fibre hybrid genes into a recipient phage has been demonstrated in the present invention. Using standard molecular genetic techniques, Phi33 has been modified to carry heterologous tail fibre hybrids from the following phage: PTP92, PTP47, LBL3, SPM-1, F8, PB1, KPP12, LMA2, SN, 14-1, NH-4. All modified phage have been shown to be viable and able to plaque on P. aeruginosa. (The nomenclature of tail fibre hybrids is as follows: As an example, a hybrid gene such that the N-terminal tail attachment region of Phi33 is hybridised with the C-terminal receptor binding region of PTP47 is Phi33(N)PTP47(C).)

Phage Phi33 and PTP92 have a similar, but non-identical, host range. Therefore it was postulated that the host range of PTP92 could be inherited by Phi33, by replacement of the tail fibre gene in Phi33 (designated ORF32) with a hybrid Phi33(N)PTP92(C) tail fibre gene. The hybrid gene was made using the DNA sequence encoding the N-terminal region of Phi33 (equivalent to amino acids 1-628) and the C-terminal region of PTP92 (equivalent to amino acids 629-962), thus creating a hybrid tail fibre gene. The rationale for using these regions to create this hybrid gene is apparent from the earlier analysis of these proteins. The N-terminal regions of both tail fibre proteins, thought to be involved in phage attachment, are 97% identical; the C-terminal regions of both tail fibre proteins, thought to be involved in host cell receptor binding, are 57% identical. The hybrid tail fibre gene was flanked with Phi33 DNA, using ~1000 bp of sequence either side of Phi33 ORF32 (the native Phi33 tail fibre gene), and cloned into a plasmid. The plasmid was introduced into a P. aeruginosa strain susceptible to Phi33 infection and the resulting strain infected with Phi33, to produce a phage lysate. Within this lysate, recombinant phage would exist, which would carry the hybrid tail fibre rather than the Phi33 native tail fibre. The phage lysate was used to infect a strain which is able to plaque PTP92 but not Phi33. Therefore non-recombinant Phi33 phage would not be propagated on this host and would be selected against; Phi33 plaques carrying a recombinant Phi33-PTP92 hybrid tail fibre gene would be able to propagate and would be selected. Plaques were isolated and screened by PCR to assess their genotype. All of the plaques tested were found to carry the N-terminal region from Phi33 and the C-terminal region from PTP92, and thus the host range of PTP92 was transferred to Phi33.

Phi33 has been similarly modified to carry tail fibre hybrids (carrying the Phi33 N-terminal region) from the following phage: PTP92, PTP47, LBL3, SPM-1, F8, PB1, KPP12, LMA2, SN, 14-1, NH-4. All modified phage have been shown to be viable and able to plaque on P. aeruginosa.

BRIEF DESCRIPTION OF THE SEVERAL VIEWS OF THE DRAWINGS

This invention will now be described in further detail, by way of example only, and with reference to the accompanying drawings, in which:

FIG. 6A-6E shows multiple sequence alignment of the tail fibre genes of related phages. CLUSTAL 2.1 multiple sequence alignment of the tail fibre genes from Phage SPM-1, F8, PB1, C36, LBL3, Phi33, LMA2, KPP12, JG024, PTP92, NH-4, 14-1, PTP47, SN are shown.

Figure 1A:
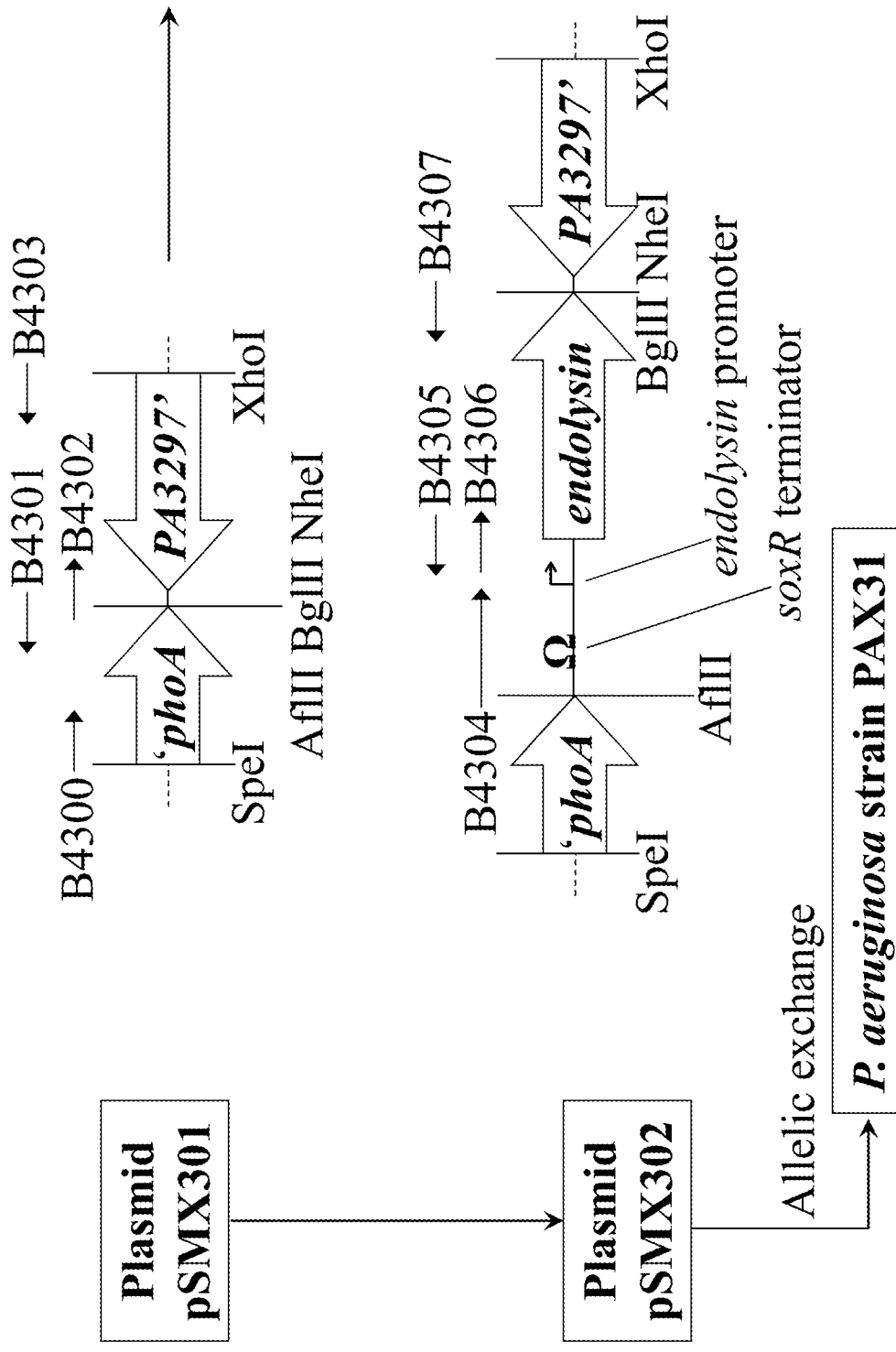
FIG. 1A-1B is a schematic diagram showing construction of plasmids containing lacZΔM15 and an endolysin gene.

Sequence divergent C-terminal region are shaded in grey, and the sequence conserved N-terminal region is unshaded.

DETAILED DESCRIPTION OF THE INVENTION

The following examples are given to show the utility of the HORDS technique in adding exogenous DNA to an obligately lytic phage.

As an example, a DNA region comprising the tail fibre gene, or section of a tail fibre gene, from an alternative phage, and the SASP-C gene from *Bacillus megaterium* controlled by a *Pseudomonas aeruginosa* fda promoter, may be cloned between two regions of Phi33 DNA that flank the native tail fibre region, or section thereof, in a broad host range *E. coli/P. aeruginosa* vector. This plasmid may be introduced into *P. aeruginosa*, and the resulting strain infected with Phi33. Following harvesting of progeny phage, double recombinant bacteriophage in which the native Phi33 tail fibre, or tail fibre section, has been replaced by the new tail fibre or tail fibre section, and to which the fda-SASP-C region of DNA has been introduced, may be isolated by plaquing on a suitable *P. aeruginosa* strain that is a host for the new, recombinant bacteriophage, but is not a host for Phi33.

As another example, for the construction of a Phi33 derivative in which two, unrelated sections of foreign DNA has been introduced into the genome, it is shown here as an example only, how the existing tail fibre, or section thereof, may be replaced by an alternative tail fibre or tail fibre section from a different bacteriophage, while simultaneously adding a SASP-C gene from *Bacillus megaterium* under the control of a *Pseudomonas aeruginosa* fda promoter, alongside a lacZα marker from *Escherichia coli*, via homologous recombination. A DNA region comprising the tail fibre gene, or section of a tail fibre gene, from an alternative phage, the SASP-C gene from *Bacillus megaterium* controlled by a *Pseudomonas aeruginosa* fda promoter, and an *Escherichia coli* lacZα reporter gene, may be cloned between two regions of Phi33 DNA that flank the native tail fibre region, or section thereof, in a broad host range *E. coli/P. aeruginosa* vector. This plasmid may be introduced into *P. aeruginosa*, and the resulting strain infected with Phi33. Following harvesting of progeny phage, double recombinant bacteriophage in which the native Phi33 tail fibre, or tail fibre section, has been replaced by the new tail fibre or tail fibre section, and to which the fda-SASP-C and lacZα regions have been introduced, may be isolated by plaquing on a suitable *P. aeruginosa* strain that is a host for the new, recombinant bacteriophage, but is not a host for Phi33. If visualisation of the lacZα marker is required, the *Pseudomonas aeruginosa* host strain used should carry the *Escherichia coli* lacZΔM15 allele at a suitable location in the host strain genome.

As another example, for construction of a Phi33 derivative in which a region of the bacteriophage genome is deleted, while simultaneously introducing a section of foreign DNA into the genome, it is shown here as an example only, how the existing tail fibre, or section thereof, may be replaced by an alternative tail fibre or tail fibre section from a different bacteriophage, while simultaneously deleting the native endolysin gene to render the phage non-lytic, and also simultaneously introducing a SASP-C gene from *Bacillus megaterium* under the control of a *Pseudomonas aeruginosa* fda promoter, via homologous recombination. Successful recombinants may be identified by selection of bacteriophage that plaque on a *P. aeruginosa* strain that is a host for the recombinant phage that carry the new host range determinant, but which is not a host for the original native phage, and which has also been modified such that the Phi33 endolysin gene is present on the *P. aeruginosa* genome.

A DNA region comprising the tail fibre gene, or section of a tail fibre gene, from an alternative phage, and the SASP-C gene from *Bacillus megaterium* controlled by a *Pseudomonas aeruginosa* fda promoter, may be cloned between two regions of Phi33 DNA that flank the native tail fibre region and endolysin region, or section thereof, in a broad host range *E. coli/P. aeruginosa* vector. This plasmid may be introduced into *P. aeruginosa*, and the resulting strain infected with Phi33. Following harvesting of progeny phage, double recombinant bacteriophage in which the native Phi33 tail fibre, or tail fibre section, has been replaced by the new tail fibre or tail fibre section, and to which the fda-SASP-C region of DNA has been introduced, and from which the native endolysin gene has been deleted, may be isolated by plaquing on a suitable *P. aeruginosa* (endolysin$^+$) strain that is a host for the new, recombinant bacteriophage, but is not a host for Phi33.

In order to generate a non-lytic version of a lytic bacteriophage by this method, a suitable *Pseudomonas aeruginosa* host strain is required that is a host for the recombinant bacteriophage that carries the new host range determinant, but that is not a host for the native bacteriophage, but in addition, carries the bacteriophage endolysin gene at a suitable location in the *Pseudomonas aeruginosa* genome. Similarly, if visualisation of a bacteriophage-bourne lacZα reporter is required, a *Pseudomonas aeruginosa* host strain is required that is a host for the recombinant bacteriophage that carries the new host range determinant, but that is not a host for the native bacteriophage, but in addition, carries the *Escherichia coli* lacZΔM15 allele at a suitable location. The genomic location for insertion of transgenes such as these should be chosen such that no essential genes are affected and no unwanted phenotypes are generated as a result of polar effects on the expression of adjacent genes. As an example, one such a location could include immediately downstream of the phoA gene of *Pseudomonas aeruginosa*.

As an example, the Phi33 endolysin gene may be cloned into an *E. coli* vector that is unable to replicate in *P. aeruginosa*, between two regions of *P. aeruginosa* strain PAO1 genomic DNA that flank the 3' end of phoA. This plasmid may be introduced into *P. aeruginosa* and isolates having undergone a single homologous recombination to integrate the whole plasmid into the genome selected according to the acquisition of tetracycline (50 µg/ml) resistance. Isolates (endolysin$^+$, lacZΔM15$^+$) which have undergone a second homologous recombination event may then be isolated on medium containing 10% sucrose (utilising the sacB counter-selectable marker present on the plasmid backbone).

As an example, the *Escherichia coli* lacZΔM15 allele may be cloned into an *E. coli* vector that is unable to replicate in *P. aeruginosa*, between two regions of *P. aeruginosa* strain PAO1 genomic DNA that flank the 3' end of phoA. This plasmid may be introduced into *P. aeruginosa* and isolates having undergone a single homologous recombination to integrate the whole plasmid into the genome selected according to the acquisition of tetracycline (50 µg/ml) resistance. Isolates (endolysin$^+$, lacZΔM15$^+$) which have undergone a second homologous recombination event may then be isolated on medium containing 10% sucrose (utilising the sacB counter-selectable marker present on the plasmid backbone).

Experimental Procedures

PCR reactions to generate DNA for cloning purposes may be carried out using Herculase II Fusion DNA polymerase (Agilent Technologies), depending upon the melting temperatures ($T_m$) of the primers, according to manufacturers instructions. PCR reactions for screening purposes may be carried out using Taq DNA polymerase (NEB), depending upon the $T_m$ of the primers, according to manufacturers instructions. Unless otherwise stated, general molecular biology techniques, such as restriction enzyme digestion, agarose gel electrophoresis, T4 DNA ligase-dependent ligations, competent cell preparation and transformation may be based upon methods described in Sambrook et al., (1989). Enzymes may be purchased from New England Biolabs or Thermo Scientific. DNA may be purified from enzyme reactions and prepared from cells using Qiagen DNA purification kits. Plasmids may be transferred from E. coli strains to P. aeruginosa strains by conjugation, mediated by the conjugation helper strain E. coli HB101 (pRK2013). A chromogenic substrate for (3-galactosidase, S-gal, that upon digestion by β-galactosidase forms a black precipitate when chelated with ferric iron, may be purchased from Sigma (S9811).

Primers may be obtained from Sigma Life Science. Where primers include recognition sequences for restriction enzymes, additional 2-6 nucleotides may be added at the 5' end to ensure digestion of the PCR-amplified DNA.

All clonings, unless otherwise stated, may be achieved by ligating DNAs overnight with T4 DNA ligase and then transforming them into E. coli cloning strains, such as DH5α or TOP10, with isolation on selective medium, as described elsewhere (Sambrook et al., 1989).

An E. coli/P. aeruginosa broad host range vector, such as pSM1080, may be used to transfer genes between E. coli and P. aeruginosa. pSM1080 was previously produced by combining a broad host-range origin of replication to allow replication in P. aeruginosa, oriT from pRK2, the tetAR selectable marker for use in both E. coli and P. aeruginosa, from plasmid pRK415, and the high-copy-number, E. coli origin of replication, oriV, from plasmid pUC19.

An E. coli vector that is unable to replicate in P. aeruginosa, pSM1104, may be used to generate P. aeruginosa mutants by allelic exchange. pSM1104 was previously produced by combining oriT from pRK2, the tetAR selectable marker for use in both E. coli and P. aeruginosa, from plasmid pRK415, the high-copy-number, E. coli origin of replication, oriV, from plasmid pUC19, and the sacB gene from Bacillus subtilis strain 168, under the control of a strong promoter, for use as a counter-selectable marker.

Construction of Plasmids to Generate Pseudomonas aeruginosa Strains Carrying Either the Phi33 Endolysin Gene, or the Escherichia coli lacZΔM15 Gene, Immediately Downstream of the phoA Locus of the Bacterial Genome 1. Plasmid pSMX301 (FIG. 1A-1B), comprising pSM1104 carrying DNA flanking the 3' end of the P. aeruginosa PAO1 phoA homologue, may be constructed as follows.

Figure 1B:
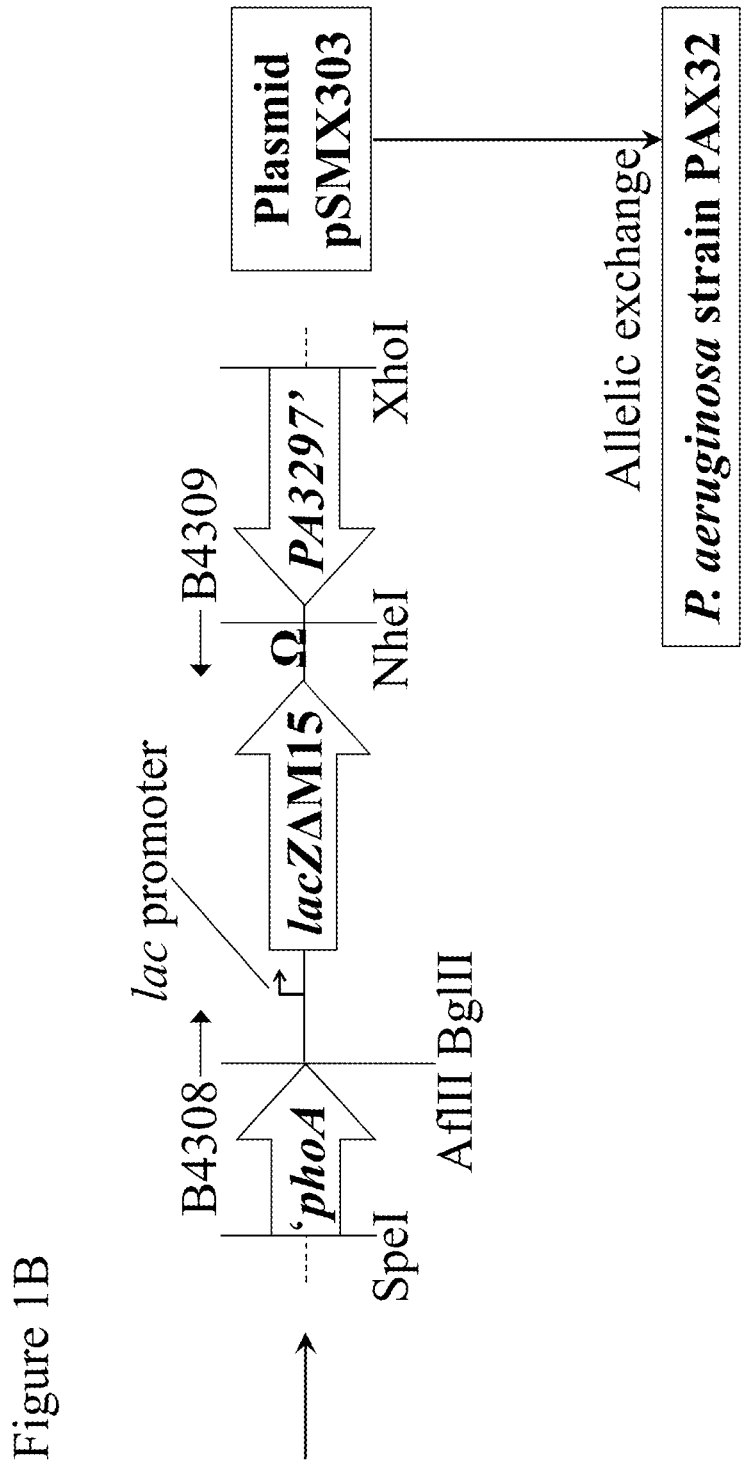
Figure 2A:
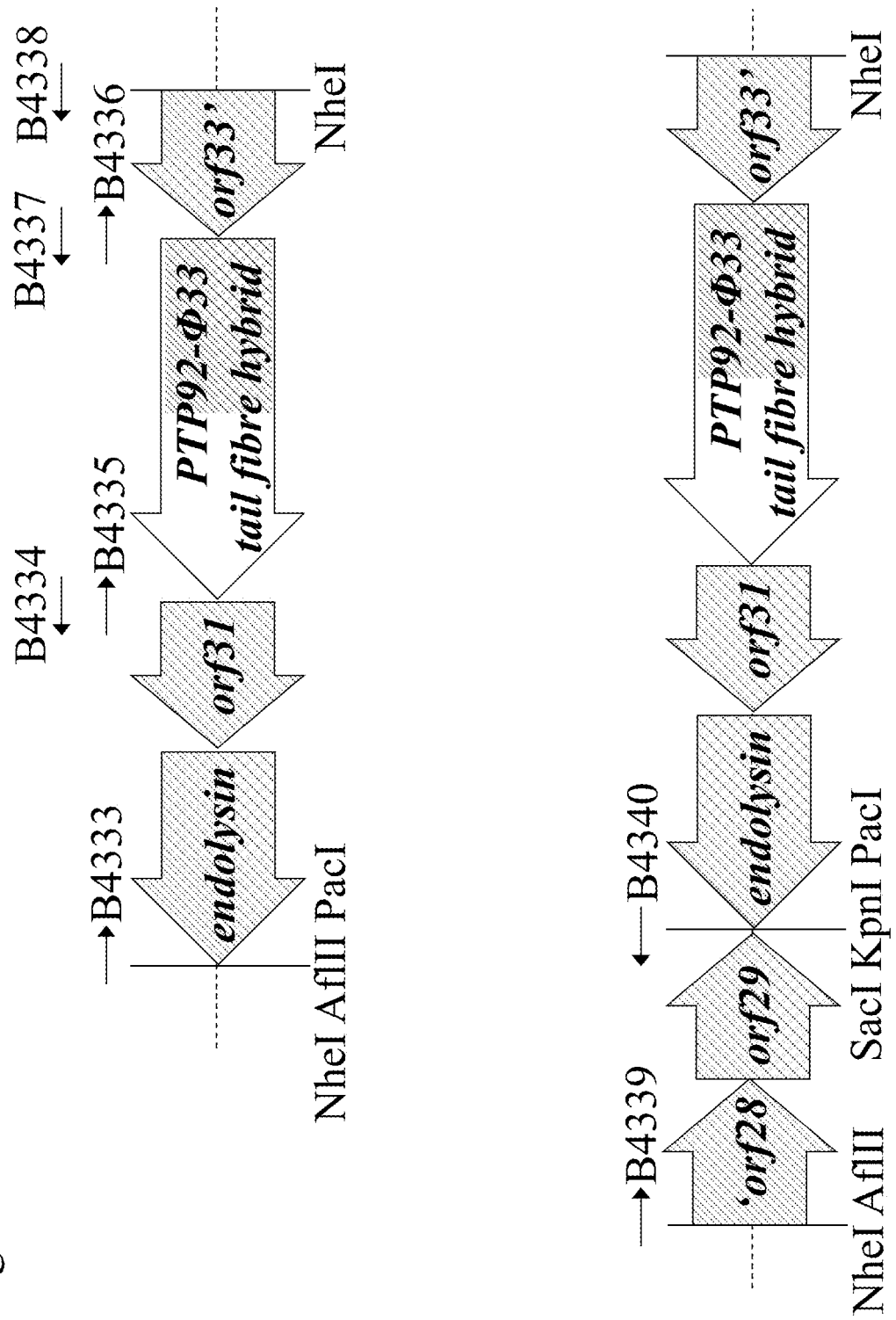
FIG. 2A-2D is a schematic diagram showing construction of plasmids with replaced tail fibre sections, for the genetic modification of phage to add SASP-C, or SASP-C in addition to a lacZα marker.
Figure 2B:
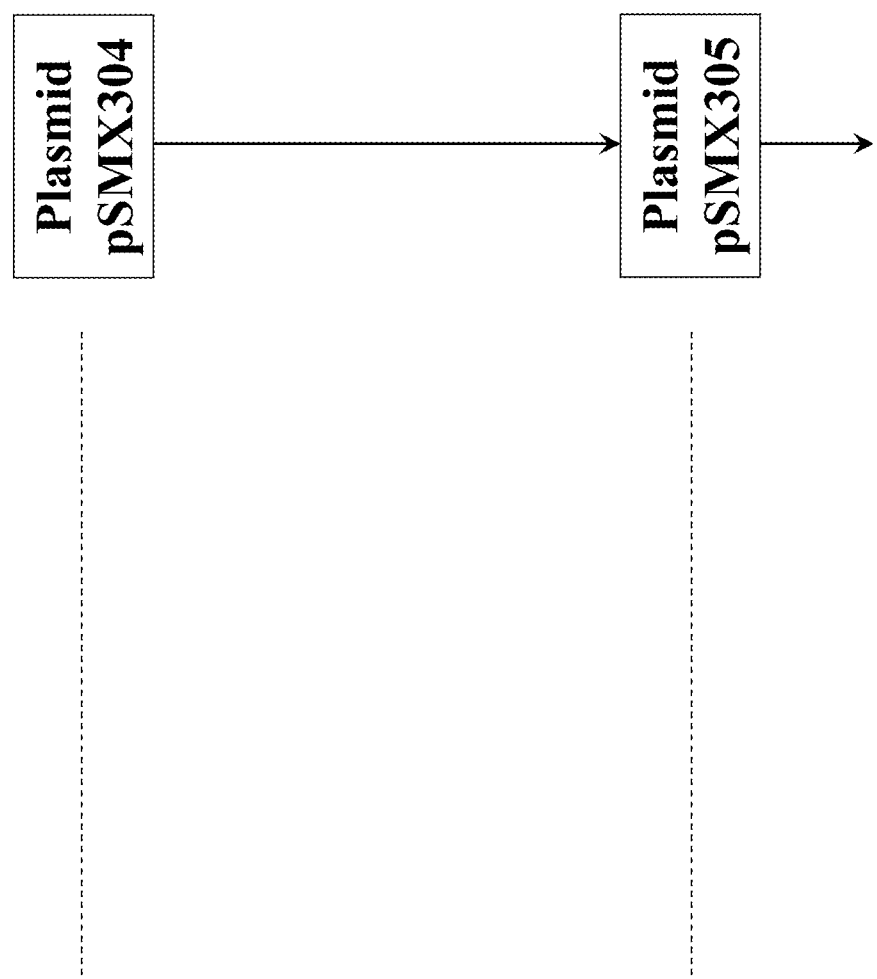
Figure 2C:
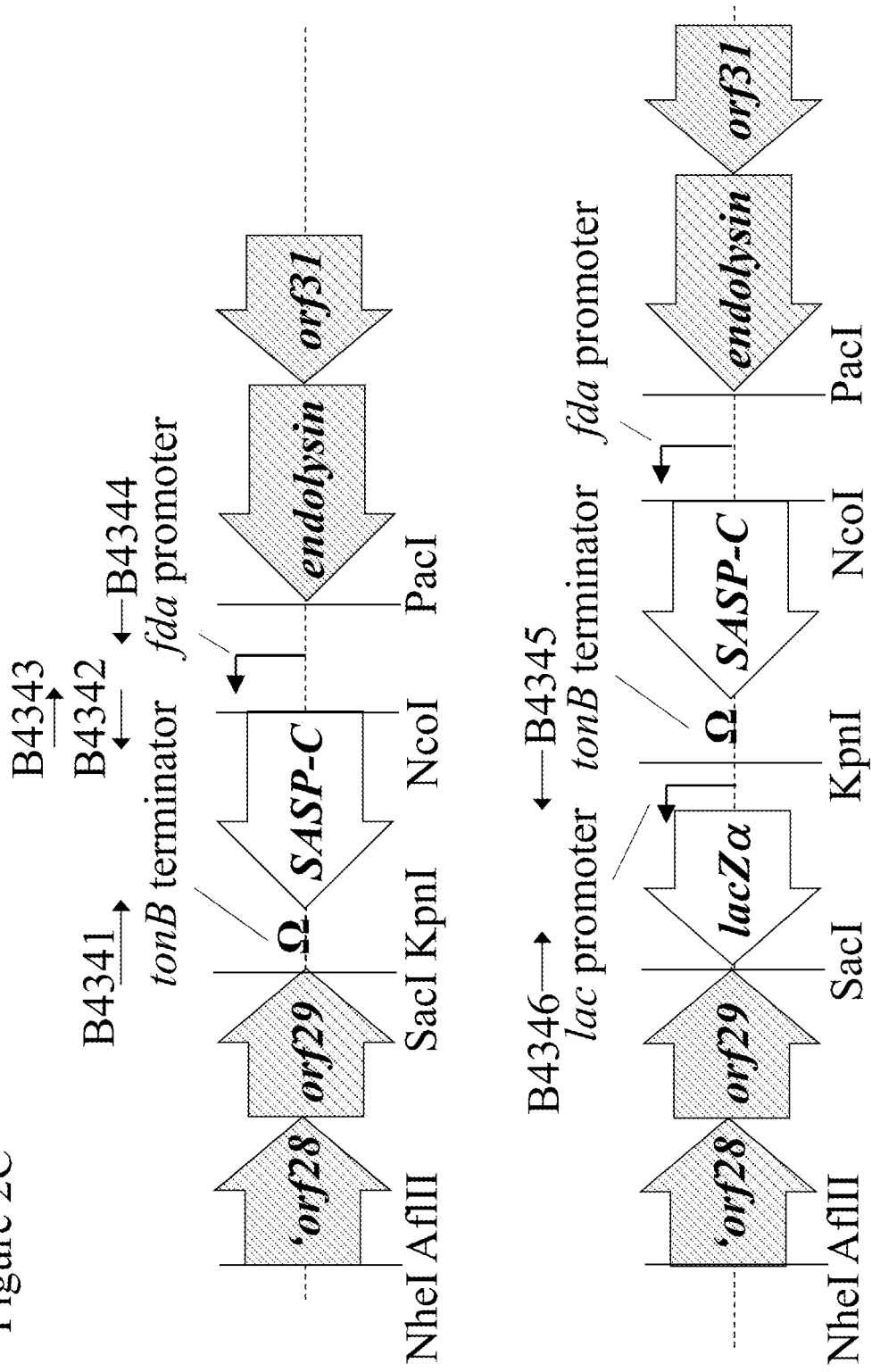
Figure 2D:
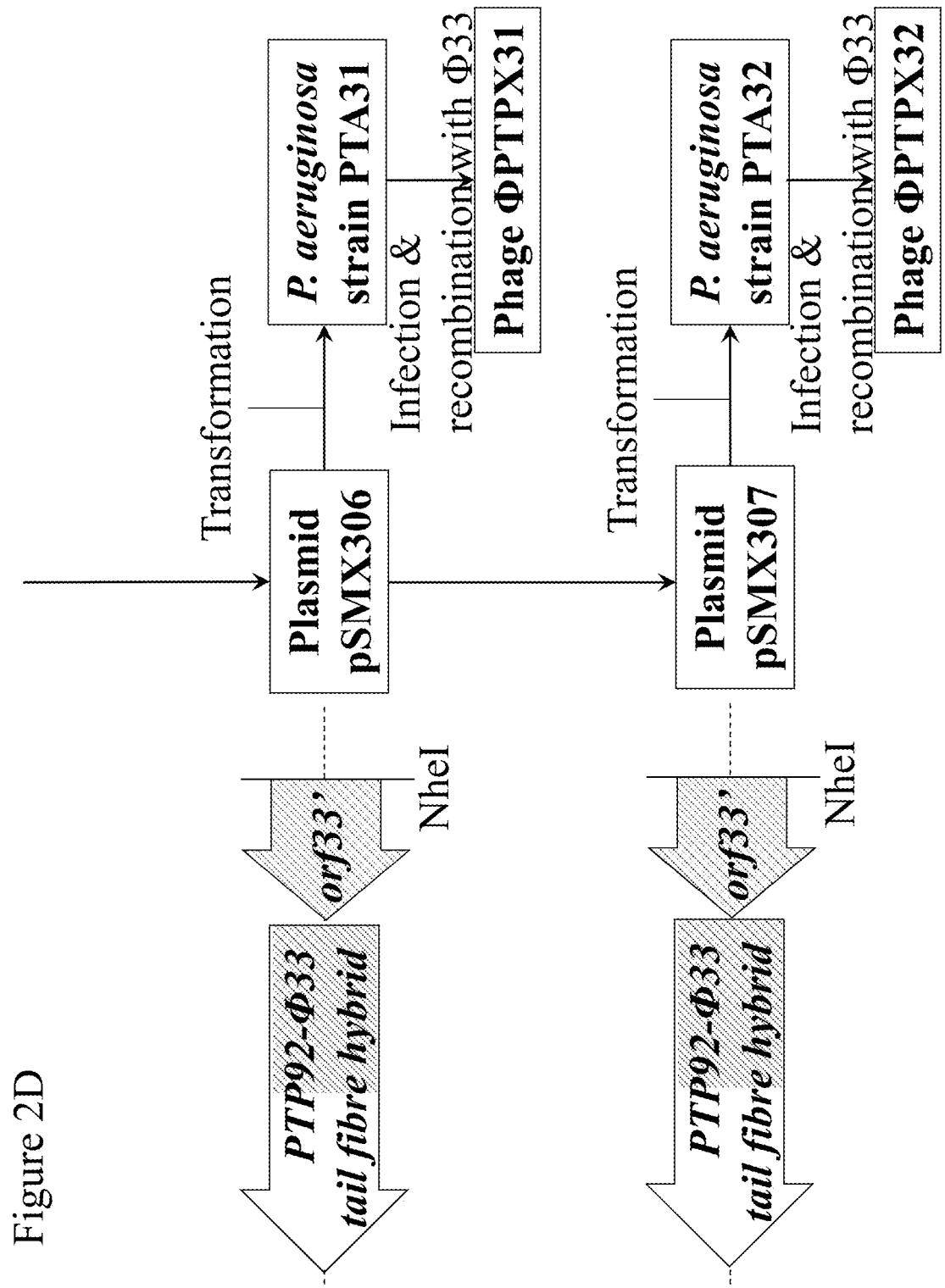

A region comprising the terminal approximately 1 kb of the phoA gene from P. aeruginosa may be amplified by PCR using primers B4300 and B4301 (FIG. 1A-1B). The PCR product may then be cleaned and digested with SpeI and BglII. A second region comprising approximately 1 kb downstream of the phoA gene from P. aeruginosa may be amplified by PCR using primers B4302 and B4303 (FIG. 1A-1B). This second PCR product may then be cleaned and digested with BglII and XhoI. The two digests may be cleaned again and ligated to pSM1104 that has been digested with SpeI and XhoI, in a 3-way ligation, to yield plasmid pSMX301 (FIG. 1A-1B).

Primer B4300 consists of a 5' SpeI restriction site (underlined), followed by sequence located approximately 1 kb upstream of the stop codon of phoA from P. aeruginosa strain PAO1 (FIG. 1A-1B). Primer B4301 consists of 5' BglII and AflII restriction sites (underlined), followed by sequence complementary to the end of the phoA gene from P. aeruginosa strain PAO1 (the stop codon is in lower case; FIG. 1A-1B). Primer B4302 consists of 5' BglII and NheI restriction sites (underlined), followed by sequence immediately downstream of the stop codon of the phoA gene from P. aeruginosa strain PAO1 (FIG. 1A-1B). Primer B4303 consists of a 5' XhoI restriction site (underlined), followed by sequence that is complementary to sequence approximately 1 kb downstream of the phoA gene from P. aeruginosa strain PAO1 (FIG. 1A-1B).

```
Primer B4300
                                           (SEQ ID NO: 1)
5'-GATAACTAGTCCTGGTCCACCGGGGTCAAG-3'

Primer B4301
                                           (SEQ ID NO: 2)
5'-GCTCAGATCTTCCTTAAGtcaGTCGCGCAGGTTCAG-3'

Primer B4302
                                           (SEQ ID NO: 3)
5'-AGGAAGATCTGAGCTAGCTCGGACCAGAACGAAAAAG-3'

Primer B4303
                                           (SEQ ID NO: 4)
5'-GATACTCGAGGCGGATGAACATTGAGGTG-3'
```

2. Plasmid pSMX302 (FIG. 1A-1B), comprising pSMX301 carrying the endolysin gene from Phi33, under the control of an endolysin gene promoter, may be constructed as follows.

The endolysin gene promoter may be amplified by PCR from Phi33 using primers B4304 and B4305 (FIG. 1A-1B). The endolysin gene itself may be amplified by PCR from Phi33 using primers B4306 and B4307 (FIG. 1A-1B). The two PCR products may then be joined together by Splicing by Overlap Extension (SOEing) PCR, using the two outer primers, B4304 and B4307. The resulting PCR product may then be digested with AflII and BglII, and ligated to pSMX301 that has also been digested with AflII and BglII, to yield plasmid pSMX302 (FIG. 1A-1B).

Primer B4304 consists of a 5' AflII restriction site (underlined), followed by a bi-directional transcriptional terminator (soxR terminator, 60-96 bases of Genbank accession number DQ058714), and sequence of the beginning of the endolysin promoter region (underlined, in bold) (FIG. 1A-1B). Primer B4305 consists of a 5' region of sequence that is complementary to the region overlapping the start codon of the endolysin gene from Phi33, followed by sequence that is complementary to the end of the endolysin promoter region (underlined, in bold; FIG. 1A-1B). Primer B4306 is the reverse complement of primer B4305 (see also FIG. 1A-1B). Primer B4307 consists of a 5' BglII restriction site (underlined), followed by sequence complementary to the end of the Phi33 endolysin gene (FIG. 1A-1B).

```
Primer B4304
                                           (SEQ ID NO: 5)
5'-GATACTTAAGAAAACAAACTAAAGCGCCCTTGTGGCGCTTTAGTTTT
ATACTACTGAGAAAAATCTGGATTC-3'
```

-continued

Primer B4305

(SEQ ID NO: 6)

5'-GATTTTCATCAATACTCCTGGATCCCGTTAATTCGAAGAGTCG-3'

Primer B4306

(SEQ ID NO: 7)

5'-CGACTCTTCGAATTAACGGGATCCAGGAGTATTGATG AAAATC-3'

Primer B4307

(SEQ ID NO: 8)

5'-GATA<u>AGATCTT</u>CAGGAGCCTTGATTGATC-3'

3. Plasmid pSMX303, comprising pSMX301 carrying lacZΔM15 under the control of a Lac promoter, may be constructed as follows.

The lacZΔM15 gene under the control of a lac promoter may be amplified by PCR from *Escherichia coli* strain DH10B using primers B4308 and B4309 (FIG. 1A-1B). The resulting PCR product may then be digested with BglII and NheI, and ligated to pSMX301 that has also been digested with BglII and NheI, to yield plasmid pSMX303 (FIG. 1A-1B).

Primer B4308 consists of a 5' BglII restriction site (underlined), followed by sequence of the lac promoter (FIG. 1A-1B). Primer B4309 consists of a 5' NheI restriction site (underlined), followed by a bi-directional transcriptional terminator and sequence complementary to the 3' end of lacZΔM15 (underlined, in bold; FIG. 1A-1B).

Primer B4308

(SEQ ID NO: 9)

5'-GATA<u>AGATCT</u>GAGCGCAACGCAATTAATGTG-3'

Primer B4309

(SEQ ID NO: 10)

5'-GATA<u>GCTAGC</u>AGTCAAAAGCCTCCGGTCGGAGGCTTTTGACTTTATT TTTGACACCAGACCAAC-3'

Genetic Modification of *Pseudomonas aeruginosa* to Introduce the Phi33 Endolysin Gene Immediately Downstream of the phoA Locus of the Bacterial Genome 1. Plasmid pSMX302 (FIG. 1A-1B) may be transferred to a suitable *P. aeruginosa* strain that is a host for bacteriophage carrying the new host range determinant, but which is not a host for the original bacteriophage, by conjugation, selecting for primary recombinants by acquisition of resistance to tetracycline (50 µg/ml).

2. Double recombinants may then be selected via sacB-mediated counter-selection, by plating onto medium containing 10% sucrose.

3. Isolates growing on 10% sucrose may then be screened by PCR to confirm that the Phi33 endolysin gene has been introduced downstream of the *P. aeruginosa* phoA gene.

4. Following verification of an isolate (PAX31), this strain may then be used as a host for further modification of bacteriophage, where complementation of an endolysin mutation is required.

Genetic Modification of *Pseudomonas aeruginosa* to Introduce the *Escherichia coli* lacZΔM15 Allele Immediately Downstream of the phoA Locus of the Bacterial Genome 1. Plasmid pSMX303 (FIG. 1A-1B) may be transferred to a suitable *P. aeruginosa* strain that is a host for bacteriophage carrying the new host range determinant, but which is not a host for the original bacteriophage, by conjugation, selecting for primary recombinants by acquisition of resistance to tetracycline (50 µg/ml).

2. Double recombinants may then be selected via sacB-mediated counter-selection, by plating onto medium containing 10% sucrose.

3. Isolates growing on 10% sucrose may then be screened by PCR to confirm that the *Escherichia coli* lacZΔM15 allele has been introduced downstream of the *P. aeruginosa* phoA gene.

4. Following verification of an isolate (PAX32), this strain may then be used as a bacteriophage host, when complementation of a lacZα reporter is desired.

Construction of a Plasmid to Introduce a New Section of DNA (Fda-SASP-C) into the Genome of Bacteriophage Phi33, Utilising an Alternative Host Range Determinant as a Selectable Marker.

1. Plasmid pSMX304 (FIG. 2A-2D), comprising pSM1080 carrying Phi33 sequences flanking sequences of the tail fibre host range determinant of the related bacteriophage PTP92, may be constructed as follows.

The region immediately downstream of the Phi33 tail fibre may be amplified by PCR using primers B4333 and B4334 (FIG. 2A-2D). The region encoding the C-terminal, receptor-binding region of the tail fibre of bacteriophage PTP92 may be amplified by PCR using primers B4335 and B4336 (FIG. 2A-2D). These two PCR products may then be joined by SOEing PCR using the outer primers B4333 and B4336. The region encoding the Phi33 tail fibre N-terminal region, and the region immediately upstream of the Phi33 tail fibre, may be amplified by PCR using primers B4337 and B4338 (FIG. 2A-2D). This Phi33 tail fibre region may then be joined to the PCR product comprising the region downstream of the Phi33 tail fibre and the PTP92 host range determinant, by SOEing PCR using the outer primers B4333 and B4338. The resulting PCR product may then be cleaned, digested with NheI, cleaned again and then ligated to pSM1080 that has been digested with NheI, treated with alkaline phosphatase and cleaned, prior to ligation. This construction yields plasmid pSMX304 (FIG. 2A-2D).

Primer B4333 consists of 5' NheI-AflII-PacI restriction sites (underlined) followed by sequence complementary to a region approximately 1 kb downstream of the Phi33 tail fibre (FIG. 2A-2D). Primer B4334 consists of 5' sequence of the end of the region encoding the C-terminal, receptor binding region of the PTP92 tail fibre, followed by sequence immediately downstream of the Phi33 tail fibre (underlined; FIG. 2A-2D). Primer B4335 is the reverse complement of primer B4334. Primer B4336 consists of 5' sequence complementary to a region that encodes part of the C-terminal, receptor binding region of the PTP92 tail fibre, followed by sequence complementary to the Phi33 tail fibre (underlined; FIG. 2A-2D). Primer B4337 is the reverse complement of primer B4336 (FIG. 2A-2D). Primer B4338 consists of a 5' NheI restriction site (underlined), followed by sequence of a region upstream of the Phi33 tail fibre (FIG. 2A-2D).

Primer B4333

(SEQ ID NO: 11)

5'-GATA<u>GCTAGCGA</u>CTTAAGGATTAATTAATCAGGAGCCTTGATTGAT C-3'

Primer B4334

(SEQ ID NO: 12)

5'-CTATTCCAGCGGGTAACGTAA<u>AATGAAATGGACGCGGATCAG</u>-3'

Primer B4335

(SEQ ID NO: 13)

5'-<u>CTGATCCGCGTCCATTTCATTT</u>TACGTTACCCGCTGGAATAG-3'

Primer B4336

(SEQ ID NO: 14)

5'-CTCAAGCGGGCCGGCTGGTCTCT<u>CGGCAATAACTCCTATGTGATCAC C</u>-3'

-continued

```
Primer B4337
                                        (SEQ ID NO: 15)
5'-GGTGATCACATAGGAGTTATTGCCGAGAGACCAGCCGGCCCGCTTGA
G-3'

Primer B4338
                                        (SEQ ID NO: 16)
5'-GATAGCTAGCGGAGTACCGCTTACGTCTC-3'
```

2. Plasmid pSMX305 (FIG. 2A-2D), comprising pSMX304 carrying a region of Phi33 DNA immediately downstream of the endolysin gene, the location chosen here for insertion of the fda-SASP-C foreign DNA, may be constructed as follows.

An approximately 1 kb region of Phi33 DNA located immediately downstream of the endolysin gene, the location chosen for insertion of the fda-SASP-C foreign DNA, may be amplified by PCR using primers B4339 and B4340 (FIG. 2A-2D). The resulting PCR product may then be digested with AflII and PacI, cleaned, and ligated to pSMX304 that has also been digested with AflII and PacI and cleaned, prior to ligation, yielding plasmid pSMX305 (FIG. 2A-2D).

Primer B4339 consists of a 5' AflII restriction site (underlined), followed by Phi33 sequence approximately 1 kb downstream of the location chosen here for insertion of the fda-SASP-C DNA (FIG. 2A-2D). Primer B4340 consists of 5' PacI-KpnI-SacI restriction sites (underlined), followed by sequence complementary to Phi33 sequence located immediately downstream of the location chosen for insertion of the fda-SASP-C DNA (FIG. 2A-2D).

```
Primer B4339
                                        (SEQ ID NO: 17)
5'-GATACTTAAGTCGCTCCAGCCATGCGGAAAAC-3'

Primer B4340
                                        (SEQ ID NO: 18)
5'-GATATTAATTAATCGGTACCTCGAGCTCTATTCGCCCAAAAGAAAA
G-3'
```

3. Plasmid pSMX306 (FIG. 2A-2D), comprising pSMX305 carrying fda-SASP-C, may be constructed as follows.

The SASP-C gene from *Bacillus megaterium* strain KM (ATCC 13632) may be amplified by PCR using primers B4341 and B4342 (FIG. 2A-2D). The resulting PCR product may then be cleaned, digested with KpnI and NcoI, and cleaned again. The *Pseudomonas aeruginosa* fda promoter may be amplified by PCR using primers B4343 and B4344 (FIG. 2A-2D). The resulting PCR product may then be cleaned, digested with NcoI and PacI, and cleaned again. The two PCR products may then be ligated, in a 3-way ligation, to pSMX305 that has been digested with KpnI and PacI and cleaned prior to ligation, to yield plasmid pSMX306 (FIG. 2A-2D).

Primer B4341 consists of a 5' KpnI restriction site (underlined), followed by a bi-directional transcription terminator (tonB terminator), followed by sequence complementary to the end of SASP-C from *Bacillus megaterium* strain KM (ATCC 13632) (underlined, in bold; FIG. 2A-2D). Primer B4342 (FIG. 2A-2D) consists of a 5' NcoI restriction site (underlined), followed by sequence of the beginning of the SASP-C gene from *Bacillus megaterium* strain KM (ATCC 13632). Primer B4343 consists of a 5' NcoI restriction site (underlined), followed by sequence of the fda promoter (FIG. 2A-2D). Primer B4344 consists of a 5' PacI restriction site (underlined), followed by sequence complementary to the fda promoter (FIG. 2A-2D).

```
B4341
                                        (SEQ ID NO: 19)
5'-GATAGGTACCAGTCAAAAGCCTCCGACCGGAGGCTTTTGACTTTAGT
ACTTGCCGCCTAG-3'

B4342
                                        (SEQ ID NO: 20)
5'-GATACCATGGCAAATTATCAAAACGCATC-3'

B4343
                                        (SEQ ID NO: 21)
5'-GATACCATGGTTCTCGTATCTCCCAATC-3'

B4344
                                        (SEQ ID NO: 22)
5'-GATATTAATTAACGACGAAGGCCTGGTG-3'
```

Genetic Modification of Phi33 to Add Fda-SASP-C to the Bacteriophage Genome, the PTP92 Host Range Determinant as a Means of Selection 1. Plasmid pSMX306 (FIG. 2A-2D) may be introduced into a *P. aeruginosa* strain that is a host for both the original, and the host range determinant donor phage, by conjugation, selecting transconjugants on the basis of tetracycline resistance (50 μg/ml), yielding strain PTA31.

2. Strain PTA31 may be infected with phage Phi33, and the progeny phage harvested.

3. Recombinant phage, in which the PTP92 host range determinant has been transferred to Phi33, may be identified by plaquing the lysate from step (2) on *P. aeruginosa* strain 2726, which is a host for the recombinant phage that carries the PTP92 host range determinant, but which is not a host for the parental bacteriophage Phi33.

4. A PCR screen may be further carried out to identify isolates that have simultaneously acquired fda-SASP-C, in addition to the host range determinant from PTP92.

5. Following identification of a verified isolate (PTPX31; FIG. 2A-2D; FIG. 3A-3B), this isolate may be plaque purified twice more, prior to further use.

Construction of a Plasmid to Introduce Two New Sections of DNA (Fda-SASP-C and lacZα) into the Genome of Bacteriophage Phi33, Utilising an Alternative Host Range Determinant as a Selectable Marker.

1. Plasmid pSMX307 (FIG. 2A-2D), comprising pSMX306 carrying the lacZα reporter from plasmid pUC19, may be constructed as follows.

The lacZα reporter may be amplified by PCR from pUC19 using primers B4345 and B4346 (FIG. 2A-2D). The resulting PCR product may then be cleaned, digested with SacI and KpnI, cleaned again, and ligated to pSMX306 that has been digested with SacI and KpnI and cleaned prior to ligation, to yield plasmid pSMX307 (FIG. 2A-2D).

Primer B4345 consists of a 5' SacI restriction site (underlined), followed by sequence complementary to the 3' end of lacZα (FIG. 2A-2D). Primer B4346 consists of a 5' KpnI restriction site (underlined), followed by sequence of the lac promoter (FIG. 2A-2D).

```
Primer B4345
                                        (SEQ ID NO: 23)
5'-GATAGAGCTCTTAGCGCCATTCGCCATTC-3'

Primer B4346
                                        (SEQ ID NO: 24)
5'-GATAGGTACCGCGCAACGCAATTAATGTG-3'
```

Figure 3A:
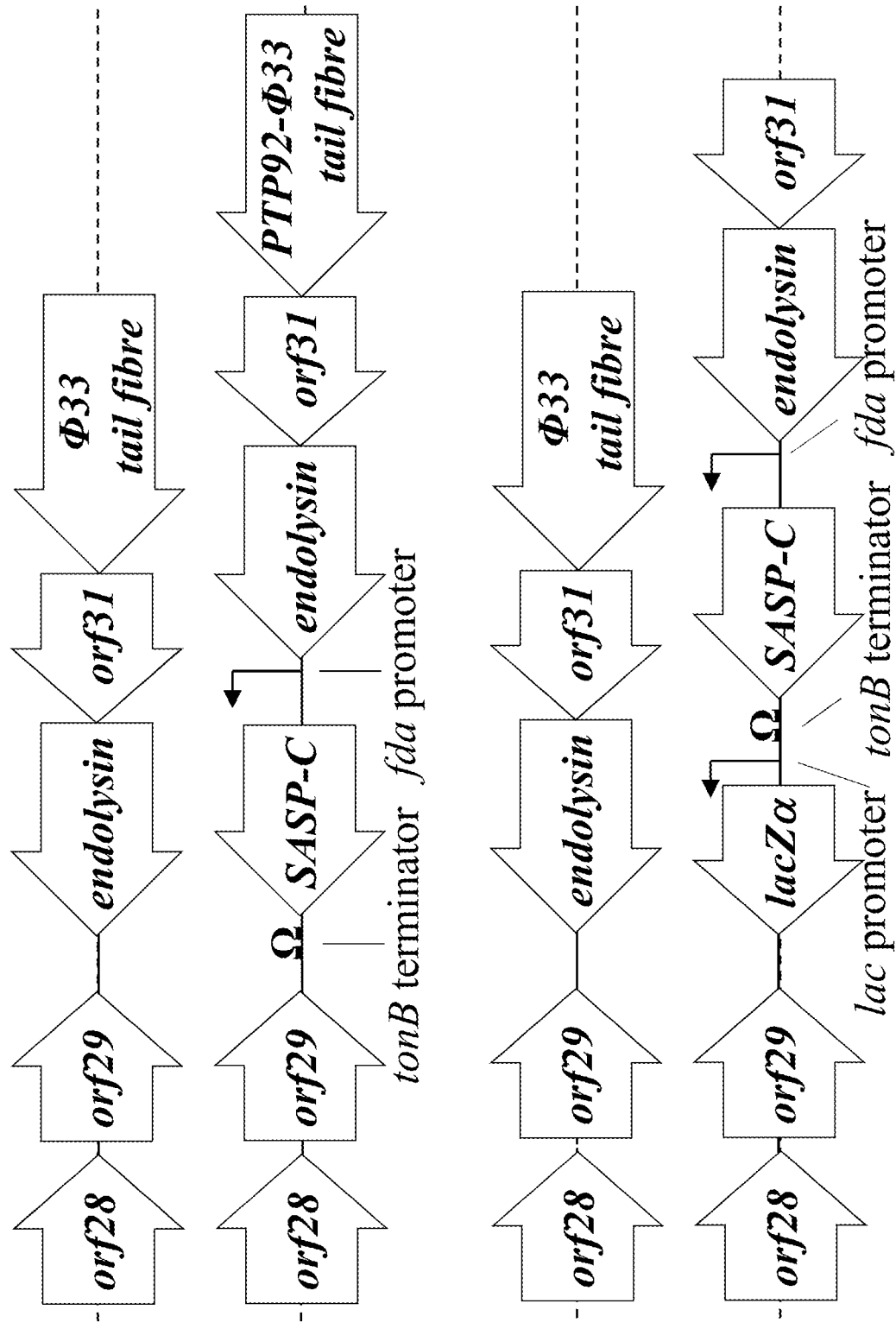
FIG. 3A-3B is a schematic diagram showing production of phage in which SASP-C, or SASP-C in addition to a lacZα marker, have been added to the phage, by recombination, using HORDS as a means of selecting for recombinant phage.
Figure 3B:
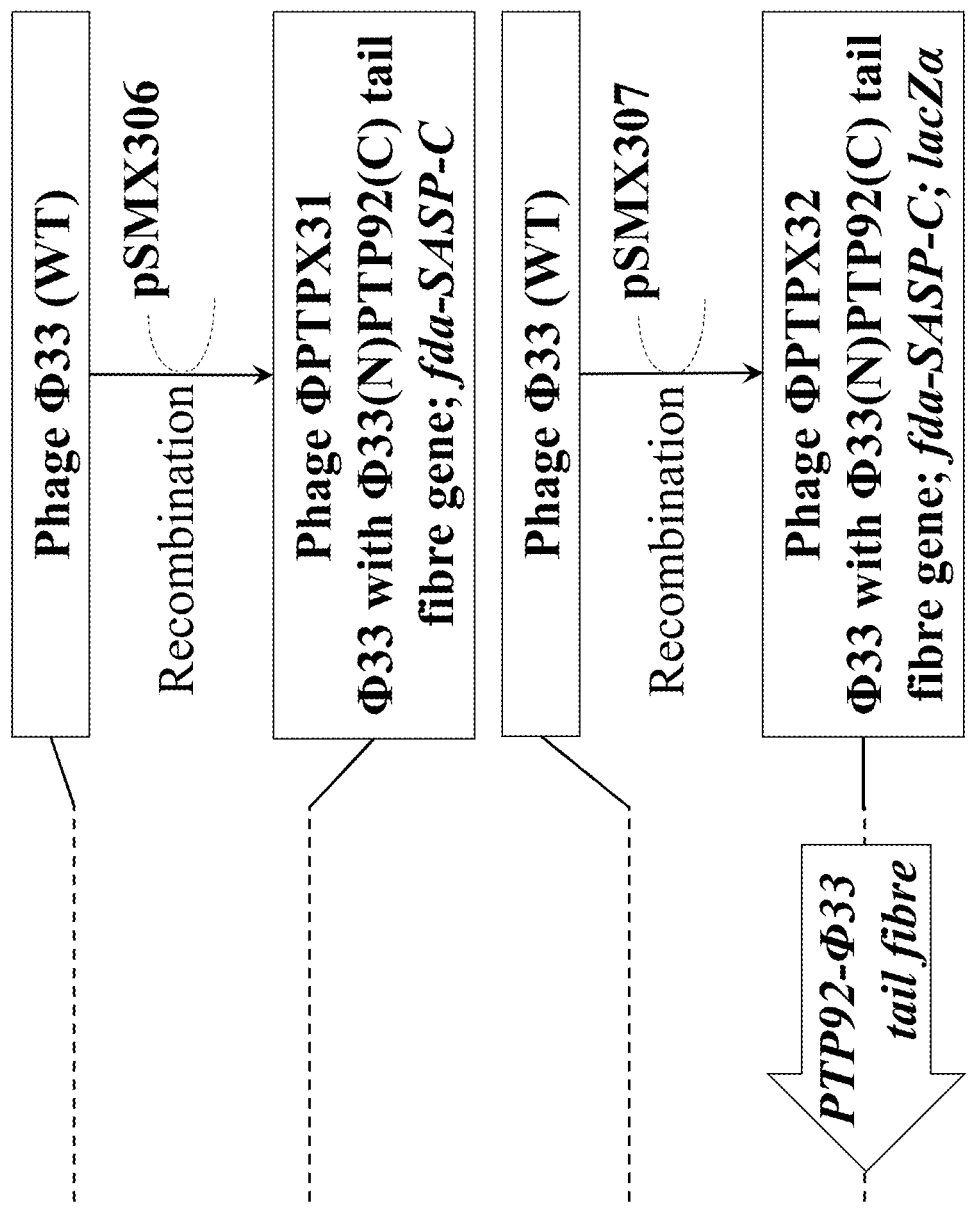
Figure 4A:
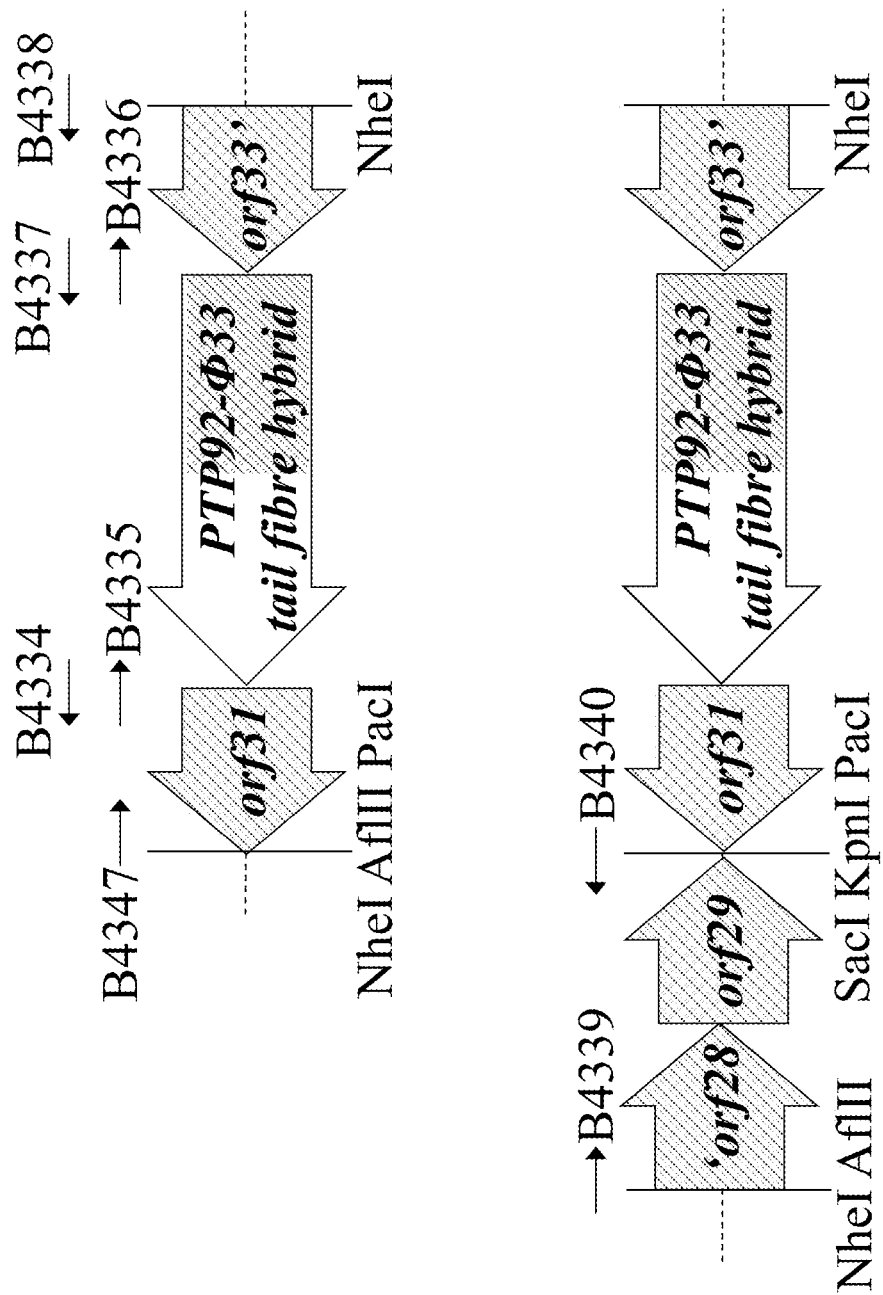
FIG. 4A-4D is a schematic diagram showing construction of plasmids with replaced tail fibre sections, for the genetic modification of phage to replace the endolysin gene by SASP-C, or by SASP-C and lacZα marker.
Figure 4B:
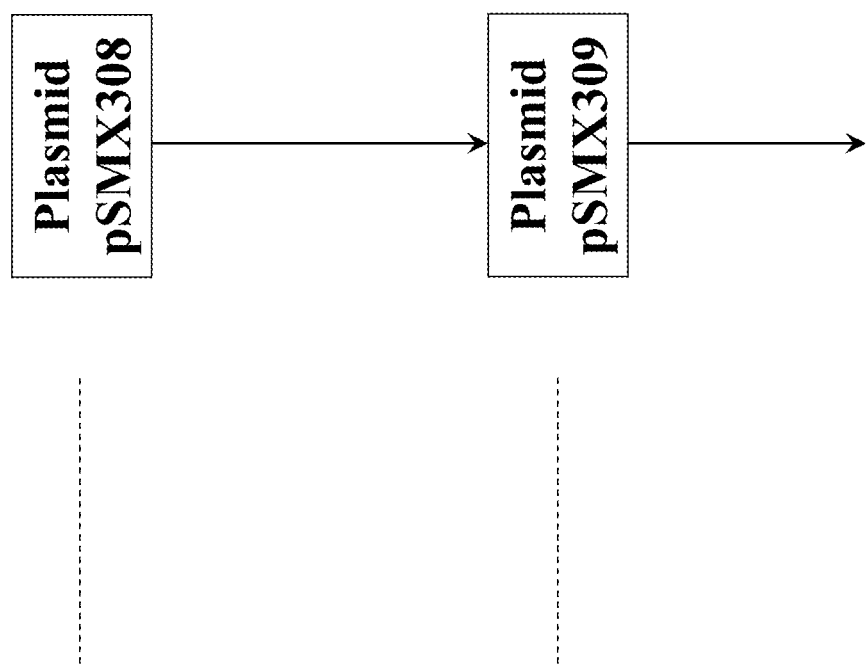
Figure 4C:
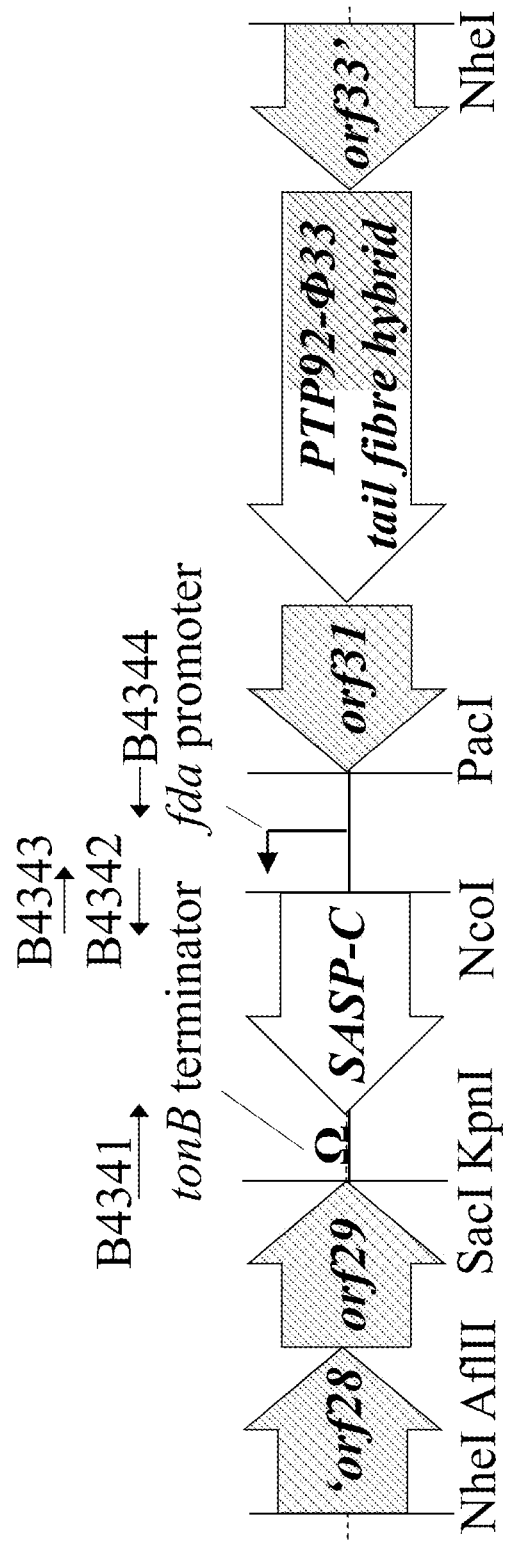
Figure 4D:
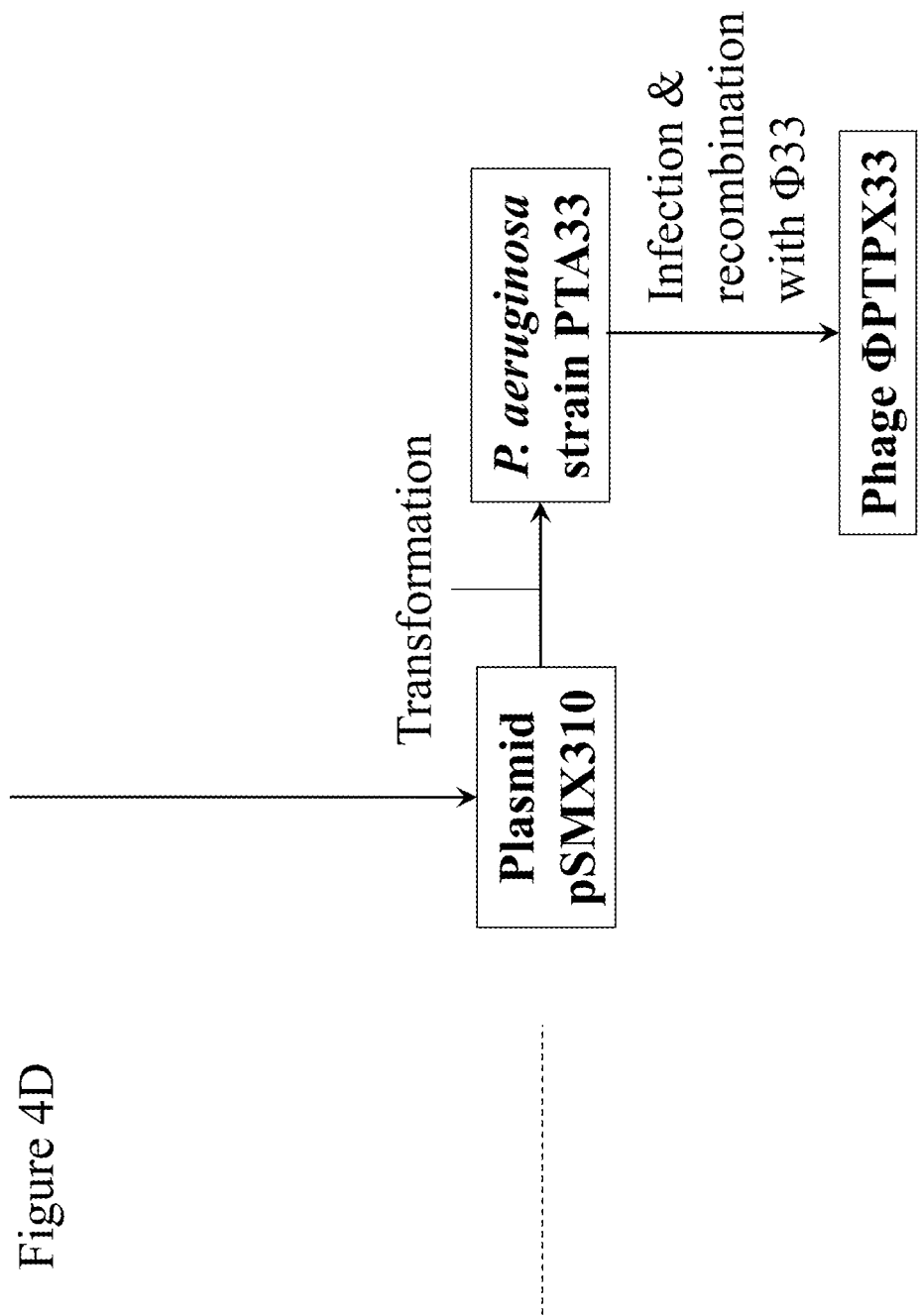

Genetic Modification of Phi33 to Add Fda-SASP-C and lacZα to the Bacteriophage Genome, Utilising the PTP92 Host Range Determinant as a Means of Selection 1. Plasmid pSMX307 (FIG. 2A-2D; FIG. 3A-3B) may be introduced into a *P. aeruginosa* strain that is a host for both the original, and the host range determinant donor phage, by conjugation, selecting transconjugants on the basis of tetracycline resistance (50 μg/ml), yielding strain PTA32.

2. Strain PTA32 may be infected with phage Phi33, and the progeny phage harvested.

3. Recombinant phage, in which the PTP92 host range determinant has been transferred to Phi33, may be identified by plaquing the lysate from step (2) on *P. aeruginosa* strain 2726, which is a host for the recombinant phage that carries the PTP92 host range determinant, but which is not a host for the parental bacteriophage Phi33.

4. A PCR screen may be further carried out to identify isolates that have simultaneously acquired fda-SASP-C and lacZα, in addition to the host range determinant from PTP92.

5. Isolates that have acquired lacZα may further be confirmed by plaquing on *Pseudomonas aeruginosa* strain PAX32 (FIG. 1A-1B), using culture medium containing the chromogenic substrate for β-galactosidase, S-Gal (Sigma). Bacteriophage which carry the lacZα reporter generate black plaques on this host, using this culture medium, while plaques of bacteriophage lacking the lacZα reporter remain clear.

6. Following identification of a verified isolate (PTPX32; FIG. 3A-3B), this isolate may be plaque purified twice more on, prior to further use.

Construction of a Plasmid to Simultaneously Delete a Section of Bacteriophage Phi33 (the Endolysin Gene) and Introduce a New Section of DNA (Fda-SASP-C) into the Genome of Bacteriophage Phi33, Utilising an Alternative Host Range Determinant as a Selectable Marker.

1. Plasmid pSMX308 (FIG. 4A-4D), comprising pSM1080 carrying Phi33 sequences flanking sequences of the tail fibre host range determinant of the related bacteriophage PTP92, but including a deletion of the endolysin gene, may be constructed as follows.

The region immediately downstream of the Phi33 tail fibre may be amplified by PCR using primers B4347 and B4334 (FIG. 4A-4D). The region encoding the C-terminal, receptor-binding region of bacteriophage PTP92 may be amplified by PCR using primers B4335 and B4336 (FIG. 4A-4D). These two PCR products may then be joined by SOEing PCR using the outer primers B4347 and B4336. The Phi33 sequence that encodes the N-terminal region of the Phi33 tail fibre, and the tail fibre upstream sequence may be amplified from Phi33 by PCR using primers B4337 and B4338. This Phi33 tail fibre region may then be joined to the PCR product comprising the region downstream of the Phi33 tail fibre and the PTP92 host range determinant, by SOEing PCR using the outer primers B4347 and B4338. The resulting PCR product may then be cleaned, digested with NheI, cleaned again and then ligated to pSM1080 that has been digested with NheI, treated with alkaline phosphatase and cleaned, prior to ligation. This construction yields plasmid pSMX308 (FIG. 4A-4D).

Primer B4347 consists of 5' NheI-AflII-PacI restriction sites (underlined) followed by sequence complementary to a region approximately 1 kb downstream of the Phi33 tail fibre (FIG. 4A-4D). Primer B4334 consists of 5' sequence of the PTP92 host range determinant, followed by sequence immediately downstream of the Phi33 tail fibre (underlined; FIG. 4A-4D). Primer B4335 is the reverse complement of primer B4334 (FIG. 4A-4D). Primer B4336 consists of 5' sequence complementary to the PTP92 host range determinant, followed by sequence complementary to the Phi33 tail fibre (underlined; FIG. 4A-4D). Primer B4337 is the reverse complement of primer B4336 (FIG. 4A-4D). Primer B4338 consists of a 5' NheI restriction site (underlined), followed by sequence of a region upstream of the Phi33 tail fibre (FIG. 4A-4D).

```
Primer B4347
                                       (SEQ ID NO: 25)
5'-GATAGCTAGCGACTTAAGGATTAATTAATCAATACTCCTGATTTTT

G-3'

Primer B4334
                                       (SEQ ID NO: 12)
5'-CTATTCCAGCGGGTAACGTAAAATGAAATGGACGCGGATCAG-3'

Primer B4335
                                       (SEQ ID NO: 13)
5'-CTGATCCGCGTCCATTTCATTTTACGTTACCCGCTGGAATAG-3'

Primer B4336
                                       (SEQ ID NO: 14)
5'-CTCAAGCGGGCCGGCTGGTCTCTCGGCAATAACTCCTATGTGATCAC

C-3'

Primer B4337
                                       (SEQ ID NO: 15)
5'-GGTGATCACATAGGAGTTATTGCCGAGAGACCAGCCGGCCCGCTTGA

G-3'

Primer B4338
                                       (SEQ ID NO: 16)
5'-GATAGCTAGCGGAGTACCGCTTACGTCTC-3'
```

2. Plasmid pSMX309 (FIG. 4A-4D), comprising pSMX308 carrying a region of Phi33 DNA immediately downstream of the endolysin gene, which is the location chosen here for insertion of the fda-SASP-C foreign DNA, may be constructed as follows.

An approximately 1 kb region of Phi33 DNA located immediately downstream of the endolysin gene, the location chosen here for insertion of the fda-SASP-C foreign DNA, may be amplified by PCR using primers B4339 and B4340 (FIG. 4A-4D). The resulting PCR product may then be digested with AflII and PacI, cleaned, and ligated to pSMX308 that has also been digested with AflII and PacI and cleaned, prior to ligation, yielding plasmid pSMX309 (FIG. 4A-4D).

Primer B4339 consists of a 5' AflII restriction site (underlined), followed by Phi33 sequence approximately 1 kb downstream of the endolysin gene, the location chosen here for insertion of the fda-SASP-C DNA (FIG. 4A-4D). Primer B4340 consists of 5' PacI-KpnI-SacI restriction sites (underlined), followed by sequence complementary to Phi33 sequence located immediately downstream of the endolysin gene, the location chosen here for insertion of the fda-SASP-C DNA (FIG. 4A-4D).

```
Primer B4339
                                       (SEQ ID NO: 17)
5'-GATACTTAAGTCGCTCCAGCCATGCGGAAAAC-3'

Primer B4340
                                       (SEQ ID NO: 18)
5'-GATATTAATTAATCGGTACCTCGAGCTCTATTCGCCCAAAAGAAAA

G-3'
```

3. Plasmid pSMX310 (FIG. 4A-4D), comprising pSMX309 carrying fda-SASP-C, may be constructed as follows.

The SASP-C gene from *Bacillus megaterium* strain KM (ATCC 13632) may be amplified by PCR using primers B4341 and B4342 (FIG. 4A-4D). The resulting PCR product may then be cleaned, digested with KpnI and NcoI, and cleaned again. The *Pseudomonas aeruginosa* fda promoter may be amplified by PCR using primers B4343 and B4344 (FIG. 4A-4D). The resulting PCR product may then be cleaned, digested with NcoI and Pact, and cleaned again. The two PCR products may then be ligated, in a 3-way ligation, to pSMX309 that has been digested with KpnI and Pact and cleaned prior to ligation, to yield plasmid pSMX310 (FIG. 4A-4D).

Primer B4341 consists of a 5' KpnI restriction site (underlined), followed by a bi-directional transcription terminator (tonB terminator), followed by sequence complementary to the end of SASP-C from *Bacillus megaterium* strain KM (ATCC 13632) (underlined, in bold; FIG. 4A-4D). Primer B4342 (FIG. 4A-4D) consists of a 5' NcoI restriction site (underlined), followed by sequence of the beginning of the SASP-C gene from *Bacillus megaterium* strain KM (ATCC 13632). Primer B4343 consists of a 5' NcoI restriction site (underlined), followed by sequence of the fda promoter (FIG. 4A-4D). Primer B4344 consists of a 5' Pact restriction site (underlined), followed by sequence complementary to the fda promoter (FIG. 4A-4D).

```
B4341
                                            (SEQ ID NO: 19)
5'-GATAGGTACCAGTCAAAAGCCTCCGACCGGAGGCTTTTGACTTTAGT

ACTTGCCGCCTAG-3'

B4342
                                            (SEQ ID NO: 20)
5'-GATACCATGGCAAATTATCAAAACGCATC-3'

B4343
                                            (SEQ ID NO: 21)
5'-GATACCATGGTTCTCGTATCTCCCAATC-3'

B4344
                                            (SEQ ID NO: 22)
5'-GATATTAATTAACGACGAAGGCCTGGTG-3'
```

Genetic Modification of Phi33 to Simultaneously Delete the Phi33 Endolysin Gene, and Add Fda-SASP-C to the Bacteriophage Genome, Utilising the PTP92 Host Range Determinant as a Means of Selection 1. Plasmid pSMX310 (FIG. 4A-4D) may be introduced into a *P. aeruginosa* strain that is a host for both the original, and the host range determinant donor phage, by conjugation, selecting transconjugants on the basis of tetracycline resistance (50 µg/ml), yielding strain PTA33.

2. Strain PTA33 may be infected with phage Phi33, and the progeny phage harvested.

3. Recombinant phage, in which the PTP92 host range determinant has been transferred to Phi33, may be identified by plaquing the lysate from step (2) on *P. aeruginosa* strain PAX31 (endolysin+; FIG. 1A-1B), i.e. a strain 2726 derivative, which is a host for the recombinant phage that carries the PTP92 host range determinant, but which is not a host for the parental bacteriophage Phi33, and which carries the Phi33 endolysin gene in trans.

4. A PCR screen may be further carried out to identify isolates that have simultaneously acquired fda-SASP-C, in addition to the host range determinant from PTP92.

5. Isolates may further be tested for the endolysin deletion by plaquing on unmodified *P. aeruginosa* strain 2726 (endolysin), as phage isolates from which the endolysin has been successfully removed will fail to plaque on this strain.

Figure 5A:
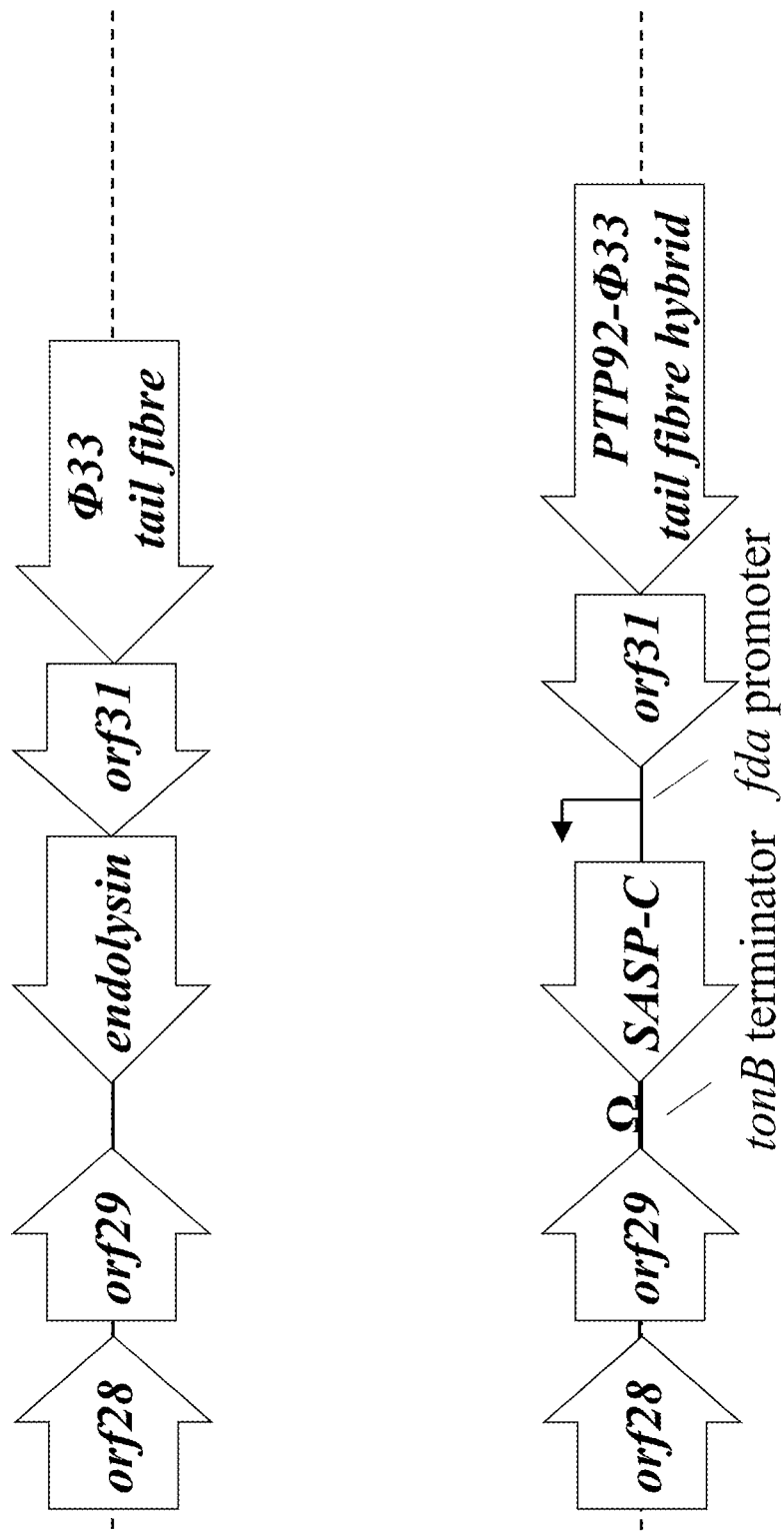
FIG. 5A-5B is a schematic diagram showing production of phage in which the endolysin gene has been deleted and replaced by SASP-C, or by SASP-C and a lacZα marker, by recombination, using HORDS as a means of selecting for recombinant phage.
Figure 5B:
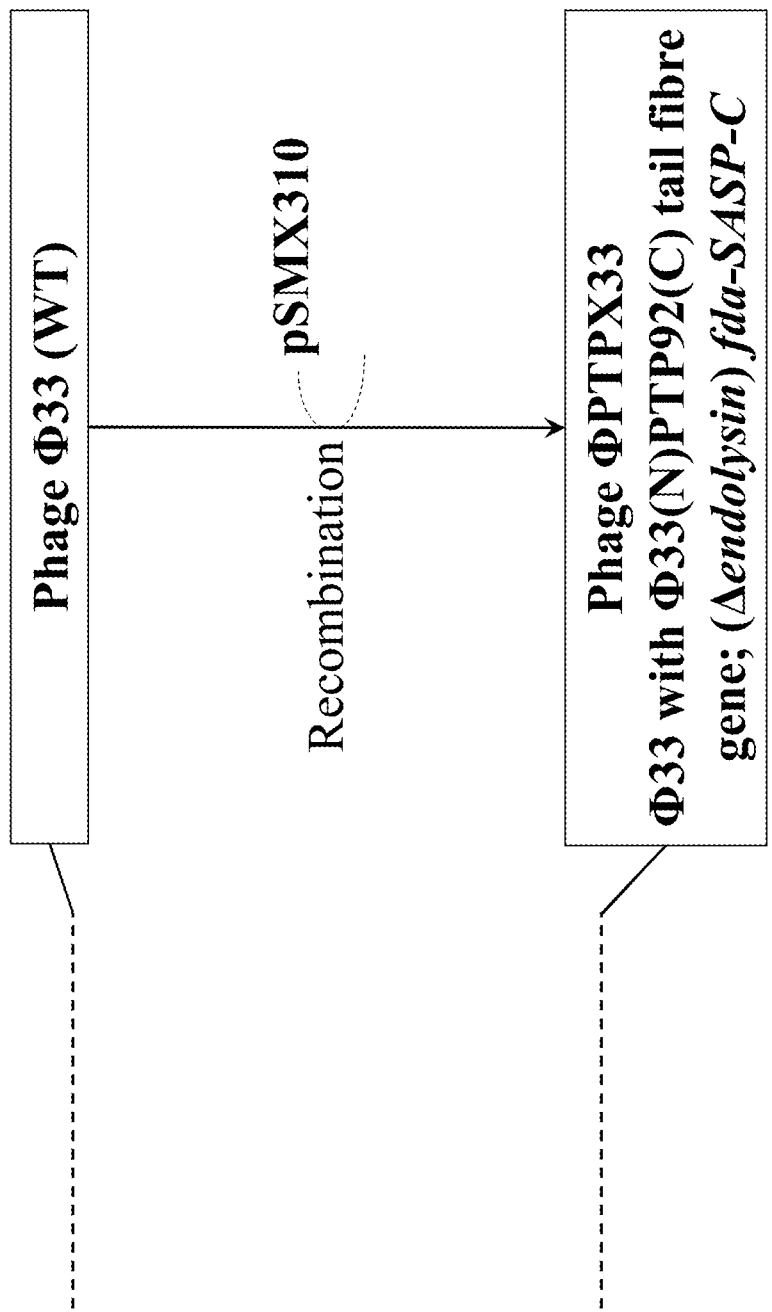

5. Following identification of a verified isolate (PTPX33; FIG. 5A-5B), this isolate may be plaque purified twice more on an endolysin+ *P. aeruginosa* strain, prior to further use.

TABLE 1

Host range of Phi33, PTP92, C36 and PTP47 against 44 European clinical isolates of *Pseudomonas aeruginosa*.

| Bacterial Strain no. | Phi33 | PTP47 | PTP92 | C36 |
|---|---|---|---|---|
| 2019 | + | + | − | + |
| 2020 | + | + | − | + |
| 2021 | + | + | + | + |
| 2029 | + | + | − | + |
| 2031 | + | + | + | + |
| 2039 | + | + | + | + |
| 2040 | + | + | − | + |
| 2041 | + | + | + | + |
| 2042 | + | + | + | + |
| 2045 | − | − | + | − |
| 2046 | + | + | + | + |
| 2047 | + | + | + | + |
| 2048 | + | + | + | + |
| 2049 | + | + | + | + |
| 2050 | + | + | + | + |
| 2051 | + | + | − | − |
| 2052 | − | − | − | − |
| 2053 | + | + | − | + |
| 2054 | − | + | − | + |
| 2055 | + | + | − | + |
| 2056 | + | + | + | + |
| 2057 | + | + | + | + |
| 2058 | + | + | + | + |
| 2483 | − | − | + | − |
| 2484 | + | + | − | + |
| 2705 | + | + | − | + |
| 2706 | + | + | − | + |
| 2707 | + | + | + | + |
| 2708 | + | + | + | + |
| 2709 | + | + | + | + |
| 2710 | − | + | + | − |
| 2711 | + | + | + | + |
| 2712 | + | + | − | + |
| 2713 | − | + | + | + |
| 2714 | + | + | + | + |
| 2715 | + | + | + | + |
| 2716 | + | + | − | − |
| 2717 | − | + | + | + |
| 2718 | − | + | + | + |
| 2719 | + | + | − | + |
| 2720 | + | + | + | + |
| 2721 | + | + | + | + |
| 2722 | + | + | + | + |
| 2723 | + | + | − | + |

Strains were tested for sensitivity to each phage by dropping 10 µl of crude phage lysate onto a soft agar overlay plate inoculated with bacteria. Plates were grown overnight at 32° C. and the strains were scored for sensitivity to each phage by assessing clearance zones at the point of inoculation. Where phage inhibited growth, as seen by clearance of the bacterial lawn, the strain was marked as sensitive (+), and where no inhibition of growth was seen, the strain was marked as not-sensitive (−)

REFERENCES

Abedon S T. (2008). Bacteriophage Ecology: Population Growth, Evolution, an Impact of Bacterial Viruses. Cambridge. Cambridge University Press. Chapter 1.

Brabban A D, Hite E, Callaway T R. (2005). Evolution of Foodborne Pathogens via Temperate Bacteriophage-Mediated Gene Transfer. *Foodborne Pathogens and Disease*, 2:287-303.

Ceyssens P, Miroshnikov K, Mattheus W, Krylov V, Robben J, Noben J, Vanderschraeghe S, Sykilinda N, Kropinski A M, Volckaert G, Mesyanzhinov V, Lavigne R. (2009).

Comparative analysis of the widespread and conserved PB1-like viruses infecting *Pseudomonas aeruginosa. Env. Microbiol.* 11:2874-2883.

Dobozi-King M, Seo S, Kim J U, Young R, Cheng M, Kish L B. (2005). Rapid detection and identification of bacteria: SEnsing of Phage-Triggered Ion Cascade (SEPTIC), *Journal of Biological Physics and Chemistry.* 5:3-7.

Francesconi, S. C., MacAlister, T. J., Setlow, B., & Setlow, P. (1988). Immunoelectron microscopic localization of small, acid-soluble spore proteins in sporulating cells of *Bacillus subtilis. J. Bacteriol.,* 170: 5963-5967.

Frenkiel-Krispin, D., Sack, R., Englander, J., Shimoni, E., Eisensiein, M., Bulliti, E. & Wolf, S. G. (2004). Structure of the DNA-SspC complex: implications for DNA packaging, protection, and repair in bacterial spores. *J. Bacteriol.* 186:3525-3530.

Gill J J, Hyman P. (2010). Phage Choice, Isolation and Preparation for Phage therapy. *Current Pharmaceutical Biotechnology.* 11:2-14.

Harper D R, Anderson J, Enwright M C. (2011). Phage therapy: delivering on the promise. *Ther Deliv.* 2:935-47.

Hendrix R W. (2009). Jumbo Bacteriophages. *Curr. Topics Microbiol. Immunol.* 328:229-40.

Lee, K. S. Bumbaca, D. Kosman, J., Setlow, P., & Jedrzejas, M. 1 (2008). Structure of a protein—DNA complex essential for DNA protection in spores of *Bacillus* species. *Proc. Natl. Acad. Sci.* 105:2806-2811.

Mark D F, Richardson C C. (1976). *Escherichia coli* thioredoxin: a subunit of bacteriophage T7 DNA polymerase. Proc. Natl. Acad. Sci. USA. 73:780-4.

Marinelli L J, Piuri M, Swigonová Z, Balachandran A, Oldfield L M, van Kessel J C, Hatfull G F. (2008). BRED: a simple and powerful tool for constructing mutant and recombinant bacteriophage genomes. *PLoS One.* 3:e3957.

Nicholson W L, Setlow B, Setlow P. (1990). Binding of DNA in vitro by a small, acid-soluble spore protein from *Bacillus subtilis* and the effect of this binding on DNA topology. *J. Bacteriol.* 172:6900-6906.

Pouillot F, Blois H, and Iris F. (2010). Biosecurity and Bioterrorism: Biodefense Strategy, Practice, and Science. *Biosecurity and Bioterrorism.* 8: 155-169

Qimron U, Marintcheva B, Tabor S, Richardson C C. (2006). Genomewide screens for *Escherichia coli* genes affecting growth of T7 bacteriophage. *Proc. Natl. Acad. Sci. USA.* 103:19039-44.

Rakhuba D V, Kolomiets E I, Szwajcer Dey E, Novik E I. (2010). Bacteriophage Receptors, Mechanisms of Phage Adsorption and Penetration into Host Cell. *Polish Journal of Microbiology.* 59:145-155.

Sheng Y, Mancino V, Birren B. (1995). Transformation of *Escherichia coli* with large DNA molecules by electroporation. *Nucl. Acids Res.* 23:1990-6.

Smith G P, Petrenko V A. (2005). Phage Display. *Chem. Rev.* 97:391-410.

Thomason L C Sawitzke J A, Li X, Costantino N, Court D L. (2014). Recombineering: genetic engineering in bacteria using homologous recombination. *Curr. Protoc. Mol. Biol.* 106:1-16.

Veesler D, Cambillau C. (2011). A Common Evolutionary Origin for Tailed-Bacteriophage Functional Modules and Bacterial Machineries. *Microbiol. Mol. Biol. Rev.* 75:423-433.

Waldor M, Mekalanos J. (1996). Lysogenic conversion by a filamentous phage encoding cholera toxin. *Science.* 272: 1910-1914.

Williamson S J, Houchin L A, McDaniel L, Paul J H. (2002). Seasonal variation in lysogeny as depicted by prophage induction in Tampa Bay, Fla. *Appl. Environ. Microbiol.* 68:4307-14.

Yu D, Ellis H M, Lee E C, Jenkins N A, Copeland N G, et al. (2000). An efficient recombination system for chromosome engineering in *Escherichia coli. Proc. Natl. Acad. Sci. USA.* 97:5978-5983.

The invention claimed is:

1. A method for modifying the genome of a lytic target phage, wherein the target phage genome includes a first target sequence and a second target sequence, which method comprises:
   (a) providing a vector which contains a phage-targeting region comprising a host range determinant of a marker phage, different from the host range determinant of the target phage, wherein the phage-targeting region is flanked by first and second flanking sequences homologous to the first and second target sequences of the target phage genome, and wherein the phage-targeting region of the vector further comprises an exogenous DNA sequence for incorporation into the genome of the target phage;
   (b) introducing the vector into a first host cell, which host cell is a host for the target phage;
   (c) infecting the first host cell with the target phage;
   (d) allowing replication of the phage and recombination between the target phage genome and vector to take place whereby the genome of the target phage is modified;
   (e) propagating resultant phage on a second host cell, which host cell is a host for the marker phage and not the target phage, wherein said propagating indicates that said resultant phage comprise said exogenous DNA sequence; and
   (f) harvesting the resultant phage.

2. The method according to claim 1, wherein the exogenous DNA comprises a gene which encodes an antibacterial protein.

3. The method according to claim 2, wherein the gene is under the control of a constitutive promoter.

4. The method according to claim 2, for the production of a modified bacteriophage capable of infecting a plurality of different target bacteria, which modified bacteriophage includes a SASP which is toxic to the target bacteria; wherein the modified bacteriophage is non-lytic.

5. The method according to claim 4, wherein the modified bacteriophage expresses a plurality of different host range determinants or tail fibre proteins and wherein each host range determinant has a different bacterial host specificity; or wherein the bacteriophage expresses a host range determinant protein or tail fibre protein which comprises an amino acid sequence from a plurality of different bacteriophages.

6. The method according to claim 5, wherein the bacterial host specificity of the host range determinants are within the same bacterial species.

7. The method according to claim 1, wherein the first and second target sequences of the target phage genome are non-contiguous.

8. The method according to claim 7, wherein the first and second target sequences of the target phage genome flank a phage gene, a lysis gene, or part thereof, such that the recombination between the target phage genome and vector inactivates the gene.

9. The method according to claim 1, wherein at least one of the first and second flanking sequences contains a mutation as compared with the first and second target sequences of the target phage genome.

10. The method according to claim 1, wherein the host range determinant of the marker phage encodes a tail fibre protein or region thereof.

11. The method according to claim 1, wherein the host range determinant of the marker phage encodes a tail fibre protein which comprises a receptor binding region for binding to the second host cell and a region linking the receptor binding region to the body of the phage.

12. The method according to claim 11, wherein the receptor binding region is a C-terminal receptor binding region and the region linking the C-terminal receptor binding region to the body of the phage is an N-terminal region.

13. The method according to claim 12, wherein the C-terminal region has no more than 96% amino acid sequence identity with the C-terminal region of bacteriophage Phi33.

14. The method according to claim 13, wherein the C-terminal region is from any one of bacteriophage Phi33, LBL3, SPM-1, F8, PR1, KPP12, LMA2, SN, 14-1, JG024, NH-4, PTP47, C36, PTP93 and PTP92.

15. The method according to claim 13, wherein the C-terminal region amino sequence identity is less than 80%.

16. The method according to claim 12, wherein the N-terminal region has at least 95% amino acid sequence identity with the N-terminal region of bacteriophage Phi33.

17. The method according to claim 16, wherein the N-terminal region is from any one of bacteriophage Phi33, LBL3, SPM-1, F8, PB1, KPP12, LMA2, SN, 14-1, JG024, NH-4, PTP47, C36, PTP92 and PTP93.

18. The method according to claim 12, wherein the tail fibre protein has more than 80% amino acid sequence identity with the tail fibre amino acid sequence of bacteriophage Phi33.

19. The method according to claim 18, wherein the tail fibre protein is from a bacteriophage selected from Phi33, LBL3, SPM-1, F8, PB1, KPP12, LMA2, SN, 14-1, JG024, NH-4, PTP47, C36, PTP92 and PTP93.

20. The method according to claim 18, wherein the amino acid sequence identity is more than 95%.

21. The method according to claim 12, wherein the second host cell is a *Pseudomonas* host cell.

* * * * *

SEQUENCE LISTING

```
<160> NUMBER OF SEQ ID NOS: 39

<210> SEQ ID NO 1
<211> LENGTH: 30
<212> TYPE: DNA
<213> ORGANISM: Artificial Sequence
<220> FEATURE:
<223> OTHER INFORMATION: Primer B4300

<400> SEQUENCE: 1
gataactagt cctggtccac cggggtcaag                                        30

<210> SEQ ID NO 2
<211> LENGTH: 36
<212> TYPE: DNA
<213> ORGANISM: Artificial Sequence
<220> FEATURE:
<223> OTHER INFORMATION: Primer B4301

<400> SEQUENCE: 2
gctcagatct tccttaagtc agtcgcgcag gttcag                                 36

<210> SEQ ID NO 3
<211> LENGTH: 37
<212> TYPE: DNA
<213> ORGANISM: Artificial Sequence
```

<220> FEATURE:
<223> OTHER INFORMATION: Primer B4302

<400> SEQUENCE: 3
aggaagatct gagctagctc ggaccagaac gaaaaag                      37

<210> SEQ ID NO 4
<211> LENGTH: 29
<212> TYPE: DNA
<213> ORGANISM: Artificial Sequence
<220> FEATURE:
<223> OTHER INFORMATION: Primer B4303

<400> SEQUENCE: 4
gatactcgag gcggatgaac attgaggtg                              29

<210> SEQ ID NO 5
<211> LENGTH: 72
<212> TYPE: DNA
<213> ORGANISM: Artificial Sequence
<220> FEATURE:
<223> OTHER INFORMATION: Primer B4304

<400> SEQUENCE: 5
gatacttaag aaaacaaact aaagcgccct tgtggcgctt tagttttata ctactgagaa    60
aaatctggat tc                                                72

<210> SEQ ID NO 6
<211> LENGTH: 43
<212> TYPE: DNA
<213> ORGANISM: Artificial Sequence
<220> FEATURE:
<223> OTHER INFORMATION: Primer B4305

<400> SEQUENCE: 6
gattttcatc aatactcctg gatcccgtta attcgaagag tcg               43

<210> SEQ ID NO 7
<211> LENGTH: 43
<212> TYPE: DNA
<213> ORGANISM: Artificial Sequence
<220> FEATURE:
<223> OTHER INFORMATION: Primer B4306

<400> SEQUENCE: 7
cgactcttcg aattaacggg atccaggagt attgatgaaa atc               43

<210> SEQ ID NO 8
<211> LENGTH: 29
<212> TYPE: DNA
<213> ORGANISM: Artificial Sequence
<220> FEATURE:
<223> OTHER INFORMATION: Primer B4307

<400> SEQUENCE: 8
gataagatct tcaggagcct tgattgatc                              29

<210> SEQ ID NO 9
<211> LENGTH: 31
<212> TYPE: DNA
<213> ORGANISM: Artificial Sequence
<220> FEATURE:
<223> OTHER INFORMATION: Primer B4308

<400> SEQUENCE: 9
gataagatct gagcgcaacg caattaatgt g                                   31

<210> SEQ ID NO 10
<211> LENGTH: 64
<212> TYPE: DNA
<213> ORGANISM: Artificial Sequence
<220> FEATURE:
<223> OTHER INFORMATION: Primer B4309

<400> SEQUENCE: 10
gatagctagc agtcaaaagc ctccggtcgg aggcttttga ctttattttt gacaccagac    60
caac                                                                 64

<210> SEQ ID NO 11
<211> LENGTH: 47
<212> TYPE: DNA
<213> ORGANISM: Artificial Sequence
<220> FEATURE:
<223> OTHER INFORMATION: Primer B4333

<400> SEQUENCE: 11
gatagctagc gacttaagga ttaattaatc aggagccttg attgatc                  47

<210> SEQ ID NO 12
<211> LENGTH: 42
<212> TYPE: DNA
<213> ORGANISM: Artificial Sequence
<220> FEATURE:
<223> OTHER INFORMATION: Primer B4334

<400> SEQUENCE: 12
ctattccagc gggtaacgta aaatgaaatg gacgcggatc ag                       42

<210> SEQ ID NO 13
<211> LENGTH: 42
<212> TYPE: DNA
<213> ORGANISM: Artificial Sequence
<220> FEATURE:
<223> OTHER INFORMATION: Primer B4335

<400> SEQUENCE: 13
ctgatccgcg tccatttcat tttacgttac ccgctggaat ag                       42

<210> SEQ ID NO 14
<211> LENGTH: 48
<212> TYPE: DNA
<213> ORGANISM: Artificial Sequence
<220> FEATURE:
<223> OTHER INFORMATION: Primer B4336

<400> SEQUENCE: 14
ctcaagcggg ccggctggtc tctcggcaat aactcctatg tgatcacc                 48

<210> SEQ ID NO 15
<211> LENGTH: 48
<212> TYPE: DNA
<213> ORGANISM: Artificial Sequence
<220> FEATURE:
<223> OTHER INFORMATION: Primer B4337

<400> SEQUENCE: 15
ggtgatcaca taggagttat tgccgagaga ccagccggcc cgcttgag                 48

```
<210> SEQ ID NO 16
<211> LENGTH: 29
<212> TYPE: DNA
<213> ORGANISM: Artificial Sequence
<220> FEATURE:
<223> OTHER INFORMATION: Primer B4338

<400> SEQUENCE: 16
gatagctagc ggagtaccgc ttacgtctc                                29

<210> SEQ ID NO 17
<211> LENGTH: 32
<212> TYPE: DNA
<213> ORGANISM: Artificial Sequence
<220> FEATURE:
<223> OTHER INFORMATION: Primer B4339

<400> SEQUENCE: 17
gatacttaag tcgctccagc catgcggaaa ac                            32

<210> SEQ ID NO 18
<211> LENGTH: 47
<212> TYPE: DNA
<213> ORGANISM: Artificial Sequence
<220> FEATURE:
<223> OTHER INFORMATION: Primer B4340

<400> SEQUENCE: 18
gatattaatt aatcggtacc tcgagctcta ttcgcccaaa agaaaag            47

<210> SEQ ID NO 19
<211> LENGTH: 60
<212> TYPE: DNA
<213> ORGANISM: Artificial Sequence
<220> FEATURE:
<223> OTHER INFORMATION: Primer B4341

<400> SEQUENCE: 19
gataggtacc agtcaaaagc ctccgaccgg aggcttttga ctttagtact tgccgcctag   60

<210> SEQ ID NO 20
<211> LENGTH: 29
<212> TYPE: DNA
<213> ORGANISM: Artificial Sequence
<220> FEATURE:
<223> OTHER INFORMATION: Primer B4342

<400> SEQUENCE: 20
gataccatgg caaattatca aaacgcatc                                29

<210> SEQ ID NO 21
<211> LENGTH: 28
<212> TYPE: DNA
<213> ORGANISM: Artificial Sequence
<220> FEATURE:
<223> OTHER INFORMATION: Primer B4343

<400> SEQUENCE: 21
gataccatgg ttctcgtatc tcccaatc                                 28

<210> SEQ ID NO 22
<211> LENGTH: 28
<212> TYPE: DNA
<213> ORGANISM: Artificial Sequence
<220> FEATURE:
<223> OTHER INFORMATION: Primer B4344
```

-continued

<400> SEQUENCE: 22
gatattaatt aacgacgaag gcctggtg                                        28

<210> SEQ ID NO 23
<211> LENGTH: 29
<212> TYPE: DNA
<213> ORGANISM: Artificial Sequence
<220> FEATURE:
<223> OTHER INFORMATION: Primer B4345

<400> SEQUENCE: 23
gatagagctc ttagcgccat tcgccattc                                       29

<210> SEQ ID NO 24
<211> LENGTH: 29
<212> TYPE: DNA
<213> ORGANISM: Artificial Sequence
<220> FEATURE:
<223> OTHER INFORMATION: Primer B4346

<400> SEQUENCE: 24
gataggtacc gcgcaacgca attaatgtg                                       29

<210> SEQ ID NO 25
<211> LENGTH: 47
<212> TYPE: DNA
<213> ORGANISM: Artificial Sequence
<220> FEATURE:
<223> OTHER INFORMATION: Primer B4347

<400> SEQUENCE: 25
gatagctagc gacttaagga ttaattaatc aatactcctg attttg                    47

<210> SEQ ID NO 26
<211> LENGTH: 964
<212> TYPE: PRT
<213> ORGANISM: Bacteriophage SPM-1

<400> SEQUENCE: 26

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Ala Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
        115                 120                 125

Trp Ser Val Met Arg Ser Asn Ile Pro Met Pro Ala Gly Gly Ser Gly
    130                 135                 140

Leu Ser Ser Gly Gly Glu Val Ile Thr Thr Gly Arg Asn Phe Asn Asp
145                 150                 155                 160

```
Leu Leu Asn Gly Thr Trp Glu Phe Phe Ser Asp Ser Val Val Val Ala
            165                 170                 175
Ser Gln Asn Ala Pro Val Tyr Pro Ala Ser Ala Gly Ala Ala Ala Gly
        180                 185                 190
Met Leu Glu Ala Lys Ser Trp Val Ser Gly Ala Asn Thr Phe Cys Val
        195                 200                 205
Gln Arg Tyr Thr Asp Arg Val Gly Asn Val Ala Val Arg Gly Leu Asn
    210                 215                 220
Ala Gly Ala Trp Thr Asn Trp Met Tyr Ala Val Asn Val Met Ala Leu
225                 230                 235                 240
Gln Gln Gly Arg Val Thr Tyr Gly Val Ala Ala Gly Ser Ala Asn Ala
                245                 250                 255
Tyr Thr Leu Thr Leu Val Pro Gln Leu Gln Gly Gly Leu Val Asp Gly
            260                 265                 270
Met Val Leu Arg Val Lys Phe Asn Ala Met Asn Thr Gly Ala Ser Thr
        275                 280                 285
Ile Asn Val Ser Gly Phe Gly Ser Lys Ala Ile Val Gly Ala Ala Asn
    290                 295                 300
Phe Pro Leu Thr Gly Gly Glu Leu Gly Gln Gly Leu Ile Ala Glu Leu
305                 310                 315                 320
Val Phe Asp Ala Thr Gly Asp Arg Trp Arg Ile Leu Ala Gly Ala Pro
                325                 330                 335
Arg Ile Gln Val Gly Asn Ala Asp Gln Asp Tyr Gln Ala Pro Ser Trp
            340                 345                 350
Lys Gln Val Lys Asp Tyr Val Ala Ser Gln Lys Leu Thr Glu Val Asp
        355                 360                 365
Trp Ala Asp Val Val Asn Lys Pro Asn Val Ala Ile Gln Asp Thr Thr
    370                 375                 380
Pro Trp Phe Ala Asn Leu Glu Leu Ser Asp Ala Arg Pro Phe Ile Asp
385                 390                 395                 400
Phe His Phe Asn Asn Arg Ala Lys Asp Phe Asp Tyr Arg Phe Ile
                405                 410                 415
Ser Glu Ala Asp Gly Ser Met Ala Phe Tyr Ser Arg Gln Gly Ser Ala
            420                 425                 430
Gly Pro Thr Gln Asp Ile Leu Phe Ser Arg Ser Asn Val Thr Phe Leu
        435                 440                 445
Gln Pro Arg Leu Asp Val Ala Lys Asn Leu Ala Tyr Ile Ala Asn Ser
    450                 455                 460
Gly Pro Leu Trp Gln Asn Thr Thr Ala Asp Gln Pro Gly Trp Lys Phe
465                 470                 475                 480
Thr Phe Ala Gln Gly Val Asp Ala Asn Asn Ala Val Ile Ala Val
                485                 490                 495
Asn Thr Thr Asn Pro Asp Gly Ser Tyr Arg Ser Gln Ile Met Arg Trp
            500                 505                 510
Asp Trp Ala Ser Thr Asn Val Ile Phe Asn Asn Arg Pro Leu Phe Ala
        515                 520                 525
Gly Gln Tyr Val Pro Trp Asp Ser Gly Asn Phe Asp Pro Ala Thr Lys
    530                 535                 540
Leu Thr Val Gly Thr Asn Asn Ile Ser Gly Pro Thr Gly Ile Arg
545                 550                 555                 560
Asn Thr Thr Ser Asn Thr Gly Asn Met Asn Thr Trp Gly Ser Ser Ser
                565                 570                 575
Thr Thr Ala Ser Tyr Gly Asn Ala Ala Leu Gln Ile Phe Gly Arg Gly
```

```
                580                 585                 590
    Gly Gly Glu Pro Ala Ala Ile Tyr Phe Asp Asn Ser Gln Thr Gly Trp
                    595                 600                 605
    Tyr Leu Gly Met Asp Lys Asp Gly Gln Leu Lys Arg Ala Gly Trp Ser
                610                 615                 620
    Leu Gly Asn Asn Ser Tyr Val Val Thr Asp Glu Ser Asn Ile Arg Asn
    625                 630                 635                 640
    His Val Asn Gly Met Ser Gly Ala Pro Val Trp Gly Gly Gln Trp Phe
                    645                 650                 655
    Trp Gly Glu Trp Asn Phe Asn Pro Asn Thr Lys Leu Thr Ile Lys Ala
                660                 665                 670
    Gly Thr Gln Glu Thr Ser Thr Ala Ile Phe Ser Gly Thr Leu Pro
                675                 680                 685
    Phe Ala Pro Ile Ala Ser Leu Ser Asp Tyr Ser Gln Ala Pro Leu Thr
                    690                 695                 700
    Ile Tyr Asn Ser Pro Thr Gly Pro Ser Ala Lys Pro Ala Val Ile Ala
    705                 710                 715                 720
    Phe Ile Arg Pro Gly Asn Trp Gly Ala Phe Phe Gly Ile Asp Thr Asp
                    725                 730                 735
    Asn Lys Leu Lys Trp Gly Gly Ser Leu Gly Asn Asn Ser Arg Glu
                740                 745                 750
    Ile Ala Asp Ser Ser Asn Ile Met Asn Leu Trp Ala Ser Asn Pro Thr
                755                 760                 765
    Ala Pro Ser Trp Asn Gly Gln Thr Val Trp Arg Ser Gly Asn Phe Asp
    770                 775                 780
    Pro Ala Thr Lys Val Asp Leu Asn Ala Ala Asn Ala Thr Asn Gly Ser
    785                 790                 795                 800
    Met Ile Phe Asn Arg Ile Ser Gly Thr Gly Ser Gly Ile Ala Ser Ser
                    805                 810                 815
    Gly Arg Val Gly Ala Ile Asn Leu Gln Asn Gly Ala His Ser Gly Gln
                820                 825                 830
    Ala Ala Ala Val Thr Phe Glu Arg Gly Gly Ser Ile Phe Val Asn Phe
                835                 840                 845
    Gly Leu Asp Thr Asp Asn Val Leu Lys Val Gly Gly Gly Asn Leu Gly
                850                 855                 860
    Ala Asn Ala Tyr Pro Val Ile His Ala Gly Asn Tyr Asn Asn Tyr Ile
    865                 870                 875                 880
    Asn Gln Ala Leu Val Gln Val Gly Leu Gly Gly Val Gly Ser Tyr Gly
                    885                 890                 895
    Ile Phe Ala Val Leu Asp Asn Ala Ala Pro Ile Ala Thr Val Gln Pro
                    900                 905                 910
    Gly Val Val Asp Gly Ser Ile Leu Ile Tyr Ser Ser Cys Ala Ala
                915                 920                 925
    Asn Tyr Asn Ser Gly Gln Lys Pro Ala Gly Thr Trp Arg Cys Met Gly
                930                 935                 940
    Tyr Val Val Asn Arg Asp Ala Asn Thr Ala Asp Ser Ala Thr Leu Phe
    945                 950                 955                 960
    Gln Arg Val Thr

<210> SEQ ID NO 27
<211> LENGTH: 964
<212> TYPE: PRT
<213> ORGANISM: Bacteriophage F8
```

<400> SEQUENCE: 27

```
Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Ala Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
        115                 120                 125

Trp Ser Val Met Arg Ser Asn Ile Pro Met Pro Ala Gly Gly Ser Gly
    130                 135                 140

Leu Ser Ser Gly Gly Glu Val Ile Thr Thr Gly Arg Asn Phe Asn Asp
145                 150                 155                 160

Leu Leu Asn Gly Thr Trp Glu Phe Phe Ser Asp Ser Val Val Ala Ala
                165                 170                 175

Ser Gln Asn Ala Pro Val Tyr Pro Ala Ser Gly Ala Ala Ala Gly
            180                 185                 190

Met Leu Glu Ala Lys Ser Trp Val Ser Gly Ala Asn Thr Phe Cys Val
        195                 200                 205

Gln Arg Tyr Thr Asp Arg Val Gly Asn Val Ala Val Arg Gly Leu Asn
    210                 215                 220

Ala Gly Ala Trp Thr Asn Trp Met Tyr Ala Val Asn Val Met Ala Leu
225                 230                 235                 240

Gln Gln Gly Arg Val Thr Tyr Gly Val Ala Ala Gly Ser Ala Asn Ala
                245                 250                 255

Tyr Thr Leu Thr Leu Val Pro Gln Leu Gln Gly Gly Leu Val Asp Gly
            260                 265                 270

Met Val Leu Arg Val Lys Phe Asn Ala Met Asn Thr Gly Ala Ser Thr
        275                 280                 285

Ile Asn Val Ser Gly Phe Gly Ser Lys Ala Ile Val Gly Ala Ala Asn
    290                 295                 300

Phe Pro Leu Thr Gly Gly Glu Leu Gly Gln Gly Leu Ile Ala Glu Leu
305                 310                 315                 320

Val Phe Asp Ala Thr Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
            340                 345                 350

Lys Gln Val Lys Asp Tyr Val Ala Ser Gln Lys Leu Thr Glu Val Asp
        355                 360                 365

Trp Ala Asp Val Val Asn Lys Pro Asn Val Ala Ile Gln Asp Thr Thr
    370                 375                 380

Pro Trp Phe Ala Asn Leu Glu Leu Ser Asp Ala Arg Pro Phe Ile Asp
385                 390                 395                 400

Phe His Phe Asn Asn Asn Arg Ala Lys Asp Phe Asp Tyr Arg Phe Ile
                405                 410                 415
```

```
Ser Glu Ala Asp Gly Ser Met Ala Phe Tyr Ser Arg Gln Gly Ser Ala
            420                 425                 430
Gly Pro Thr Gln Asp Ile Leu Phe Ser Arg Ser Asn Val Thr Phe Leu
            435                 440                 445
Gln Pro Arg Leu Asp Val Ala Lys Asn Leu Ala Tyr Ile Ala Asn Ser
450                 455                 460
Gly Pro Leu Trp Gln Asn Thr Thr Ala Asp Gln Pro Gly Trp Lys Phe
465                 470                 475                 480
Thr Phe Ala Gln Gly Val Asp Ala Asn Asn Asn Ala Val Ile Ala Val
            485                 490                 495
Asn Thr Thr Asn Pro Asp Gly Ser Tyr Arg Ser Gln Ile Met Arg Trp
            500                 505                 510
Asp Trp Ala Ser Thr Asn Val Ile Phe Asn Asn Arg Pro Leu Phe Ala
            515                 520                 525
Gly Gln Tyr Val Pro Trp Asp Ser Gly Asn Phe Asp Pro Ala Thr Lys
            530                 535                 540
Leu Thr Val Gly Thr Thr Asn Asn Ile Ser Gly Pro Thr Gly Ile Arg
545                 550                 555                 560
Asn Thr Thr Ser Asn Thr Gly Asn Met Asn Thr Trp Gly Ser Ser Ser
            565                 570                 575
Thr Thr Ala Ser Tyr Gly Asn Ala Ala Leu Gln Ile Phe Gly Arg Gly
            580                 585                 590
Gly Gly Glu Pro Ala Ala Ile Tyr Phe Asp Asn Ser Gln Thr Gly Trp
            595                 600                 605
Tyr Leu Gly Met Asp Lys Asp Gly Gln Leu Lys Arg Ala Gly Trp Ser
            610                 615                 620
Leu Gly Asn Asn Ser Tyr Val Val Thr Asp Glu Ser Asn Ile Arg Asn
625                 630                 635                 640
His Val Asn Gly Met Ser Gly Ala Pro Val Trp Gly Gly Gln Trp Phe
            645                 650                 655
Trp Gly Glu Trp Asn Phe Asn Pro Asn Thr Lys Leu Thr Ile Lys Ala
            660                 665                 670
Gly Thr Gln Glu Thr Ser Ser Thr Ala Ile Phe Ser Gly Thr Leu Pro
            675                 680                 685
Phe Ala Pro Ile Ala Ser Leu Ser Asp Tyr Ser Gln Ala Pro Leu Thr
690                 695                 700
Ile Tyr Asn Ser Pro Thr Gly Pro Ser Ala Lys Pro Ala Val Ile Ala
705                 710                 715                 720
Phe Ile Arg Pro Gly Asn Trp Gly Ala Phe Phe Gly Ile Asp Thr Asp
            725                 730                 735
Asn Lys Leu Lys Trp Gly Gly Gly Ser Leu Gly Asn Asn Ser Arg Glu
            740                 745                 750
Ile Ala Asp Ser Ser Asn Ile Met Asn Leu Trp Ala Ser Asn Pro Thr
            755                 760                 765
Ala Pro Ser Trp Asn Gly Gln Thr Val Trp Arg Ser Gly Asn Phe Asp
            770                 775                 780
Pro Ala Thr Lys Val Asp Leu Asn Ala Ala Asn Ala Thr Asn Gly Ser
785                 790                 795                 800
Met Ile Phe Asn Arg Ile Ser Gly Thr Gly Ser Gly Ile Ala Ser Ser
            805                 810                 815
Gly Arg Val Gly Ala Ile Asn Leu Gln Asn Gly Ala His Ser Gly Gln
            820                 825                 830
```

```
Ala Ala Ala Val Thr Phe Glu Arg Gly Gly Ser Ile Phe Val Asn Phe
            835                 840                 845

Gly Leu Asp Thr Asp Asn Val Leu Lys Val Gly Gly Asn Leu Gly
    850                 855                 860

Ala Asn Ala Tyr Pro Val Ile His Ala Gly Asn Tyr Asn Asn Tyr Ile
865                 870                 875                 880

Asn Gln Ala Leu Val Gln Val Gly Leu Gly Val Gly Ser Tyr Gly
                885                 890                 895

Ile Phe Ala Val Leu Asp Asn Ala Ala Pro Ile Ala Thr Val Gln Pro
            900                 905                 910

Gly Val Val Asp Gly Ser Ile Leu Ile Tyr Ser Ser Cys Ala Ala
    915                 920                 925

Asn Tyr Asn Ser Gly Gln Lys Pro Ala Gly Thr Trp Arg Cys Met Gly
    930                 935                 940

Tyr Val Val Asn Arg Asp Ala Asn Thr Ala Asp Ser Ala Thr Leu Phe
945                 950                 955                 960

Gln Arg Val Thr
```

<210> SEQ ID NO 28
<211> LENGTH: 964
<212> TYPE: PRT
<213> ORGANISM: Bacteriophage PB1

<400> SEQUENCE: 28

```
Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Ala Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
        115                 120                 125

Trp Ser Val Met Arg Ser Asn Ile Pro Met Pro Ala Gly Gly Pro Gly
    130                 135                 140

Leu Ser Ser Gly Gly Glu Val Ile Thr Thr Gly Arg Asn Phe Asn Asp
145                 150                 155                 160

Leu Leu Asn Gly Thr Trp Glu Phe Phe Ser Asp Ser Val Val Ala
                165                 170                 175

Ser Gln Asn Ala Pro Val Tyr Pro Ala Ser Gly Ala Ala Ala Gly
            180                 185                 190

Met Leu Glu Ala Lys Ser Trp Ile Ser Gly Ser Asn Thr Phe Cys Val
        195                 200                 205

Gln Arg Tyr Thr Asp Arg Val Gly Asn Val Ala Val Arg Gly Leu Asn
    210                 215                 220

Ala Gly Ala Trp Thr Asn Trp Met Tyr Ala Val Asn Val Met Ala Leu
225                 230                 235                 240
```

```
Gln Gln Gly Arg Val Thr Tyr Gly Val Ala Gly Ser Ala Asn Ala
            245                 250                 255

Tyr Thr Leu Thr Leu Val Pro Gln Leu Gln Gly Gly Leu Val Asp Gly
            260                 265                 270

Met Ile Leu Arg Val Lys Phe Asn Thr Val Asn Thr Gly Ala Ser Thr
            275                 280                 285

Ile Asn Val Ser Gly Phe Gly Ala Lys Ala Ile Val Gly Ala Ala Asn
            290                 295                 300

Phe Pro Leu Thr Gly Gly Glu Leu Gly Gln Gly Leu Ile Ala Glu Leu
305                 310                 315                 320

Val Phe Asp Ala Thr Gly Asp Arg Trp Arg Ile Leu Ala Gly Ala Pro
            325                 330                 335

Arg Ile Gln Val Gly Asn Ala Asp Gln Asp Tyr Gln Ala Pro Ser Trp
            340                 345                 350

Lys Gln Val Lys Asp Tyr Val Ala Ser Gln Lys Leu Thr Glu Val Asp
            355                 360                 365

Trp Ala Asp Val Val Asn Lys Pro Asn Val Ala Ile Gln Asp Thr Thr
            370                 375                 380

Pro Trp Phe Ala Asn Leu Glu Leu Ser Asp Ala Arg Pro Phe Ile Asp
385                 390                 395                 400

Phe His Phe Asn Asn Asn Arg Ala Lys Asp Phe Asp Tyr Arg Phe Ile
                    405                 410                 415

Ser Glu Ala Asp Gly Ser Met Ala Phe Tyr Ser Arg Gln Gly Ser Ala
                420                 425                 430

Gly Pro Thr Gln Asp Ile Leu Phe Ser Arg Ser Asn Val Thr Phe Leu
            435                 440                 445

Gln Pro Arg Leu Asp Val Ala Lys Asn Leu Ala Tyr Ile Ala Asn Ser
450                 455                 460

Gly Pro Leu Trp Gln Asn Thr Thr Ala Asp Gln Pro Gly Trp Lys Phe
465                 470                 475                 480

Thr Phe Ala Gln Gly Val Asp Ala Asn Asn Asn Ala Val Ile Ala Val
                485                 490                 495

Asn Thr Thr Asn Pro Asp Gly Ser Tyr Arg Ser Gln Val Met Arg Trp
            500                 505                 510

Asp Trp Ala Ser Thr Asn Val Ile Phe Asn Asn Arg Pro Leu Phe Ala
            515                 520                 525

Gly Gln Tyr Val Pro Trp Asp Ser Gly Asn Phe Asp Pro Ala Thr Lys
            530                 535                 540

Leu Thr Val Gly Thr Thr Asn Asn Ile Ser Gly Pro Thr Gly Ile Arg
545                 550                 555                 560

Asn Thr Thr Ser Asn Thr Gly Asn Met Asn Thr Trp Gly Ser Ser Ser
                565                 570                 575

Thr Thr Ala Ser Tyr Gly Asn Ala Ala Leu Gln Ile Phe Gly Arg Gly
                580                 585                 590

Gly Gly Glu Pro Ala Ala Ile Tyr Phe Asp Asn Ser Gln Thr Gly Trp
            595                 600                 605

Tyr Leu Gly Met Asp Lys Asp Gly Gln Leu Lys Arg Ala Gly Trp Ser
            610                 615                 620

Leu Gly Asn Asn Ser Tyr Val Val Thr Asp Glu Ser Asn Ile Arg Asn
625                 630                 635                 640

His Val Asn Gly Met Ser Gly Ala Pro Val Trp Gly Gly Gln Trp Phe
                645                 650                 655

Trp Gly Glu Trp Asn Phe Asn Pro Asn Thr Lys Leu Thr Ile Lys Ala
```

```
                    660                 665                 670
Gly Thr Gln Glu Thr Ser Ser Thr Ala Ile Phe Ser Gly Thr Leu Pro
                675                 680                 685

Phe Ala Pro Ile Ala Ser Leu Ser Asp Tyr Ser Gln Ala Pro Leu Thr
            690                 695                 700

Ile Tyr Asn Ser Pro Thr Gly Pro Ser Ala Lys Pro Ala Val Ile Ala
705                 710                 715                 720

Phe Ile Arg Pro Gly Asn Trp Gly Ala Phe Gly Ile Asp Thr Asp
                725                 730                 735

Asn Lys Leu Lys Trp Gly Gly Ser Leu Gly Asn Asn Ser Arg Glu
            740                 745                 750

Ile Ala Asp Ser Ser Asn Ile Met Asn Leu Trp Ala Ser Asn Pro Thr
                755                 760                 765

Ala Pro Ser Trp Asn Gly Gln Thr Val Trp Arg Ser Gly Asn Phe Asp
            770                 775                 780

Pro Ala Thr Lys Val Asp Leu Asn Ala Ala Asn Ala Thr Asn Gly Asn
785                 790                 795                 800

Met Ile Phe Asn Arg Ile Ser Gly Thr Gly Ser Gly Ile Ala Ser Ser
                805                 810                 815

Gly Arg Val Gly Ala Ile Asn Leu Gln Asn Gly Ala His Ser Gly Gln
            820                 825                 830

Ala Ala Ala Val Thr Phe Glu Arg Gly Gly Ser Ile Phe Val Asn Phe
                835                 840                 845

Gly Leu Asp Thr Asp Asn Val Leu Lys Val Gly Gly Gly Asn Leu Gly
            850                 855                 860

Ala Asn Ala Tyr Pro Val Ile His Ala Gly Asn Tyr Asn Asn Tyr Ile
865                 870                 875                 880

Asn Gln Ala Leu Val Gln Val Gly Leu Gly Gly Val Gly Ser Tyr Gly
                885                 890                 895

Ile Phe Ala Val Leu Asp Asn Ala Ala Pro Ile Ala Thr Val Gln Pro
            900                 905                 910

Gly Val Val Val Asp Gly Ser Ile Leu Ile Tyr Ser Ser Cys Ala Ala
                915                 920                 925

Asn Tyr Asn Ser Gly Gln Lys Pro Ala Gly Thr Trp Arg Cys Met Gly
            930                 935                 940

Tyr Val Val Asn Arg Asp Ala Asn Thr Pro Asp Ser Ala Thr Leu Phe
945                 950                 955                 960

Gln Arg Val Thr

<210> SEQ ID NO 29
<211> LENGTH: 964
<212> TYPE: PRT
<213> ORGANISM: Bacteriophage C36

<400> SEQUENCE: 29

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
                20                  25                  30

Asp Gly Tyr Thr Pro Asp Tyr Glu Ile Ser Leu Ala Ser Asn Asn Pro
            35                  40                  45

Gln Ala Lys Ala Val Glu Arg Lys Ile Gln Asn Gln Leu Phe Phe Ile
        50                  55                  60

Ala Thr Gln Asn Ala Gln Ala Trp Gln Arg Gln Met Ala Pro Pro Trp
```

-continued

```
         65                  70                  75                  80
Phe Gln Gly Met Pro Gly Gly Tyr Glu Gln Asn Ala Glu Val Val Arg
                 85                  90                  95
Val Gly Asn Asp Gly Ile Met Arg Arg Tyr Arg Ser Met Val Asn Ala
                100                 105                 110
Asn Ala Ser Asp Pro Leu Ser Thr Thr Trp Glu Gln Pro Ala
                115                 120                 125
Trp Ser Val Met Arg Ser Ser Ile Pro Met Pro Ala Gly Gly Pro Gly
130                 135                 140
Leu Ser Ser Gly Gly Glu Val Ile Thr Thr Gly Arg Asn Phe Asn Asp
145                 150                 155                 160
Leu Leu Asn Gly Thr Trp Glu Phe Phe Ser Asp Ser Val Val Ala
                165                 170                 175
Ser Gln Asn Ala Pro Val Tyr Pro Ala Ser Ala Gly Ala Ala Ala Gly
                180                 185                 190
Met Leu Glu Ala Lys Ser Trp Ile Ser Gly Ser Asn Thr Phe Cys Val
                195                 200                 205
Gln Arg Tyr Thr Asp Arg Val Gly Asn Val Ala Val Arg Gly Leu Asn
                210                 215                 220
Ala Gly Ala Trp Thr Asn Trp Met Tyr Ala Val Asn Val Met Ala Leu
225                 230                 235                 240
Gln Gln Gly Arg Val Thr Tyr Gly Val Ala Ala Gly Pro Ala Asn Ala
                245                 250                 255
Tyr Thr Leu Thr Leu Val Pro Gln Leu Gln Gly Gly Leu Val Asp Gly
                260                 265                 270
Met Ile Leu Arg Val Lys Phe Asn Thr Val Asn Thr Gly Ala Ser Thr
                275                 280                 285
Ile Asn Val Ser Gly Phe Gly Ala Lys Ala Ile Val Gly Ala Ala Asn
                290                 295                 300
Phe Pro Leu Thr Gly Gly Glu Leu Gly Gln Gly Leu Ile Ala Glu Leu
305                 310                 315                 320
Val Phe Asp Ala Thr Gly Asp Arg Trp Arg Ile Leu Ala Gly Ala Pro
                325                 330                 335
Arg Ile Gln Val Gly Asn Ala Asp Gln Asp Tyr Gln Ala Pro Ser Trp
                340                 345                 350
Lys Gln Val Lys Asp Tyr Val Ala Ser Gln Lys Leu Thr Glu Val Asp
                355                 360                 365
Trp Ala Asp Val Val Asn Lys Pro Asn Val Ala Ile Gln Asp Thr Thr
370                 375                 380
Pro Trp Phe Ala Asn Leu Glu Leu Ser Asp Ala Arg Pro Phe Ile Asp
385                 390                 395                 400
Phe His Phe Asn Asn Asn Arg Ala Lys Asp Phe Asp Tyr Arg Phe Ile
                405                 410                 415
Ser Glu Ala Asp Gly Ser Met Ala Phe Tyr Ser Arg Gln Gly Ser Ala
                420                 425                 430
Gly Pro Thr Gln Asp Ile Leu Phe Ser Arg Ser Asn Val Thr Phe Leu
                435                 440                 445
Gln Pro Arg Leu Asp Val Ala Lys Asn Leu Ala Tyr Ile Ala Asn Ser
                450                 455                 460
Gly Pro Leu Trp Gln Asn Thr Thr Ala Asp Gln Pro Gly Trp Lys Phe
465                 470                 475                 480
Thr Phe Ala Gln Gly Val Asp Ala Asn Asn Asn Ala Val Ile Ala Val
                485                 490                 495
```

-continued

Asn Thr Thr Asn Pro Asp Gly Ser Tyr Arg Ser Gln Ile Met Arg Trp
            500                 505                 510

Asp Trp Ala Ser Thr Asn Val Ile Phe Asn Asn Arg Pro Leu Phe Ala
        515                 520                 525

Gly Gln Tyr Val Pro Trp Asp Ser Gly Asn Phe Asp Pro Ala Thr Lys
    530                 535                 540

Leu Thr Val Gly Thr Thr Asn Asn Ile Ser Gly Pro Thr Gly Ile Arg
545                 550                 555                 560

Asn Thr Thr Ser Asn Thr Gly Asn Met Asn Thr Trp Gly Ser Ser Ser
            565                 570                 575

Thr Thr Ala Ser Tyr Gly Asn Ala Ala Val Gln Ile Phe Gly Arg Gly
        580                 585                 590

Asp Gly Glu Pro Ala Ala Ile Tyr Phe Asp Asn Ser Gln Thr Gly Trp
    595                 600                 605

Tyr Leu Gly Met Asp Lys Asp Gly Gln Leu Lys Arg Ala Gly Trp Ser
    610                 615                 620

Leu Gly Asn Asn Ser Tyr Val Val Thr Asp Glu Ser Asn Ile Arg Phe
625                 630                 635                 640

His Val Asn Ser Met Ala Gly Thr Pro Val Trp Gly Gly Asn Glu Phe
            645                 650                 655

Trp Gly Pro Trp Asn Phe Asn Pro Asn Thr Lys Leu Thr Ile Lys Ala
        660                 665                 670

Gly Thr Gln Glu Thr Ser Ser Thr Ala Ile Phe Ser Gly Thr Met Pro
    675                 680                 685

Phe Ala Pro Ile Ala Ser Leu Ser Asp Tyr Ser Gln Ala Pro Leu Thr
    690                 695                 700

Ile Tyr Asn Ser Pro Thr Gly Pro Ser Ala Lys Pro Ala Val Ile Ala
705                 710                 715                 720

Phe Ile Arg Pro Gly Asn Trp Gly Ala Phe Phe Gly Ile Asp Thr Asp
            725                 730                 735

Asn Lys Leu Lys Trp Gly Gly Ser Leu Gly Asn Ser Ser Arg Glu
        740                 745                 750

Ile Ala Asp Ser Ser Asn Ile Met Asn Leu Trp Ala Ala Asn Pro Thr
    755                 760                 765

Ala Pro Ser Trp Asn Gly Gln Thr Val Trp Arg Ser Gly Asn Phe Asp
    770                 775                 780

Pro Ala Thr Lys Val Asp Leu Asn Ala Ala Asn Ala Thr Asn Gly Asn
785                 790                 795                 800

Met Val Phe Asn Arg Ile Ser Gly Thr Gly Ser Gly Ile Ala Ser Ser
            805                 810                 815

Gly Arg Val Gly Ala Ile Asn Leu Gln Asn Gly Ala His Ser Gly Gln
        820                 825                 830

Ala Ala Ala Val Thr Phe Glu Arg Gly Gly Ser Ile Phe Val Asn Phe
    835                 840                 845

Gly Leu Asp Thr Asp Asn Val Leu Lys Val Gly Gly Asn Leu Gly
    850                 855                 860

Ala Asn Ala Tyr Pro Val Ile His Ala Gly Asn Tyr Asn Asn Tyr Ile
865                 870                 875                 880

Asn Gln Ala Leu Val Gln Val Gly Leu Gly Gly Val Gly Ser Tyr Gly
            885                 890                 895

Ile Phe Ala Val Leu Asp Asn Ala Ala Pro Ile Ala Thr Val Gln Pro
        900                 905                 910

```
Gly Val Val Asp Gly Ser Ile Leu Ile Tyr Ser Ser Cys Ser Ala
            915                 920                 925

Asn Tyr Asn Ser Gly Gln Arg Pro Ala Gly Thr Trp Arg Cys Met Gly
930                 935                 940

Tyr Val Val Asn Arg Asp Ala Asn Thr Pro Asp Ser Ala Thr Leu Phe
945                 950                 955                 960

Gln Arg Val Thr

<210> SEQ ID NO 30
<211> LENGTH: 964
<212> TYPE: PRT
<213> ORGANISM: Bacteriophage LBL3

<400> SEQUENCE: 30

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Ala Val Glu Arg Lys Ile Gln Asn Gln Leu Phe Phe Ile
50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
        115                 120                 125

Trp Ser Val Met Arg Ser Asn Ile Pro Met Pro Ala Gly Gly Pro Gly
130                 135                 140

Leu Ser Ser Gly Gly Glu Val Ile Thr Thr Gly Arg Asn Phe Asn Asp
145                 150                 155                 160

Leu Leu Asn Gly Thr Trp Glu Phe Phe Ser Asp Ser Val Val Ile Ala
                165                 170                 175

Ser Gln Asn Ala Pro Val Tyr Pro Ala Ser Gly Ala Ala Ala Gly
            180                 185                 190

Met Leu Glu Ala Lys Ser Trp Val Ser Gly Ala Asn Thr Phe Cys Val
        195                 200                 205

Gln Arg Tyr Thr Asp Arg Val Gly Asn Val Ala Val Arg Gly Leu Asn
210                 215                 220

Ala Gly Ala Trp Thr Asn Trp Met Tyr Ala Val Asn Val Met Ala Leu
225                 230                 235                 240

Gln Gln Gly Arg Val Thr Tyr Gly Val Ala Ala Gly Ser Ala Asn Ala
                245                 250                 255

Tyr Thr Leu Thr Leu Val Pro Gln Leu Gln Gly Gly Leu Val Asp Gly
            260                 265                 270

Met Ile Leu Arg Val Lys Phe Asn Thr Met Asn Thr Gly Ala Ser Thr
        275                 280                 285

Ile Asn Val Ser Gly Phe Gly Ala Lys Ala Ile Val Gly Ala Ala Asn
290                 295                 300

Phe Pro Leu Thr Gly Gly Glu Leu Gly Gln Gly Leu Ile Ala Glu Leu
305                 310                 315                 320
```

```
Val Phe Asp Ala Thr Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
            340                 345                 350

Lys Gln Val Lys Asp Tyr Val Ala Ser Gln Lys Leu Thr Glu Val Asp
        355                 360                 365

Trp Ala Asp Val Val Asn Lys Pro Asn Val Ala Ile Gln Asp Thr Thr
370                 375                 380

Pro Trp Phe Ala Asn Leu Glu Leu Ser Asp Ala Arg Pro Phe Ile Asp
385                 390                 395                 400

Phe His Phe Asn Asn Arg Ala Lys Asp Phe Asp Tyr Arg Phe Ile
                405                 410                 415

Ser Glu Ala Asp Gly Ser Met Ala Phe Tyr Ser Arg Gln Gly Ser Ala
                420                 425                 430

Gly Pro Thr Gln Asp Ile Leu Phe Ser Arg Ser Asn Val Thr Phe Leu
            435                 440                 445

Gln Pro Arg Leu Asp Val Ala Lys Asn Leu Ala Tyr Ile Ala Asn Ser
        450                 455                 460

Gly Pro Leu Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
                485                 490                 495

Asn Thr Thr Asn Pro Asp Gly Ser Tyr Arg Ser Gln Ile Met Arg Trp
                500                 505                 510

Asp Trp Ala Ser Thr Asn Val Ile Phe Asn Asn Arg Pro Leu Phe Ala
            515                 520                 525

Gly Gln Tyr Val Pro Trp Asp Ser Gly Asn Phe Asp Pro Ala Thr Lys
        530                 535                 540

Leu Thr Val Gly Thr Thr Asn Asn Ile Ser Arg Pro Thr Gly Ile Arg
545                 550                 555                 560

Asn Thr Thr Ser Asn Thr Gly Asn Met Asn Thr Trp Gly Ser Ser Ser
                565                 570                 575

Thr Thr Ala Ser Tyr Gly Asn Ala Ala Leu Gln Ile Phe Gly Arg Gly
                580                 585                 590

Gly Gly Glu Pro Ala Ala Ile Tyr Phe Asp Asn Ser Gln Thr Gly Trp
            595                 600                 605

Tyr Leu Gly Met Asp Lys Asp Gly Gln Leu Lys Arg Ala Gly Trp Ser
        610                 615                 620

Leu Gly Asn Asn Ser Tyr Val Val Thr Asp Glu Ser Asn Ile Arg Phe
625                 630                 635                 640

His Val Asn Ser Met Ala Gly Thr Pro Val Trp Gly Gly Asn Glu Phe
                645                 650                 655

Trp Gly Pro Trp Asn Phe Asn Pro Asn Thr Lys Leu Thr Ile Lys Ala
                660                 665                 670

Gly Thr Gln Glu Thr Ser Ser Thr Ala Ile Phe Ser Thr Met Pro
            675                 680                 685

Phe Ala Pro Ile Ala Ser Leu Ser Asp Tyr Ser Gln Ala Pro Leu Thr
        690                 695                 700

Val Tyr Asn Ser Pro Thr Gly Pro Ser Ala Lys Pro Ala Val Ile Ala
705                 710                 715                 720

Phe Ile Arg Pro Gly Asn Trp Ala Phe Phe Gly Ile Asp Thr Asp
                725                 730                 735

Asn Lys Leu Lys Trp Gly Gly Gly Ser Leu Gly Asn Ser Ser Arg Glu
```

```
            740                 745                 750
Ile Ala Asp Ser Ser Asn Ile Met Asn Leu Trp Ala Ala Asn Pro Thr
            755                 760                 765
Ala Pro Thr Trp Asn Gly Gln Thr Ile Trp Arg Ser Gly Asn Phe Asp
            770                 775                 780
Pro Ala Thr Lys Val Asp Leu Asn Ala Ala Asn Ala Thr Asn Gly Asn
785                 790                 795                 800
Met Ile Phe Asn Arg Ile Ala Gly Thr Gly Ser Gly Ile Ala Ser Ser
            805                 810                 815
Asp Arg Val Gly Ala Ile Ser Leu Gln Asn Gly Ala Thr Ala Gly Ala
            820                 825                 830
Ala Ala Ala Val Thr Phe Glu Arg Gly Gly Gly Phe Phe Val Asn Phe
            835                 840                 845
Gly Leu Asp Thr Asp Asn Val Leu Lys Val Gly Gly Asn Leu Gly
            850                 855                 860
Ala Asn Ala Tyr Pro Val Ile His Ala Gly Asn Tyr Asn Asn Tyr Ile
865                 870                 875                 880
Asn Gln Ala Leu Val Gln Val Gly Leu Gly Gly Val Gly Ser Tyr Gly
            885                 890                 895
Ile Phe Ala Val Leu Asp Tyr Ala Ala Pro Thr Ala Thr Val Gln Pro
            900                 905                 910
Gly Val Ile Val Asp Gly Ser Ile Leu Ile Tyr Ser Ser Cys Ser Ala
            915                 920                 925
His Tyr Asn Ser Gly Gln Arg Pro Ala Gly Thr Trp Arg Cys Met Gly
            930                 935                 940
Tyr Val Leu Asn Arg Asp Ala Arg Asp Pro Asp Ser Ala Thr Leu Phe
945                 950                 955                 960
Gln Arg Val Thr

<210> SEQ ID NO 31
<211> LENGTH: 964
<212> TYPE: PRT
<213> ORGANISM: Bacteriophage Phi33

<400> SEQUENCE: 31

Met Ile Thr Pro Glu Leu Ile Pro Ser Pro Phe Ala Ala Gln Gly Asp
1               5                   10                  15
Lys Asp Pro Ile Pro Gln Thr Ser Ser Thr Gly Phe Ala Asn Leu Arg
            20                  25                  30
Asp Gly Tyr Thr Pro Asp Tyr Glu Ile Ser Leu Ala Ser Asn Asn Pro
            35                  40                  45
Gln Ala Lys Ala Val Glu Arg Lys Ile Gln Asn Gln Leu Phe Phe Ile
        50                  55                  60
Ala Thr Gln Asn Ala Gln Ala Trp Gln Arg Gln Met Ala Pro Pro Trp
65              70                  75                  80
Phe Gln Gly Met Pro Gly Gly Tyr Glu Gln Asn Ala Glu Val Val Arg
            85                  90                  95
Val Gly Asn Asp Gly Ile Met Arg Arg Tyr Arg Ser Met Val Asn Ala
            100                 105                 110
Asn Ala Ile Asp Pro Leu Ser Thr Thr Trp Glu Gln Pro Ala
            115                 120                 125
Trp Ser Val Met Arg Ser Asn Ile Pro Met Pro Ala Gly Gly Pro Gly
            130                 135                 140
Leu Ser Ser Gly Gly Glu Val Ile Thr Thr Gly Arg Asn Phe Asn Asp
```

```
            145                 150                 155                 160
Leu Leu Asn Gly Thr Trp Glu Phe Phe Ser Asp Ser Val Val Ala
            165                 170                 175
Ser Gln Asn Ala Pro Val Tyr Pro Ala Ser Ala Gly Ala Ala Gly
            180                 185                 190
Met Leu Glu Ala Lys Ser Trp Val Ser Gly Ala Asn Thr Phe Cys Val
            195                 200                 205
Gln Arg Tyr Thr Asp Arg Val Gly Asn Val Ala Val Arg Gly Leu Asn
210                 215                 220
Ala Gly Ala Trp Thr Asn Trp Met Tyr Ala Val Asn Val Met Ala Leu
225                 230                 235                 240
Gln Gln Gly Arg Val Thr Tyr Gly Val Ala Ala Gly Ser Ala Asn Ala
            245                 250                 255
Tyr Thr Leu Thr Leu Val Pro Gln Leu Gln Gly Gly Leu Val Asp Gly
            260                 265                 270
Met Ile Leu Arg Val Lys Phe Asn Thr Met Asn Thr Gly Ala Ser Thr
            275                 280                 285
Ile Asn Val Ser Gly Leu Gly Ala Lys Ala Ile Val Gly Ala Ala Asn
            290                 295                 300
Phe Pro Leu Thr Gly Gly Glu Leu Gly Gln Gly Leu Ile Ala Glu Leu
305                 310                 315                 320
Val Phe Asp Ala Ala Gly Asp Arg Trp Arg Ile Leu Ala Gly Ala Pro
            325                 330                 335
Arg Ile Gln Val Gly Asn Ala Asp Gln Asp Tyr Gln Ala Pro Ser Trp
            340                 345                 350
Lys Gln Val Lys Asp Tyr Val Ala Ser Gln Lys Leu Thr Glu Val Asp
            355                 360                 365
Trp Ala Asp Val Val Asn Lys Pro Asn Val Ala Ile Gln Asp Thr Thr
            370                 375                 380
Pro Trp Phe Ala Asn Leu Glu Leu Ser Asp Ala Arg Pro Phe Ile Asp
385                 390                 395                 400
Phe His Phe Asn Ser Asn Arg Ala Lys Asp Phe Asp Tyr Arg Leu Ile
            405                 410                 415
Ser Glu Ala Asp Gly Ser Leu Ala Phe Tyr Ser Arg Gln Gly Ser Ala
            420                 425                 430
Gly Pro Thr Gln Asp Ile Leu Phe Asn Arg Asn Ser Val Thr Phe Phe
            435                 440                 445
Gln Pro Arg Leu Asp Val Ala Lys Asn Leu Ala Tyr Ile Ala Asn Ser
            450                 455                 460
Gly Pro Leu Trp Gln Asn Thr Thr Ala Asp Gln Pro Gly Trp Lys Phe
465                 470                 475                 480
Thr Phe Ala Gln Gly Val Asp Ala Asn Asn Ala Val Ile Ala Val
            485                 490                 495
Asn Thr Thr Asn Pro Asp Gly Ser Tyr Arg Ser Gln Ile Met Arg Trp
            500                 505                 510
Asp Trp Ala Ser Thr Asn Val Ile Phe Asn Asn Arg Pro Leu Phe Ala
            515                 520                 525
Gly Gln Tyr Val Pro Trp Asp Ser Gly Asn Phe Asp Pro Ser Thr Lys
            530                 535                 540
Leu Thr Val Asn Ala Thr Asn Gln Ile Ala Gly Pro Thr Gly Ile Arg
545                 550                 555                 560
Asn Thr Asn Gly Asn Thr Gly Asn Met Asn Thr Trp Gly Ser Gly Ser
            565                 570                 575
```

```
Thr Thr Ala Ser Tyr Gly Asn Ala Ala Leu Gln Ile Phe Gly Lys Gly
            580                 585                 590

Gly Gly Glu Pro Ala Ala Leu Tyr Phe Asp Asn Ser Gln Thr Gly Trp
        595                 600                 605

Tyr Leu Gly Met Asp Lys Asp Gly Gln Leu Lys Arg Ala Gly Trp Ser
    610                 615                 620

Leu Gly Asn Asn Ala Tyr Val Ile Thr Asp Glu Ser Asn Ile Arg Phe
625                 630                 635                 640

His Val Asn Ser Met Ala Gly Thr Pro Val Trp Gly Asn Glu Phe
                645                 650                 655

Trp Gly Pro Trp Asn Phe Asn Pro Asn Thr Lys Leu Thr Ile Lys Ala
            660                 665                 670

Gly Thr Gln Glu Thr Ser Ser Thr Ala Ile Phe Ser Gly Thr Met Pro
        675                 680                 685

Phe Ala Pro Ile Ala Ser Leu Ser Asp Tyr Ser Gln Ala Pro Leu Thr
    690                 695                 700

Val Tyr Asn Ala Pro Thr Gly Pro Ser Ala Lys Pro Ala Val Ile Ala
705                 710                 715                 720

Phe Ile Arg Pro Gly Asn Trp Gly Ala Phe Phe Gly Ile Asp Thr Asp
                725                 730                 735

Asn Lys Leu Lys Trp Gly Gly Gly Ser Leu Gly Asn Ser Ser Arg Glu
            740                 745                 750

Ile Ala Asp Ser Ser Asn Ile Met Asn Leu Trp Ala Ala Asn Pro Thr
        755                 760                 765

Ala Pro Ser Trp Asn Gly Gln Thr Ile Trp Arg Ser Gly Asn Phe Asp
    770                 775                 780

Pro Ala Thr Lys Val Asp Leu Asn Ala Ala Asn Ala Thr Asn Gly Asn
785                 790                 795                 800

Met Ile Phe Asn Arg Ile Ala Gly Thr Gly Ser Gly Ile Ala Ser Ser
                805                 810                 815

Gly Arg Val Gly Ala Ile Asn Leu Gln Asn Gly Glu His Ser Gly Gln
            820                 825                 830

Ala Ala Ala Val Thr Phe Glu Arg Gly Gly Ser Ile Phe Val Asn Phe
        835                 840                 845

Gly Leu Asp Thr Asp Asn Val Leu Lys Val Gly Gly Asn Leu Gly
    850                 855                 860

Ala Asn Ala Tyr Pro Val Ile His Ala Gly Asn Tyr Asn Tyr Ile
865                 870                 875                 880

Asn Gln Ala Leu Val Gln Val Gly Leu Glu Gly Val Gly Ser Tyr Gly
                885                 890                 895

Ile Phe Ala Val Leu Asp Asn Ala Ala Pro Thr Ala Thr Val Gln Pro
            900                 905                 910

Gly Val Val Val Asp Gly Ser Ile Leu Ile Tyr Ser Ser Cys Ala Ala
        915                 920                 925

Asn Tyr Asn Ser Gly Lys Arg Pro Ala Gly Thr Trp Arg Cys Met Gly
    930                 935                 940

Tyr Val Val Asn Arg Asp Ala Asn Thr Pro Asp Ser Ala Thr Leu Phe
945                 950                 955                 960

Gln Arg Val Thr

<210> SEQ ID NO 32
<211> LENGTH: 964
<212> TYPE: PRT
```

<213> ORGANISM: Bacteriophage LMA2

<400> SEQUENCE: 32

```
Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Val Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
        115                 120                 125

Trp Ser Ala Met Arg Ser Asn Ile Pro Met Pro Ala Gly Gly Pro Gly
130                 135                 140

Leu Ser Ser Gly Gly Glu Val Ile Thr Gly Arg Asn Phe Asn Asp
145                 150                 155                 160

Leu Leu Asn Gly Thr Trp Glu Phe Phe Ser Asp Ser Val Val Ile Ala
                165                 170                 175

Ser Gln Asn Ala Pro Val Tyr Pro Ala Ser Ala Gly Ala Ala Ala Gly
            180                 185                 190

Met Leu Glu Ala Lys Ser Trp Val Ser Gly Ala Asn Thr Phe Cys Val
        195                 200                 205

Gln Arg Tyr Thr Asp Arg Val Gly Asn Val Ala Val Arg Gly Leu Asn
    210                 215                 220

Ala Gly Ala Trp Thr Asn Trp Met Tyr Ala Val Asn Val Met Ala Leu
225                 230                 235                 240

Gln Gln Gly Arg Val Thr Tyr Gly Val Ala Ala Gly Ser Ala Asn Ala
                245                 250                 255

Tyr Thr Leu Thr Leu Val Pro Gln Leu Gln Gly Gly Leu Val Asp Gly
            260                 265                 270

Met Ile Leu Arg Val Lys Phe Asn Thr Met Thr Asn Thr Gly Ala Thr Thr
        275                 280                 285

Ile Asn Val Ser Gly Leu Gly Ala Lys Ala Ile Val Gly Ala Ala Asn
    290                 295                 300

Phe Pro Leu Thr Gly Gly Glu Leu Gly Gln Gly Leu Ile Ala Glu Leu
305                 310                 315                 320

Val Phe Asp Ala Ala Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
            340                 345                 350

Lys Gln Val Lys Asp Tyr Val Ala Ser Gln Lys Leu Thr Glu Val Asp
        355                 360                 365

Trp Ala Asp Val Val Asn Lys Pro Asn Val Ala Ile Gln Asp Thr Thr
    370                 375                 380

Pro Trp Phe Ala Asn Leu Glu Leu Ser Asp Ala Arg Pro Phe Ile Asp
385                 390                 395                 400
```

-continued

```
Phe His Phe Asn Ser Asn Arg Ala Lys Asp Phe Asp Tyr Arg Leu Ile
                405                 410                 415
Ser Glu Ala Asp Gly Ser Leu Ala Phe Tyr Ser Arg Gln Gly Ser Ala
            420                 425                 430
Gly Pro Thr Gln Asp Ile Leu Phe Asn Arg Asn Ser Val Thr Phe Phe
        435                 440                 445
Gln Pro Arg Leu Asp Val Ala Lys Asn Leu Ala Tyr Ile Ala Asn Ser
    450                 455                 460
Gly Pro Leu Trp Gln Asn Thr Thr Ala Asp Gln Pro Gly Trp Lys Phe
465                 470                 475                 480
Thr Phe Ala Gln Gly Val Asp Ala Asn Asn Ala Val Ile Ala Val
                485                 490                 495
Asn Thr Thr Asn Pro Asp Gly Ser Tyr Arg Ser Gln Val Met Arg Trp
                500                 505                 510
Asp Trp Ala Ser Thr Asn Val Ile Phe Asn Asn Arg Pro Leu Phe Ala
            515                 520                 525
Gly Gln Tyr Thr Pro Trp Asp Ser Gly Asn Phe Asp Pro Ser Thr Lys
        530                 535                 540
Leu Thr Val Asn Ala Thr Asn Gln Ile Ala Gly Pro Thr Gly Ile Arg
545                 550                 555                 560
Asn Thr Asn Gly Asn Thr Gly Asn Met Asn Thr Trp Gly Ser Gly Ser
                565                 570                 575
Thr Thr Ala Ser Tyr Gly Asn Ala Ala Ile Gln Ile Phe Gly Lys Gly
            580                 585                 590
Gly Gly Glu Pro Ala Ala Ile Tyr Phe Asp Asn Ser Gln Thr Gly Trp
        595                 600                 605
Tyr Leu Gly Met Asp Lys Asp Gly Gln Leu Lys Arg Ala Gly Trp Ser
    610                 615                 620
Leu Gly Asn Asn Ser Tyr Val Ile Thr Asp Glu Leu Asn Ile Arg Asn
625                 630                 635                 640
His Ile Asn Gly Met Ala Ala Arg Pro Val Trp Gly Gly Asn Glu Phe
                645                 650                 655
Trp Gly Pro Trp Asn Phe Asn Pro Asn Thr Lys Leu Thr Ile Lys Ala
            660                 665                 670
Gly Thr Gln Glu Thr Ser Ser Thr Ala Ile Tyr Ser Gly Thr Met Pro
        675                 680                 685
Phe Ala Pro Ile Ala Ser Leu Ser Asp Tyr Ser Gln Ala Pro Leu Thr
    690                 695                 700
Ile Tyr Asn Ala Pro Thr Gly Pro Ser Ala Lys Pro Ala Val Ile Ala
705                 710                 715                 720
Phe Ile Arg Pro Gly Asn Trp Gly Ala Phe Phe Gly Leu Asp Thr Asp
                725                 730                 735
Asn Lys Leu Lys Trp Gly Gly Ser Leu Gly Asn Ser Ser Met Glu
            740                 745                 750
Ile Ala Asp Ser Ser Asn Ile Met Asn Leu Trp Ala Ala Asn Pro Thr
        755                 760                 765
Ala Pro Thr Trp Asn Gly Gln Thr Val Trp Arg Ser Gly Asn Phe Asp
    770                 775                 780
Pro Ala Thr Lys Val Asp Leu Asn Ala Pro Asn Ala Thr Asn Gly Asn
785                 790                 795                 800
Met Ile Phe Asn Arg Ile Ala Gly Thr Gly Ser Gly Ile Ala Ser Ser
                805                 810                 815
Gly Arg Val Gly Ala Ile Ser Leu Gln Asn Gly Ala Thr Ala Gly Ala
```

```
                820                 825                 830
Ala Ala Ala Val Thr Phe Glu Arg Gly Gly Phe Val Asn Phe
            835                 840                 845

Gly Leu Asp Thr Asp Asn Val Leu Lys Val Gly Gly Asn Leu Gly
850                 855                 860

Ala Asn Ala Tyr Pro Val Ile His Ala Gly Asn Tyr Asn Ser Tyr Ile
865                 870                 875                 880

Asn Gln Ala Leu Val Gln Val Gly Leu Gly Val Gly Ser Tyr Ala
                885                 890                 895

Ala Leu Ala Val Tyr Asp Thr Ser Ala Pro Ala Ser Ser Val Gly Pro
            900                 905                 910

Gly Thr Ile Leu Asp Gly Ser Val Leu Phe Tyr Ser Ser Phe Asn Ala
            915                 920                 925

Asn Phe Arg Ser Gly Thr Lys Pro Thr Gly Thr Trp Arg Cys Met Gly
            930                 935                 940

Tyr Ile Leu Asn Arg Asp Gly Thr Asn Pro Asp Ser Ala Thr Leu Phe
945                 950                 955                 960

Gln Arg Val Thr

<210> SEQ ID NO 33
<211> LENGTH: 963
<212> TYPE: PRT
<213> ORGANISM: Bacteriophage KPP12

<400> SEQUENCE: 33

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Ala Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
        115                 120                 125

Trp Ser Ala Met Arg Ser Asn Ile Pro Met Pro Ala Gly Gly Pro Gly
    130                 135                 140

Leu Ser Ser Gly Gly Glu Val Ile Thr Thr Gly Arg Asn Phe Asn Asp
145                 150                 155                 160

Leu Leu Asn Gly Thr Trp Glu Phe Phe Ser Asp Ser Val Val Ile Ala
                165                 170                 175

Ser Gln Asn Ala Pro Val Tyr Pro Ala Ser Gly Ala Ala Ala Gly
            180                 185                 190

Met Leu Glu Ala Lys Ser Trp Val Ser Gly Ala Asn Thr Phe Cys Val
        195                 200                 205

Gln Arg Tyr Thr Asp Arg Val Gly Asn Val Ala Leu Arg Gly Leu Asn
    210                 215                 220

Ala Gly Ala Trp Thr Asn Trp Met Tyr Ala Val Asn Val Met Ala Leu
```

```
            225                 230                 235                 240
Gln Gln Gly Arg Val Thr Tyr Gly Val Ala Ala Gly Ser Ala Asn Ala
                245                 250                 255

Tyr Thr Leu Thr Leu Val Pro Gln Leu Gln Gly Gly Leu Val Asp Gly
                260                 265                 270

Met Ile Leu Arg Val Lys Phe Asn Thr Met Asn Thr Gly Ala Ser Thr
                275                 280                 285

Ile Asn Val Ser Gly Leu Gly Ala Lys Ala Ile Val Gly Ala Ala Asn
            290                 295                 300

Phe Pro Leu Thr Gly Gly Glu Leu Gly Gln Gly Leu Ile Ala Glu Leu
305                 310                 315                 320

Val Phe Asp Ala Ala Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
                340                 345                 350

Lys Gln Val Lys Asp Tyr Val Ala Ser Gln Lys Leu Thr Glu Val Asp
                355                 360                 365

Trp Ala Asp Val Val Asn Lys Pro Asn Val Ala Ile Gln Asp Thr Thr
            370                 375                 380

Pro Trp Phe Ala Asn Leu Glu Leu Ser Asp Ala Arg Pro Phe Ile Asp
385                 390                 395                 400

Phe His Phe Asn Asn Arg Ala Lys Asp Phe Asp Tyr Arg Phe Ile
                405                 410                 415

Ser Glu Ala Asp Gly Ser Met Ala Phe Tyr Ser Arg Gln Gly Ser Ala
                420                 425                 430

Gly Pro Thr Gln Asp Ile Leu Phe Ser Arg Ser Asn Val Thr Phe Leu
                435                 440                 445

Gln Pro Arg Leu Asp Val Ala Lys Asn Leu Ala Tyr Ile Ala Asn Ser
                450                 455                 460

Gly Ser Leu Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
                485                 490                 495

Asn Thr Thr Asn Pro Asp Gly Ser Tyr Arg Ser Gln Ile Met Arg Trp
                500                 505                 510

Asp Trp Ala Ser Thr Asn Val Ile Phe Asn Asn Arg Pro Leu Phe Ala
                515                 520                 525

Gly Gln Tyr Thr Pro Trp Asp Ser Gly Asn Phe Asp Pro Ser Thr Lys
                530                 535                 540

Leu Thr Val Asn Ala Thr Asn Gln Ile Ala Gly Pro Thr Gly Ile Arg
545                 550                 555                 560

Asn Thr Asn Gly Asn Thr Gly Asn Met Asn Thr Trp Gly Ser Ser Ser
                565                 570                 575

Thr Thr Ala Ser Tyr Gly Asn Ala Ala Leu Gln Ile Phe Gly Lys Gly
                580                 585                 590

Gly Gly Glu Pro Ala Ala Leu Tyr Phe Asp Asn Ser Gln Thr Gly Trp
                595                 600                 605

Tyr Leu Gly Met Asp Lys Asp Gly Gln Leu Lys Arg Ala Gly Trp Ser
                610                 615                 620

Leu Gly Asn Asn Ala Tyr Val Ile Thr Asp Glu Ser Asn Ile Arg Phe
625                 630                 635                 640

His Val Asn Ser Met Ala Gly Thr Pro Val Trp Gly Gly Asn Glu Phe
                645                 650                 655
```

```
Trp Gly Ser Trp Asn Phe Asn Pro Asn Thr Lys Leu Thr Ile Lys Ala
            660                 665                 670

Gly Thr Gln Glu Thr Ser Ser Thr Ala Ile Phe Ser Glu Thr Met Pro
            675                 680                 685

Phe Ala Pro Ile Ala Ser Leu Ser Asp Tyr Ser Gln Ala Pro Leu Thr
            690                 695                 700

Ile Tyr Asn Ala Pro Thr Gly Pro Ser Ala Lys Pro Ala Val Ile Ala
705                 710                 715                 720

Phe Ile Arg Pro Gly Asn Trp Gly Ala Phe Phe Gly Leu Asp Thr Asp
            725                 730                 735

Asn Lys Leu Lys Trp Gly Gly Ser Leu Gly Asn Ser Ser Arg Glu
            740                 745                 750

Ile Ala Asp Ser Arg Asn Ile Met Asn Leu Trp Ala Ala Asn Pro Thr
            755                 760                 765

Ala Pro Thr Trp Asn Gly Gln Thr Val Trp Arg Ser Gly Asn Phe Asp
            770                 775                 780

Pro Ala Thr Lys Val Asp Leu Asn Ala Pro Asn Ala Thr Asn Gly Asn
785                 790                 795                 800

Met Ile Phe Asn Arg Ile Ala Gly Thr Gly Ser Gly Ile Ala Ser Ser
            805                 810                 815

Gly Arg Val Gly Ala Ile Ser Leu Gln Asn Gly Ala Thr Ala Gly Ala
            820                 825                 830

Ala Ala Ala Val Thr Phe Glu Arg Gly Gly Phe Phe Val Asn Phe Gly
            835                 840                 845

Leu Asp Thr Asp Asn Val Leu Lys Val Gly Gly Gly Asn Leu Gly Ala
            850                 855                 860

Asn Ala Tyr Pro Val Ile His Ala Gly Asn Tyr Asn Ser Tyr Ile Asn
865                 870                 875                 880

Gln Ala Leu Val Gln Val Gly Leu Gly Gly Val Gly Ser Tyr Ala Ala
            885                 890                 895

Leu Ala Val Tyr Asp Thr Ser Ala Pro Ala Ser Ser Val Gly Pro Gly
            900                 905                 910

Thr Ile Leu Asp Gly Ser Val Leu Phe Tyr Ser Ser Phe Asp Ala Asn
            915                 920                 925

Phe Arg Ser Gly Thr Lys Pro Thr Gly Thr Trp Arg Cys Met Gly Tyr
            930                 935                 940

Val Leu Asn Arg Asp Gly Thr Asn Pro Asp Ser Ala Ala Leu Phe Gln
945                 950                 955                 960

Arg Val Thr
```

<210> SEQ ID NO 34
<211> LENGTH: 962
<212> TYPE: PRT
<213> ORGANISM: Bacteriophage JG024

<400> SEQUENCE: 34

```
Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
            35                  40                  45

Gln Ala Lys Ala Val Glu Arg Lys Ile Gln Asn Gln Leu Phe Phe Ile
            50                  55                  60
```

```
Ala Thr Gln Asn Ala Gln Ala Trp Gln Arg Gln Met Ala Pro Pro Trp
 65                  70                  75                  80

Phe Gln Gly Met Pro Gly Gly Tyr Glu Gln Asn Ala Glu Val Val Arg
                 85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
        115                 120                 125

Trp Ser Val Met Arg Thr Asn Ile Pro Met Pro Ala Gly Gly Pro Gly
130                 135                 140

Leu Ser Ser Gly Gly Glu Val Ile Thr Thr Gly Arg Asn Phe Asn Glu
145                 150                 155                 160

Leu Leu Asn Gly Thr Trp Glu Phe Phe Ser Asp Ala Ile Val Val Ala
                165                 170                 175

Ser Gln Asn Ala Pro Val Tyr Pro Ala Ser Ala Gly Ala Ala Ala Gly
            180                 185                 190

Met Leu Glu Ala Lys Ser Trp Val Ser Gly Ser Asn Thr Phe Cys Val
        195                 200                 205

Gln Arg Tyr Thr Asp Arg Val Gly Asn Val Ala Val Arg Gly Leu Asn
210                 215                 220

Ala Gly Ala Trp Thr Asn Trp Met Tyr Ala Val Asn Val Met Ala Leu
225                 230                 235                 240

Gln His Gly Arg Val Thr Tyr Gly Thr Ala Ala Gly Pro Ala Asn Ala
                245                 250                 255

Tyr Thr Leu Thr Leu Val Pro Gln Ile Gln Gly Gly Leu Val Asp Gly
            260                 265                 270

Met Ile Leu Arg Val Lys Phe Asn Thr Met Asn Thr Gly Ala Thr Thr
        275                 280                 285

Ile Asn Val Ser Gly Leu Gly Ala Lys Ala Ile Val Gly Ala Ala Asn
290                 295                 300

Phe Pro Leu Thr Gly Gly Glu Leu Gly Gln Gly Leu Ile Ala Glu Leu
305                 310                 315                 320

Val Phe Asp Ala Ala Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
            340                 345                 350

Lys Gln Val Lys Asp Tyr Val Glu Ser Gln Lys Leu Thr Glu Val Asp
        355                 360                 365

Trp Thr Asp Val Val Asn Lys Pro Asn Val Ala Ile Gln Asp Thr Thr
370                 375                 380

Pro Trp Phe Ala Asn Leu Glu Leu Ser Asp Ala Arg Pro Phe Ile Asp
385                 390                 395                 400

Phe His Phe Asn Ser Asn Arg Ala Lys Asp Phe Asp Tyr Arg Leu Ile
                405                 410                 415

Ser Glu Ala Asp Gly Ser Leu Ala Phe Tyr Ser Arg Gln Gly Ser Ala
            420                 425                 430

Gly Pro Thr Gln Asp Ile Leu Phe Asn Arg Asn Ser Val Thr Phe Phe
        435                 440                 445

Gln Pro Arg Leu Asp Val Ala Lys Asn Leu Ala Tyr Ile Ala Asn Ser
        450                 455                 460

Gly Pro Leu Trp Gln Asn Thr Thr Ala Asp Gln Pro Gly Trp Lys Phe
465                 470                 475                 480
```

```
Thr Phe Ala Gln Gly Val Asp Ala Asn Asn Asn Ala Val Ile Ala Val
            485                 490                 495

Asn Thr Thr Asn Pro Asp Gly Ser Tyr Arg Ser Gln Val Met Arg Trp
        500                 505                 510

Asp Trp Ala Ser Thr Asn Val Ile Phe Asn Asn Arg Pro Leu Phe Ala
        515                 520                 525

Gly Gln Tyr Thr Pro Trp Asp Ser Gly Asn Phe Asp Pro Ser Thr Lys
        530                 535                 540

Leu Thr Val Ser Ala Thr Asn Gln Ile Ser Gly Pro Thr Gly Ile Arg
545                 550                 555                 560

Asn Thr Asn Gly Asn Thr Gly Asn Met Asn Thr Trp Gly Ser Gly Ser
                565                 570                 575

Thr Thr Ala Ser Tyr Gly Asn Ala Ala Ile Gln Ile Phe Gly Lys Gly
            580                 585                 590

Gly Gly Glu Pro Ala Ala Ile Tyr Phe Asp Asn Ser Gln Thr Gly Trp
        595                 600                 605

Tyr Leu Gly Met Asp Lys Asp Gly Gln Leu Lys Arg Ala Gly Trp Ser
        610                 615                 620

Leu Gly Asn Asn Ser Tyr Val Ile Thr Asp Glu Ser Asn Ile Arg Thr
625                 630                 635                 640

His Ile Asn Thr Met Ala Ala Arg Pro Ile Trp Gly Asn Val Glu Phe
                645                 650                 655

Trp Gly Pro Trp Asn Phe Asp Pro Asn Leu Lys Leu Thr Leu Asn Ala
            660                 665                 670

Phe Asn Asp Ser Ser Tyr Thr Arg Met Thr Asn Ser Gly Ala Lys Asp
        675                 680                 685

Val Gly Ile Ala Ser Met Thr Ser Tyr Ala Asp Ala Ala Met Ser Phe
        690                 695                 700

Phe Asn Tyr Glu Ala Ser Asn Pro Thr Gly Pro Arg Ala Ala Val Ile
705                 710                 715                 720

Ser Phe Val Arg Asn Gly Ser Arg Gly Val Leu Phe Gly Leu Asp Ser
                725                 730                 735

Asp Asn Lys Leu Lys Trp Gly Gly Tyr Ser Leu Gly Ala Val Ala Phe
            740                 745                 750

Glu Ile Ala Asp Ser Asn Asn Leu Met Ser Leu Trp Ser Ser His Ala
        755                 760                 765

Ala Ala Pro Asn Trp Asn Gly Gln Thr Ile Trp Arg Ser Gly Asn Phe
        770                 775                 780

Asn Pro Asp Thr Lys Ala Thr Leu Ala Ala Arg Asn Thr Thr Ser Ser
785                 790                 795                 800

Pro Thr Ile Phe Ser Tyr Gly Ala Ser Gly Ile Ala Ser Thr Gly Gln
                805                 810                 815

Val Gly Ala Leu Val Val Glu Asn Asn Ser Val Thr Asn Thr Ala Ala
            820                 825                 830

Ala Ile Thr Phe His Ser Pro Gln Lys Tyr Gln Val Asn Phe Gly Leu
        835                 840                 845

Asp Ala Asp Asn Val Val Lys Ile Gly Gly Gly Thr Met Gly Gly Val
        850                 855                 860

Ala Tyr Pro Ile Ile His Ser Gly Asn Tyr Asn Tyr Ile Asn Gln
865                 870                 875                 880

Ala Leu Val Gln Val Gly Leu Gly Gly Val Gly Ser Tyr Ala Ile Leu
                885                 890                 895

Ala Val Leu Asp Thr Ser Ala Pro Ala Ala Ser Ile Ala Pro Gly Thr
```

```
                      900                 905                 910
Ile Met Asp Ser Ser Lys Leu Phe Tyr Ser Ser Cys Asp Ser Thr Tyr
            915                 920                 925

Arg Ser Ser Ala Ser Pro Thr Gly Thr Trp Arg Cys Met Gly Tyr Val
        930                 935                 940

Tyr Asn Arg Asp Ser Thr Asn Gly Asp Ser Ala Ser Leu Phe Gln Arg
945                 950                 955                 960

Val Thr

<210> SEQ ID NO 35
<211> LENGTH: 962
<212> TYPE: PRT
<213> ORGANISM: Bacteriophage PTP92

<400> SEQUENCE: 35

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Ala Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
        115                 120                 125

Trp Ser Val Met Arg Thr Asn Ile Pro Met Pro Ala Gly Gly Pro Gly
    130                 135                 140

Leu Ser Ser Gly Gly Glu Val Ile Thr Thr Gly Arg Asn Phe Asn Glu
145                 150                 155                 160

Leu Leu Asn Gly Thr Trp Glu Phe Phe Ser Asp Ala Ile Val Val Ala
                165                 170                 175

Ser Gln Asn Ala Pro Val Tyr Pro Ala Ser Ala Gly Ala Ala Ala Gly
            180                 185                 190

Met Leu Glu Ala Lys Ser Trp Val Ser Gly Ser Asn Thr Phe Cys Val
        195                 200                 205

Gln Arg Tyr Thr Asp Arg Val Gly Asn Val Ala Val Arg Gly Leu Asn
    210                 215                 220

Ala Gly Ala Trp Thr Asn Trp Met Tyr Ala Val Asn Val Met Ala Leu
225                 230                 235                 240

Gln His Gly Arg Val Thr Tyr Gly Thr Ala Ala Gly Pro Ala Asn Ala
                245                 250                 255

Tyr Thr Leu Thr Leu Val Pro Gln Ile Gln Gly Gly Leu Val Asp Gly
            260                 265                 270

Met Ile Leu Arg Val Lys Phe Asn Thr Met Asn Thr Gly Ala Thr Thr
        275                 280                 285

Ile Asn Val Ser Gly Leu Gly Ala Lys Ala Ile Val Gly Ala Ala Asn
    290                 295                 300

Phe Pro Leu Thr Gly Gly Glu Leu Gly Gln Gly Leu Ile Ala Glu Leu
```

```
            305                 310                 315                 320
Val Phe Asp Ala Ala Gly Asp Arg Trp Arg Ile Leu Ala Gly Ala Pro
                325                 330                 335
Arg Ile Gln Val Gly Asn Ala Asp Gln Asp Tyr Gln Ala Pro Ser Trp
                340                 345                 350
Lys Gln Val Lys Asp Tyr Val Glu Ser Gln Lys Leu Thr Glu Val Asp
                355                 360                 365
Trp Thr Asp Val Val Asn Lys Pro Asn Val Ala Ile Gln Asp Thr Thr
            370                 375                 380
Pro Trp Phe Ala Asn Leu Glu Leu Ser Asp Ala Arg Pro Phe Ile Asp
385                 390                 395                 400
Phe His Phe Asn Ser Asn Arg Ala Lys Asp Phe Asp Tyr Arg Leu Ile
                405                 410                 415
Ser Glu Ala Asp Gly Ser Leu Ala Phe Tyr Ser Arg Gln Gly Ser Ala
                420                 425                 430
Gly Pro Thr Gln Asp Ile Leu Phe Asn Arg Asn Ser Val Thr Phe Phe
                435                 440                 445
Gln Pro Arg Leu Asp Val Ala Lys Asn Leu Ala Tyr Ile Ala Asn Ser
            450                 455                 460
Gly Pro Leu Trp Gln Asn Thr Thr Ala Asp Gln Pro Gly Trp Lys Phe
465                 470                 475                 480
Thr Phe Ala Gln Gly Val Asp Ala Asn Asn Ala Val Ile Ala Val
                485                 490                 495
Asn Thr Thr Asn Pro Asp Gly Ser Tyr Arg Ser Gln Val Met Arg Trp
                500                 505                 510
Asp Trp Ala Ser Thr Asn Val Ile Phe Asn Asn Arg Pro Leu Phe Ala
            515                 520                 525
Gly Gln Tyr Thr Pro Trp Asp Ser Gly Asn Phe Asp Pro Ser Thr Lys
            530                 535                 540
Leu Thr Val Ser Ala Thr Asn Gln Ile Ser Gly Pro Thr Gly Ile Arg
545                 550                 555                 560
Asn Thr Asn Gly Asn Thr Gly Asn Met Asn Thr Trp Gly Ser Gly Ser
                565                 570                 575
Thr Thr Ala Ser Tyr Gly Asn Ala Ala Ile Gln Ile Phe Gly Lys Gly
                580                 585                 590
Gly Gly Glu Pro Ala Ala Ile Tyr Phe Asp Asn Ser Gln Thr Gly Trp
                595                 600                 605
Tyr Leu Gly Met Asp Lys Asp Gly Gln Leu Lys Arg Ala Gly Trp Ser
            610                 615                 620
Leu Gly Asn Asn Ser Tyr Val Ile Thr Asp Glu Ser Asn Ile Arg Thr
625                 630                 635                 640
His Ile Asn Thr Met Ala Ala Arg Pro Ile Trp Gly Asn Val Glu Phe
                645                 650                 655
Trp Gly Pro Trp Asn Phe Asp Pro Asn Leu Lys Leu Thr Leu Asn Ala
                660                 665                 670
Phe Asn Asp Ser Ser Tyr Thr Arg Met Thr Asn Ser Gly Ala Lys Asp
            675                 680                 685
Val Gly Ile Ala Ser Met Thr Ser Tyr Ala Asp Ala Ala Met Ser Phe
            690                 695                 700
Phe Asn Tyr Glu Ala Ser Asn Pro Thr Gly Pro Arg Ala Ala Val Ile
705                 710                 715                 720
Ser Phe Val Arg Asn Gly Ser Arg Gly Val Leu Phe Gly Leu Asp Ser
                725                 730                 735
```

Asp Asn Lys Leu Lys Trp Gly Gly Tyr Ser Leu Gly Ala Val Ala Phe
            740                 745                 750

Glu Ile Ala Asp Ser Asn Asn Leu Met Ser Leu Trp Ser Ser His Ala
            755                 760                 765

Ala Ala Pro Asn Trp Asn Gly Gln Thr Ile Trp Arg Ser Gly Asn Phe
            770                 775                 780

Asn Pro Asp Thr Lys Ala Thr Leu Ala Ala Arg Asn Thr Thr Ser Ser
785                 790                 795                 800

Pro Thr Ile Phe Ser Tyr Gly Ala Ser Gly Ile Ala Ser Thr Gly Gln
                805                 810                 815

Val Gly Ala Leu Val Val Glu Asn Asn Ser Val Thr Asn Thr Ala Ala
            820                 825                 830

Ala Ile Thr Phe His Ser Pro Gln Lys Tyr Gln Val Asn Phe Gly Leu
            835                 840                 845

Asp Ala Asp Asn Val Val Lys Ile Gly Gly Gly Thr Met Gly Gly Val
850                 855                 860

Ala Tyr Pro Ile Ile His Ser Gly Asn Tyr Asn Asn Tyr Ile Asn Gln
865                 870                 875                 880

Ala Leu Val Gln Val Gly Leu Gly Gly Val Gly Ser Tyr Ala Ile Leu
                885                 890                 895

Ala Val Leu Asp Thr Ser Ala Pro Ala Ala Ser Ile Ala Pro Gly Thr
            900                 905                 910

Ile Met Asp Ser Ser Lys Leu Phe Tyr Ser Ser Cys Asp Ser Thr Tyr
            915                 920                 925

Arg Ser Ser Ala Ser Pro Thr Gly Thr Trp Arg Cys Met Gly Tyr Val
            930                 935                 940

Tyr Asn Arg Asp Ser Thr Asn Gly Asp Ser Ala Ser Leu Phe Gln Arg
945                 950                 955                 960

Val Thr

<210> SEQ ID NO 36
<211> LENGTH: 962
<212> TYPE: PRT
<213> ORGANISM: Bacteriophage NH-4

<400> SEQUENCE: 36

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Ala Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Arg Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
        115                 120                 125

Trp Ser Val Met Arg Thr Asn Ile Pro Met Pro Ala Gly Gly Pro Gly
    130                 135                 140

Leu Ser Ser Gly Gly Glu Val Ile Thr Thr Gly Arg Asn Phe Asn Glu
145                 150                 155                 160

Leu Leu Asn Gly Thr Trp Glu Phe Phe Ser Asp Ala Ile Val Val Ala
                165                 170                 175

Ser Gln Asn Ala Pro Val Tyr Pro Ala Ser Ala Gly Ala Ala Ala Gly
            180                 185                 190

Met Leu Glu Ala Lys Ser Trp Val Ser Gly Ser Asn Thr Phe Cys Val
            195                 200                 205

Gln Arg Tyr Thr Asp Arg Val Gly Asn Val Ala Val Arg Gly Leu Asn
        210                 215                 220

Ala Gly Ala Trp Thr Asn Trp Met Tyr Ala Val Asn Val Met Ala Leu
225                 230                 235                 240

Gln His Gly Arg Val Thr Tyr Gly Thr Ala Ala Gly Pro Ala Asn Ala
                245                 250                 255

Tyr Thr Leu Thr Leu Val Pro Gln Ile Gln Gly Gly Leu Val Asp Gly
            260                 265                 270

Met Ile Leu Arg Val Lys Phe Asn Thr Met Asn Thr Gly Ala Thr Thr
            275                 280                 285

Ile Asn Val Ser Gly Leu Gly Ala Lys Ala Ile Val Gly Ala Ala Asn
290                 295                 300

Phe Pro Leu Thr Gly Gly Glu Leu Gly Gln Gly Leu Ile Ala Glu Leu
305                 310                 315                 320

Val Phe Asp Ala Ala Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
                340                 345                 350

Lys Gln Val Lys Asp Tyr Val Ala Ser Gln Lys Leu Thr Glu Val Asp
            355                 360                 365

Trp Thr Asp Val Val Asn Lys Pro Asn Val Ala Ile Gln Asp Thr Thr
        370                 375                 380

Pro Trp Phe Ala Asn Leu Glu Leu Ser Asp Ala Arg Pro Phe Ile Asp
385                 390                 395                 400

Phe His Phe Asn Ser Asn Arg Ala Lys Asp Phe Asp Tyr Arg Leu Ile
                405                 410                 415

Ser Glu Ala Asp Gly Ser Leu Ala Phe Tyr Ser Arg Gln Gly Ser Ala
            420                 425                 430

Gly Pro Thr Gln Asp Ile Leu Phe Asn Arg Asn Ser Val Thr Phe Phe
            435                 440                 445

Gln Pro Arg Leu Asp Val Ala Lys Asn Leu Ala Tyr Ile Ala Asn Ser
        450                 455                 460

Gly Pro Leu Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
                485                 490                 495

Asn Thr Thr Asn Pro Asp Gly Ser Tyr Arg Ser Gln Val Met Arg Trp
            500                 505                 510

Asp Trp Ala Ser Thr Asn Val Ile Phe Asn Asn Arg Pro Leu Phe Ala
        515                 520                 525

Gly Gln Tyr Thr Pro Trp Asp Ser Gly Asn Phe Asp Pro Ser Thr Lys
        530                 535                 540

Leu Thr Val Ser Ala Thr Asn Gln Ile Ala Gly Pro Thr Gly Ile Arg
545                 550                 555                 560

```
Asn Thr Asn Gly Asn Thr Gly Asn Met Asn Thr Trp Gly Ser Gly Ser
            565                 570                 575

Thr Thr Ala Ser Tyr Gly Asn Ala Ala Ile Gln Ile Phe Gly Lys Gly
            580                 585                 590

Gly Gly Glu Pro Ala Ala Ile Tyr Phe Asp Asn Ser Gln Thr Gly Trp
            595                 600                 605

Tyr Leu Gly Met Asp Lys Asp Gly Gln Leu Lys Arg Ala Gly Trp Ser
            610                 615                 620

Leu Gly Asn Asn Ser Tyr Val Ile Thr Asp Glu Ser Asn Ile Arg Thr
625                 630                 635                 640

His Ile Asn Thr Met Ala Ala Arg Pro Ile Trp Gly Asn Val Glu Phe
            645                 650                 655

Trp Gly Pro Trp Asn Phe Asn Pro Asn Thr Lys Leu Thr Leu Gly Ser
            660                 665                 670

Phe Asn Asp Ser Gln His Thr Arg Met Val Asn Ser Ala Ala Lys Asp
            675                 680                 685

Val Gly Ile Ala Ser Met Thr Ser Tyr Ala Asp Ala Met Ser Phe
            690                 695                 700

Phe Asn Tyr Glu Ala Ser Thr Pro Thr Gly Asn Arg Ala Ala Val Ile
705                 710                 715                 720

Ser Phe Val Arg Asn Gly Ala Arg Gly Val Leu Phe Gly Leu Asp Thr
            725                 730                 735

Asp Asn Lys Leu Lys Trp Gly Gly Tyr Ser Leu Gly Ala Val Ala Phe
            740                 745                 750

Glu Ile Ala Asp Ser Asn Asn Leu Met Ser Leu Trp Ser Ser His Ala
            755                 760                 765

Ala Ala Pro Asn Trp Asn Gly Gln Thr Ile Trp Arg Ser Gly Asn Phe
            770                 775                 780

Asn Pro Asp Thr Lys Ala Thr Leu Ala Ala Arg Asn Thr Thr Ser Ser
785                 790                 795                 800

Pro Thr Ile Phe Ser Tyr Gly Ala Ser Gly Ile Ala Ser Thr Gly Gln
            805                 810                 815

Val Gly Ala Leu Val Val Glu Asn Asn Ser Val Thr Asn Thr Ala Ala
            820                 825                 830

Ala Ile Thr Phe His Ser Pro Gln Lys Tyr Gln Val Asn Phe Gly Leu
            835                 840                 845

Asp Ala Asp Asn Val Val Lys Ile Gly Gly Thr Met Gly Gly Val
            850                 855                 860

Ala Tyr Pro Ile Ile His Ser Gly Asn Tyr Asn Asn Tyr Ile Asn Gln
865                 870                 875                 880

Ala Leu Val Gln Val Gly Leu Gly Gly Val Gly Ser Tyr Ala Ile Leu
            885                 890                 895

Ala Val Leu Asp Thr Ser Ala Pro Ala Ala Ser Ile Ala Pro Gly Thr
            900                 905                 910

Ile Met Asp Ser Ser Lys Leu Phe Tyr Ser Ser Cys Asp Ser Thr Tyr
            915                 920                 925

Arg Ser Ser Ala Arg Pro Thr Gly Thr Trp Arg Cys Met Gly Tyr Val
            930                 935                 940

Tyr Asn Arg Asp Ser Thr Asn Gly Asp Ser Ala Ser Leu Phe Gln Arg
945                 950                 955                 960

Val Thr

<210> SEQ ID NO 37
```

<211> LENGTH: 962
<212> TYPE: PRT
<213> ORGANISM: Bacteriophage 14-1

<400> SEQUENCE: 37

```
Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Ala Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
        115                 120                 125

Trp Ser Val Met Arg Ser Ser Ile Pro Met Pro Ala Gly Gly Pro Gly
    130                 135                 140

Leu Ser Ser Gly Gly Glu Val Ile Thr Thr Gly Arg Asn Phe Asn Asp
145                 150                 155                 160

Leu Leu Asn Gly Thr Trp Glu Phe Phe Ser Asp Ser Val Val Ile Ala
                165                 170                 175

Ser Gln Asn Ala Pro Val Tyr Pro Ala Ser Ala Gly Ala Ala Ala Gly
            180                 185                 190

Met Leu Glu Ala Lys Ser Trp Ile Ser Arg Ser Asn Thr Phe Cys Val
        195                 200                 205

Gln Arg Tyr Thr Asp Arg Val Gly Asn Val Ala Val Arg Gly Leu Asn
    210                 215                 220

Ala Gly Glu Trp Thr Asn Trp Met Tyr Ala Val Asn Val Met Ala Leu
225                 230                 235                 240

Gln Gln Gly Arg Val Thr Tyr Gly Val Ala Ala Gly Pro Ala Asn Ala
                245                 250                 255

Tyr Thr Leu Thr Leu Val Pro Gln Leu Gln Gly Gly Leu Val Asp Gly
            260                 265                 270

Met Ile Leu Arg Val Lys Phe Asn Thr Val Asn Thr Gly Ala Ser Thr
        275                 280                 285

Ile Asn Val Ser Gly Leu Gly Ala Lys Ala Ile Val Gly Ala Ala Asn
    290                 295                 300

Phe Pro Leu Thr Gly Gly Glu Leu Gly Gln Gly Leu Ile Ala Glu Leu
305                 310                 315                 320

Val Phe Asp Ala Ala Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
            340                 345                 350

Lys Gln Val Lys Asp Tyr Val Ala Ser Gln Lys Leu Thr Glu Val Asp
        355                 360                 365

Trp Thr Asp Val Val Asn Lys Pro Asn Val Ala Ile Gln Asp Thr Thr
    370                 375                 380

Pro Trp Phe Ala Asn Leu Glu Leu Ser Asp Ala Arg Pro Phe Ile Asp
```

-continued

```
            385                 390                 395                 400
        Phe His Phe Asn Ser Asn Arg Ala Lys Asp Phe Asp Tyr Arg Leu Ile
                        405                 410                 415

Ser Glu Ala Asp Gly Ser Leu Ala Phe Tyr Ser Arg Gln Gly Ser Ala
                        420                 425                 430

Gly Pro Thr Gln Asp Ile Leu Phe Asn Arg Asn Ser Val Thr Phe Phe
                        435                 440                 445

Gln Pro Arg Leu Asp Val Ala Lys Asn Leu Ala Tyr Ile Ala Asn Ser
                450                 455                 460

Gly Pro Ile Trp Gln Asn Thr Thr Ala Asp Gln Pro Gly Trp Lys Phe
        465                 470                 475                 480

Thr Phe Ala Gln Gly Val Asp Ala Asn Asn Asn Ala Val Ile Ala Val
                        485                 490                 495

Asn Thr Thr Asn Pro Asp Gly Ser Tyr Arg Ser Gln Val Met Arg Trp
                        500                 505                 510

Asp Trp Ala Ser Thr Asn Val Ile Phe Asn Asp Arg Pro Leu Phe Ala
                        515                 520                 525

Gly Gln Tyr Thr Pro Trp Asp Ser Gly Asn Phe Asp Pro Ser Thr Lys
                530                 535                 540

Leu Thr Val Ser Ala Thr Asn Gln Ile Ala Gly Pro Thr Gly Ile Arg
        545                 550                 555                 560

Asn Thr Asn Gly Asn Thr Gly Asn Met Asn Thr Trp Gly Ser Gly Ser
                        565                 570                 575

Thr Thr Ala Ser Tyr Gly Asn Ala Ala Ile Gln Ile Phe Gly Lys Gly
                        580                 585                 590

Gly Gly Glu Pro Ala Ala Ile Tyr Phe Asp Asn Ser Gln Thr Gly Trp
                        595                 600                 605

Tyr Leu Gly Met Asp Lys Asp Gly Arg Leu Lys Arg Ala Gly Trp Ser
                        610                 615                 620

Leu Gly Asn Asn Ser Tyr Val Ile Thr Asp Glu Ser Asn Ile Arg Thr
        625                 630                 635                 640

His Ile Asn Thr Met Ala Ala Arg Pro Ile Trp Gly Asn Val Glu Phe
                        645                 650                 655

Trp Gly Pro Trp Asn Phe Asp Pro Asn Leu Lys Leu Thr Leu Asn Ala
                        660                 665                 670

Phe Asn Asp Ser Ser Tyr Thr Arg Met Thr Asn Ser Gly Ala Lys Asp
                        675                 680                 685

Val Gly Ile Ala Ser Met Thr Ser Tyr Ala Asp Ala Ala Met Ser Phe
        690                 695                 700

Phe Asn Tyr Glu Ala Ser Asn Pro Thr Gly Pro Arg Ala Ala Val Ile
        705                 710                 715                 720

Ser Phe Val Arg Asn Gly Ser Arg Gly Val Leu Phe Gly Leu Asp Ser
                        725                 730                 735

Asp Asn Lys Leu Lys Trp Gly Gly Tyr Ser Leu Gly Ala Val Ala Phe
                        740                 745                 750

Glu Ile Ala Asp Ser Asn Asn Leu Met Ser Leu Trp Ser Ser His Ala
                        755                 760                 765

Ala Ala Pro Asn Trp Asn Gly Gln Thr Ile Trp Arg Ser Gly Asn Phe
                        770                 775                 780

Asn Pro Asp Thr Lys Ala Thr Leu Ala Ala Arg Asn Thr Thr Ser Ser
        785                 790                 795                 800

Pro Thr Ile Phe Ser Tyr Gly Ala Ser Gly Ile Ala Ser Thr Gly Gln
                        805                 810                 815
```

```
Val Gly Ala Leu Val Val Glu Asn Asn Ser Val Thr Asn Thr Ala Ala
            820                 825                 830

Ala Ile Thr Phe His Ser Pro Gln Lys Tyr Gln Val Asn Phe Gly Leu
            835                 840                 845

Asp Ala Asp Asn Val Val Lys Ile Gly Gly Thr Met Gly Gly Val
850                 855                 860

Ala Tyr Pro Ile Ile His Ser Gly Asn Tyr Asn Asn Tyr Ile Asn Gln
865                 870                 875                 880

Ala Leu Val Gln Val Gly Leu Gly Gly Val Gly Ser Tyr Gly Ile Phe
            885                 890                 895

Ala Val Leu Asp Asn Ala Ala Pro Ile Ala Thr Val Gln Pro Gly Val
            900                 905                 910

Val Val Asp Gly Ser Ile Leu Ile Tyr Ser Ser Cys Ala Ala Asn Tyr
            915                 920                 925

Asn Ser Gly Gln Arg Pro Ala Gly Thr Trp Arg Cys Met Gly Tyr Val
            930                 935                 940

Val Asn Arg Asp Ala Asn Thr Pro Asp Ser Ala Thr Leu Phe Gln Arg
945                 950                 955                 960

Val Thr

<210> SEQ ID NO 38
<211> LENGTH: 962
<212> TYPE: PRT
<213> ORGANISM: Bacteriophage PTP47

<400> SEQUENCE: 38

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Ala Val Glu Arg Lys Ile Gln Asn Gln Leu Phe Phe Ile
50                  55                  60

Ala Thr Gln Asn Ala Gln Ala Trp Gln Arg Gln Met Ala Pro Pro Trp
65                  70                  75                  80

Phe Gln Asp Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
        115                 120                 125

Trp Ser Ala Met Arg Ser Asn Ile Pro Met Pro Ala Gly Gly Pro Gly
130                 135                 140

Leu Ser Ser Gly Gly Glu Val Ile Thr Thr Gly Arg Asn Phe Asn Asp
145                 150                 155                 160

Leu Leu Asn Gly Thr Trp Glu Phe Phe Ser Asp Ser Val Val Ile Ala
                165                 170                 175

Ser Gln Asn Ala Pro Val Tyr Pro Ala Ser Gly Ala Ala Ala Gly
            180                 185                 190

Met Leu Glu Ala Lys Ser Trp Val Ser Gly Ala Asn Thr Phe Cys Val
        195                 200                 205

Gln Arg Tyr Thr Asp Arg Val Gly Asn Val Ala Val Arg Gly Leu Asn
210                 215                 220
```

```
Ala Gly Ala Trp Thr Asn Trp Met Tyr Ala Val Asn Val Met Ala Leu
225                 230                 235                 240

Gln Gln Gly Arg Val Thr Tyr Gly Val Ala Gly Ser Ala Asn Ala
            245                 250                 255

Tyr Thr Leu Thr Leu Val Pro Gln Leu Gln Gly Gly Leu Val Asp Gly
                260                 265                 270

Met Ile Leu Arg Val Lys Phe Asn Thr Met Asn Thr Gly Ala Thr Thr
            275                 280                 285

Ile Asn Val Ser Gly Leu Gly Ala Lys Ala Ile Val Gly Ala Ala Asn
        290                 295                 300

Phe Pro Leu Thr Gly Gly Glu Leu Gly Gln Gly Leu Ile Ala Glu Leu
305                 310                 315                 320

Val Phe Asp Ala Ala Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
            340                 345                 350

Lys Gln Val Lys Asp Tyr Val Ala Ser Gln Lys Leu Thr Glu Val Asp
                355                 360                 365

Trp Ala Asp Val Val Asn Lys Pro Asn Val Ala Ile Gln Asp Thr Thr
370                 375                 380

Pro Trp Phe Ala Asn Leu Glu Leu Ser Asp Ala Arg Pro Phe Ile Asp
385                 390                 395                 400

Phe His Phe Asn Ser Asn Arg Ala Lys Asp Phe Asp Tyr Arg Leu Ile
                405                 410                 415

Ser Glu Ala Asp Gly Ser Leu Ala Phe Tyr Ser Arg Gln Gly Ser Ala
                420                 425                 430

Gly Pro Thr Gln Asp Ile Leu Phe Asn Arg Asn Ser Val Thr Phe Phe
            435                 440                 445

Gln Pro Arg Leu Asp Val Ala Lys Asn Leu Ala Tyr Ile Ala Asn Ser
450                 455                 460

Gly Pro Leu Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
                485                 490                 495

Asn Thr Thr Asn Pro Asp Gly Ser Tyr Arg Ser Gln Val Met Arg Trp
                500                 505                 510

Asp Trp Ala Ser Thr Asn Val Ile Phe Asn Asn Arg Pro Leu Phe Ala
            515                 520                 525

Gly Gln Tyr Thr Pro Trp Asp Ser Gly Asn Phe Asp Pro Ser Thr Lys
            530                 535                 540

Leu Thr Val Ser Ala Thr Asn Gln Ile Ala Gly Pro Thr Gly Ile Arg
545                 550                 555                 560

Asn Thr Asn Gly Asn Thr Gly Asn Met Asn Thr Trp Gly Ser Gly Ser
                565                 570                 575

Thr Thr Ala Ser Tyr Gly Asn Ala Ala Ile Arg Ile Phe Gly Lys Gly
                580                 585                 590

Gly Gly Glu Pro Ala Ala Ile Tyr Phe Asp Asn Ser Gln Thr Gly Trp
            595                 600                 605

Tyr Leu Gly Met Asp Lys Asp Gly Gln Leu Lys Arg Ala Gly Trp Ser
            610                 615                 620

Leu Gly Asn Asn Ser Tyr Val Ile Thr Asp Glu Ser Asn Ile Arg Thr
625                 630                 635                 640
```

His Ile Asn Thr Met Ala Ala Arg Pro Ile Trp Gly Asn Val Glu Phe
                645                 650                 655

Trp Gly Pro Trp Asn Phe Asn Pro Asn Thr Lys Leu Thr Leu Gly Ser
        660                 665                 670

Phe Asn Asp Gly Gln His Thr Arg Met Val Asn Ser Ala Ala Lys Asp
    675                 680                 685

Val Gly Ile Ala Ser Met Thr Ser Tyr Ala Asp Ala Ala Met Ser Phe
690                 695                 700

Phe Asn Tyr Glu Ala Ser Thr Pro Thr Gly Asn Arg Ala Ala Val Ile
705                 710                 715                 720

Ser Phe Val Arg Asn Gly Ala Arg Gly Val Leu Phe Gly Leu Asp Thr
                725                 730                 735

Asp Asn Lys Leu Lys Trp Gly Gly Tyr Ser Leu Gly Ala Val Ala Phe
            740                 745                 750

Glu Ile Ala Asp Ser Asn Asn Leu Met Ser Leu Trp Ser Ser His Ala
        755                 760                 765

Ala Ala Pro Asn Trp Asn Gly Gln Thr Ile Trp Arg Ser Gly Asn Phe
    770                 775                 780

Asn Pro Asp Thr Lys Ala Thr Leu Ala Ala Arg Asn Thr Thr Ser Ser
785                 790                 795                 800

Pro Thr Ile Phe Ser Tyr Gly Ala Ser Gly Ile Ala Ser Thr Gly Gln
                805                 810                 815

Val Gly Ala Leu Val Val Glu Asn Asn Ser Val Thr Asn Thr Ala Ala
            820                 825                 830

Ala Ile Thr Phe His Ser Pro Gln Lys Tyr His Val Asn Phe Gly Leu
        835                 840                 845

Asp Ala Asp Asn Val Val Lys Ile Gly Gly Gly Thr Met Gly Gly Val
    850                 855                 860

Ala Tyr Pro Ile Ile His Ser Gly Asn Tyr Asn Asn Tyr Ile Asn Gln
865                 870                 875                 880

Ala Leu Val Gln Val Gly Leu Gly Glu Val Gly Ser Tyr Gly Ile Phe
                885                 890                 895

Ala Val Leu Asp Tyr Ala Ala Pro Thr Ala Thr Val Arg Pro Gly Val
            900                 905                 910

Val Val Asp Gly Ser Ile Leu Ile Tyr Ser Ser Cys Ala Ala Asn Tyr
        915                 920                 925

Asn Ser Gly Gln Arg Pro Ala Gly Thr Trp Arg Cys Met Gly Tyr Val
    930                 935                 940

Val Asn Arg Asp Ala Asn Thr Pro Asp Ser Ala Thr Leu Phe Gln Arg
945                 950                 955                 960

Val Thr

<210> SEQ ID NO 39
<211> LENGTH: 962
<212> TYPE: PRT
<213> ORGANISM: Bacteriophage SN

<400> SEQUENCE: 39

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

```
Gln Ala Lys Ala Val Glu Arg Lys Ile Gln Asn Gln Leu Phe Phe Ile
 50                  55                  60
Ala Thr Gln Asn Ala Gln Ala Trp Gln Arg Gln Met Ala Pro Pro Trp
 65                  70                  75                  80
Phe Gln Gly Met Pro Gly Gly Tyr Gln Asn Ala Glu Val Val Arg
                 85                  90                  95
Val Gly Asn Asp Gly Ile Met Arg Arg Tyr Arg Ser Met Val Asn Ala
                100                 105                 110
Asn Ala Ser Asp Pro Leu Ser Thr Thr Trp Glu Gln Pro Ala
                115                 120                 125
Trp Ser Val Met Arg Ser Asn Ile Pro Met Pro Ala Gly Gly Pro Gly
130                 135                 140
Leu Ser Ser Gly Gly Glu Val Ile Thr Thr Gly Arg Asn Phe Asn Asp
145                 150                 155                 160
Leu Leu Asn Gly Thr Trp Glu Phe Phe Ser Asp Ser Val Val Ala
                165                 170                 175
Ser Gln Asn Ala Pro Val Tyr Pro Ala Ser Ala Gly Ala Ala Gly
                180                 185                 190
Met Leu Glu Ala Lys Ser Trp Val Ser Gly Ala Asn Thr Phe Cys Val
                195                 200                 205
Gln Arg Tyr Thr Asp Arg Val Gly Asn Val Ala Val Arg Gly Leu Asn
                210                 215                 220
Ala Gly Ala Trp Thr Asn Trp Met Tyr Ala Val Asn Val Met Ala Leu
225                 230                 235                 240
Gln Gln Gly Arg Val Thr Tyr Gly Val Ala Ala Gly Ser Ala Asn Ala
                245                 250                 255
Tyr Thr Leu Thr Leu Val Pro Gln Leu Gln Gly Gly Leu Val Asp Gly
                260                 265                 270
Met Ile Leu Arg Val Lys Phe Asn Thr Met Asn Thr Gly Ala Ser Thr
                275                 280                 285
Ile Asn Val Ser Gly Leu Gly Ala Lys Ala Ile Val Gly Ala Ala Asn
                290                 295                 300
Phe Pro Leu Thr Gly Gly Glu Leu Gly Gln Gly Leu Ile Ala Glu Leu
305                 310                 315                 320
Val Phe Asp Ala Ala Gly Asp Arg Trp Arg Ile Leu Ala Gly Ala Pro
                325                 330                 335
Arg Ile Gln Val Gly Asn Ala Asp Gln Asp Tyr Gln Ala Pro Ser Trp
                340                 345                 350
Lys Gln Val Lys Asp Tyr Val Ala Ser Gln Lys Leu Thr Glu Val Asp
                355                 360                 365
Trp Ala Asp Val Val Asn Lys Pro Asn Val Ala Ile Gln Asp Thr Thr
370                 375                 380
Pro Trp Phe Ala Asn Leu Glu Leu Ser Asp Ala Arg Pro Phe Ile Asp
385                 390                 395                 400
Phe His Phe Asn Ser Asn Arg Ala Lys Asp Phe Asp Tyr Arg Leu Ile
                405                 410                 415
Ser Glu Ala Asp Gly Ser Leu Ala Phe Tyr Ser Arg Gln Gly Ser Ala
                420                 425                 430
Gly Pro Thr Gln Asp Ile Leu Phe Asn Arg Asn Ser Val Thr Phe Phe
                435                 440                 445
Gln Pro Arg Leu Asp Val Ala Lys Asn Leu Ala Tyr Ile Ala Asn Ser
450                 455                 460
Gly Ser Leu Trp Gln Asn Thr Thr Ala Asp Gln Pro Gly Trp Lys Phe
```

-continued

```
            465                 470                 475                 480
        Thr Phe Ala Gln Gly Val Asp Ala Asn Asn Ala Val Ile Ala Val
                        485                 490                 495
        Asn Thr Thr Asn Pro Asp Gly Ser Tyr Arg Ser Gln Val Met Arg Trp
                            500                 505                 510
        Asp Trp Ala Ser Thr Asn Val Ile Phe Asn Asn Arg Pro Leu Phe Ala
                        515                 520                 525
        Gly Gln Tyr Thr Pro Trp Asp Ser Gly Asn Phe Asp Pro Ser Thr Lys
                        530                 535                 540
        Leu Thr Val Arg Ala Thr Asn Gln Ile Ala Gly Pro Thr Gly Ile Gln
        545                 550                 555                 560
        Asn Thr Asn Gly Asn Thr Gly Asn Met Asn Thr Trp Gly Ser Gly Ser
                            565                 570                 575
        Thr Thr Ala Ser Tyr Gly Asn Ala Ala Ile Gln Ile Phe Gly Lys Gly
                        580                 585                 590
        Gly Gly Glu Pro Ala Ala Ile Tyr Phe Asp Asn Ser Gln Thr Gly Trp
                        595                 600                 605
        Tyr Leu Gly Met Asp Lys Asp Gly Gln Leu Lys Arg Ala Gly Trp Ser
                        610                 615                 620
        Leu Gly Asn Asn Ser Tyr Val Ile Thr Asp Glu Ser Asn Ile Arg Thr
        625                 630                 635                 640
        His Ile Asn Thr Met Ala Ala Arg Pro Ile Trp Gly Gly Val Glu Phe
                            645                 650                 655
        Trp Gly Pro Trp Asn Phe Asn Pro Asn Thr Lys Leu Thr Leu Gly Ser
                        660                 665                 670
        Phe Asn Asp Ser Gln His Thr Arg Met Val Asn Ser Ala Ala Lys Asp
                        675                 680                 685
        Val Gly Ile Ala Ser Met Thr Ser Tyr Ala Asp Ala Met Ser Phe
                        690                 695                 700
        Phe Asn Tyr Glu Ala Ser Thr Pro Thr Gly Asn Arg Ala Ala Val Ile
        705                 710                 715                 720
        Ser Phe Val Arg Asn Gly Ala Arg Gly Val Leu Phe Gly Leu Asp Thr
                            725                 730                 735
        Asp Asn Lys Leu Lys Trp Gly Gly Tyr Ser Leu Gly Ala Val Ala Phe
                        740                 745                 750
        Glu Ile Ala Asp Ser Asn Asn Leu Met Ser Leu Trp Ser Ser His Ala
                        755                 760                 765
        Ala Ala Pro Asn Trp Asn Gly Gln Thr Ile Trp Arg Ser Gly Asn Phe
                        770                 775                 780
        Asn Pro Asp Thr Lys Ala Thr Leu Ala Ala Arg Asn Thr Thr Ser Ser
        785                 790                 795                 800
        Pro Thr Ile Phe Ser Tyr Gly Ala Ser Gly Ile Ala Ser Thr Gly Gln
                            805                 810                 815
        Val Gly Ala Leu Val Val Glu Asn Asn Ser Val Thr Asn Thr Ala Ala
                        820                 825                 830
        Ala Ile Thr Phe His Ser Pro Gln Lys Tyr Gln Val Asn Phe Gly Leu
                        835                 840                 845
        Asp Ala Asp Asn Val Val Lys Ile Gly Gly Thr Met Gly Gly Val
                        850                 855                 860
        Ala Tyr Pro Ile Ile His Ser Gly Asn Tyr Asn Asn Tyr Ile Asn Gln
        865                 870                 875                 880
        Ala Leu Val Gln Val Gly Leu Gly Gly Val Gly Ser Tyr Gly Ile Phe
                            885                 890                 895
```

-continued

```
Ala Val Leu Asp Asn Ala Ala Pro Thr Ala Thr Val Gln Pro Gly Val
            900             905             910

Val Val Asp Gly Ser Ile Leu Ile Tyr Ser Ser Cys Ala Ala Asn Tyr
        915             920             925

Asn Ser Gly Gln Arg Pro Ala Gly Thr Trp Arg Cys Met Gly Tyr Val
    930             935             940

Val Asn Arg Asp Ala Asn Thr Pro Asp Ser Ala Thr Leu Phe Gln Arg
945             950             955             960

Val Thr
```